(12) United States Patent
Sugino et al.

(10) Patent No.: US 9,598,672 B2
(45) Date of Patent: Mar. 21, 2017

(54) PRODUCTION OF EXTRACELLULAR MATRIX, CONDITIONED MEDIA AND USES THEREOF

(71) Applicant: Rutgers, The State University of New Jersey, New Brunswick, NJ (US)

(72) Inventors: Ilene Sugino, Madison, NJ (US); Marco Zarbin, Chatham, NJ (US); Qian Sun, West Orange, NJ (US); Raymond B. Birge, New York, NY (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/582,851

(22) Filed: Dec. 24, 2014

(65) Prior Publication Data
US 2015/0118200 A1 Apr. 30, 2015

Related U.S. Application Data

(60) Division of application No. 13/440,912, filed on Apr. 5, 2012, now abandoned, which is a continuation-in-part of application No. 12/738,839, filed as application No. PCT/US2008/080408 on Oct. 19, 2008, now abandoned.

(60) Provisional application No. 61/561,224, filed on Nov. 17, 2011, provisional application No. 60/999,601, filed on Oct. 19, 2007.

(51) Int. Cl.
| | |
|---|---|
| *C12N 5/00* | (2006.01) |
| *C12N 5/02* | (2006.01) |
| *C12N 5/079* | (2010.01) |
| *A61K 35/30* | (2015.01) |
| *A61K 35/44* | (2015.01) |
| *A61K 35/00* | (2006.01) |

(52) U.S. Cl.
CPC ............ *C12N 5/0621* (2013.01); *A61K 35/30* (2013.01); *A61K 35/00* (2013.01); *C12N 2501/115* (2013.01); *C12N 2533/90* (2013.01); *Y10T 428/1348* (2015.01)

(58) Field of Classification Search
None
See application file for complete search history.

(56) References Cited

U.S. PATENT DOCUMENTS

| | | | |
|---|---|---|---|
| 2003/0096750 A1* | 5/2003 | Tombran-Tink | C07K 14/475 514/1.4 |
| 2005/0037491 A1 | 2/2005 | Mistry et al. | |
| 2006/0002900 A1 | 1/2006 | Binder et al. | |
| 2006/0234376 A1 | 10/2006 | Mistry et al. | |
| 2007/0196919 A1 | 8/2007 | Reh et al. | |

OTHER PUBLICATIONS

Sage et al. Arteriosclerosis, Thrombosis, and Vascular Biology, 1981; 1:427-442.*
Abdelsalam et al., "Drusen in age-related macular degeneration: pathogenesis, natural course, and laser photocoagulation-induced regression". Surv Ophthalmol 1999;44:1-29. Abstract only.
Algvere, P.V., et al., "Transplantation of fetal retinal pigment epithelium in age-related macular degeneration with subjoveal neovascularization", Graefes Arch Clin Exp Ophthalmol 1994; 232:707-716. Abstract only.
Binder, S., et al., "Transplantation of autologous retinal pigment epithelium in eyes with foveal neovascularization resulting from age-related macular degeneration: a pilot study", Am J Ophthalmol 2002; 133:215-225. Abstract only.
Bonanno, JA, et al., "Apical and basolaterial CO2—HCO3-permeability in cultured bovine corneal endothelial cells", Am J Physiol Cell Physiol 277: C545-0553, Sep. 1999 Abstract only.
Castellarin, AA, et al., "Progressive presumed choriocapillaris atrophy after surgery for age-related macular degeneration", Retina 1998; 18:143-149. Abstract only.
Castillo, BV, et al., "Efficacy of nonfetal human RPE for photoreceptor rescue: a study in dystrophic RCS rats", Exp Neurol 1997; 146:1-9. Abstract only.
Del Priore et al., "Extracellular matrix ligands promote RPE attachment in inner Bruch's membrane", Curr Eye Res. Aug. 2002; 25(2):79-89.
Del Priore, LV, et al., "Retinal pigment epithelial cell transplantation after subfoveal membranectomy in age-related mascular degeneration: clinicopathological correlation", Am J Ophthalmol Apr. 2001; 131(4):472-480. Abstract only.
Enzmann, V. et al., "Enhanced induction of RPE lineage markers in pluripotent neural stem cells engrafted into the adult rat subretinal space", Investig. Ophthalmol. Visual Sci. Dec. 2003; 44(12):5417-5422. Abstract only.
Gias, C. et al., "Preservation of visual cortical function following retinal pigment epithelium transplantation in the RCS rat using optical imaging techniques", The European journal of neuroscience Apr. 2007; 25(7):1940-1948. Abstract only.
Gospodarowicz, D. et al., "Stimulation of corneal endothelial cell proliferation in vitro by fibroblast and epidermal growth factors", Experimental Eye Research, Jul. 1977; vol. 25, Issue 1:75-89. Abstract only.
Gospodarowicz, D., et al, "Are factors originative from serum, plasma, or cultured cells involved in the growth-promoting effect of the extracellular matrix produced by cultured bovine corneal endothelial cells?", J Cell Physiol. Feb. 1983; 114(2):191-202. Abstract only.
Gullapalli, VK, et al., "Impaired RPE survival on aged submacular human Bruch's membrane", Exp Eye Res Feb. 2005; 80(2):235-248. Abstract only.
Gullapalli, VK, et al., "Retinal pigment epithelium resurfacing of aged submacular human Bruch's membrane", Trans Am Ophthalmol Soc. 2004; 102:123-37; discussion 137-8. Abstract only.

(Continued)

*Primary Examiner* — Doug Schultz
(74) *Attorney, Agent, or Firm* — Fox Rothschild LLP

(57) ABSTRACT

Provided is a matrix for promoting survival and differentiation of cells transplanted thereon, comprising a base matrix and a cell-made matrix thereon. Methods and means for making and using same are also provided. Also provided are conditioned media, related compositions, related methods, and related packaging products.

9 Claims, 30 Drawing Sheets

(56) References Cited

OTHER PUBLICATIONS

Guymer, R., et al., Changes in Bruch's membrane and related structures with age, Prog Retin Eye Res Jan. 1999; 18(1):59-90.
Hsu, JK, et al., "Clinicopathologic studies of an eye after submacular membranectomy for choroidal neovascularization", Retina. 1995; 15(1):43-52. Abstract only.
Ishida, M., et al., "Culture of human retinal pigment epithelial cells from peripheral scleral flap biopsies", Curr Eye Res. Apr. 1998; 17: 392-402. Abstract only.
Itaya H. et al. "Iris pigment epithelium attachment to aged submacular human Bruch's membrane", Invest Ophthalmol Vis. Sci. Dec. 2004;45(12):4520-8.
Joussen, A.M., et al., "Autologous translocation of the choroid and retinal pigment epithelium in age-related macular degeneration", Am J Ophthalmol Jul. 2006; 142(1):17-30. Abstract only.
Katz, A., et al, "Enatactin/Nidogen: Systhesis by Bovine Corneal Endothelial Cells and Distribution in the Human Cornea", Investigative Ophthalmoloty & Visual Science, Feb. 1994; 35(2):495-502.
Kay, E., et al., "Modulation of Type III Collagen Synthesis in Bovine Corneal Endothelial Cells", Investigative Ophthalmology & Visual Science, Feb. 1988; 29(2):200-7.
Kicic, A. et al., "Differentiation of Marrow Stromal Cells into Photoreceptors in the Rat Eye", Aug. 27, 2003, Journal of Neuroscience. 23(21): 7742-7749.
Lund, R.D. et al., "Subretinal transplantation of genetically modfied human cell lines attenuates loss of visual function in dystrophic rats", Proceedings of the National Academy of Sciences U S A 2001;98(17):9942-9947. Abstract only.
Lund, R.D. et al. "Retinal transplantation: progress and problems in clinical application", Jun. 16, 2003, J. Leukocyte Biol. 74(2): 151-160.
MacCallum, D., et al., "Bovine Corneal Endothelium in Vitro", Experimental Cell Research, 1982; 139:1-13.
Nasir, M. et al., "Decreased choriocapillaris perfusion following surgical excision of chorodial neovascular membranes in age-related macular degeneration", Br J Ophthalmol Jun. 1997; 81(6):481-489.
Nevo, Z., et al., "Extracellular matrix (ECM) proteoglycans produced by cultured bovine corneal endothelial cells", Connect Tissue Res. 1984;13(1):45-57. Abstract only.
Pauleikhoff, D., et al., "Adhesive properties of basal membranes of Bruch's membrane. Immunohistochemical studies of age-dependent changes in adhesive molecules and lipid deposits", Ophthalmologe Apr. 2000; 97(4):243-250. Abstract only.
Robinson, J., et al., "Glycosaminogly synthesized by cultured bovine corneal endothelial cells", J Cell Physiol. Dec. 1983; 117(3):368-76. Abstract only.
Rosa, RH., et al., "Clinicopathologic correlation of submacular membranectomy with retention of good vision in a patien with age-related macular degeneration", Arch Ophthalmol Apr. 1996; 114(4):480-487. Abstract only.
Sawada, H., et al., "Immunoelectronmicroscopic localization of extracellular matrix components produced by bovine corneal endothelial cells in vitro", Exp Cell Res. Jul. 1987; 171(1):94-109. Abstract only.
Sugino et al., "Cell-deposited matrix improves retinal pigment epithelium survival on aged submacular human Bruch's membrane," Invest Ophthalmol Vis Sci, 2011, vol. 52, pp. 1345-1358.

Sugino et al., "Comparison of FRPE and human embryonic stem cell-derived RPE behavior on aged human Bruch's membrane," Invest Ophthalmol Vis Sci, 2011, vol. 52, pp. 4979-4997.
Tezel, TH et al., "Reattachment to a substrate prevents apoptosis of human retinal pigment epithelium", Graefes Arch Clin Exp Ophthalmol Jan. 1997; 235(1):41-47. Abstract only.
Tezel, TH., et al., "Adult retinal pigment epithelian transplantation in exudated age-related macular degeneration", Am J Ophthalmol Apr. 2007; 143(4):584-595. Abstract only.
Thomas, MA., et al., "Surgical removal of subfoveal neovasularization in the presume ocular histoplasmosis syndrome", Am J Ophthalmol Jan. 15, 1991; 111(1):1-7. Abstract only.
Tomita, M. et al., "Bone Marrow-Derived Stem Cells Can Differentiate into Retinal Cells in Injured Rat Retina", Stem Cells, 2002; 20: 279-283.
Tseng, S., et al., "Characterization of Collagens Synthesized by Cultured Bovine Corneal Endotheilial Cells", The Journal of Biological Chemistry. Apr. 10, 1981; 256(7):3361-3365.
Tseng, S.C.G., et al., "Modulation of Collagen Synthesis by a Growth Factor and by the Extracellular Matriz: Comparison of Cellular Response to Two Different Stimuli", The Journal of Cell Biology; Sep. 1, 1983; 97:803-809.
Tsukahara, I., et al., "Early attachment of uncultured retinal pigment epithelium from aged donors onto Bruch's memrane explants", Exp Eye Res Feb. 2002; 74(2):255-266. Abstract only.
Ho et al., "En bloc transfer of extracellular matrix in vitro", Current Eye Research, Oxford University Press, 1996, pp. 991-996. Abstract only.
Vlodaysky, I, "Unit 10.4 Preparation of Extracellular Matrices Produced by Cultured Corneal Endothelial and PF-HR9 Endodermal Cells", Curr Protocols Cell Biol 1999; 10.4.1-10.4.14. Abstract only.
Wang, S., et al., "Morphological and Functional Rescue in RCS Rats after RPE Cell Line Transplantation at a Later Stage of Degeneration", Investigative Ophthalmololgy & Visual Science; Jan. 2008; 49(1):416-421.
Wang, H., et al., "Migration and proliferation of retinal pigment epithelium on extracellular mitrix ligants", Journal of Rehabilitation Research & Development; Sep./Oct. 2006; 43(5): 713-22.
Wang, H., et al., "Retinal Pigment Epithelium Wound Healing in Human Bruch's Membrane Explants" Investigative Ophthalmology & Visual Science. May 2003; 44(5):2199-2210.
Wang, H., et al., "Short-term study of retinal pigment epithelium sheet transplants onto Bruch's membrane", Experimental Eye Research; Jan. 2004;78(1):53-65.
Wang, H., et al., "Short-Term Study of Allogeneic Retinal Pigment Epithelium Transplants onto Debrided Bruch's Membrane", Investigative Ophthalmology and Visual Science, Nov. 2001; 42(12):2990-2999.
Zarbin, M., "Analysis of retinal pigment epithelium integrin expression and adhesion membrane", Trans Am Ophthalmol Soc. 2003; 101:499-520. Abstract only.
Zarbin, MA, "Current concepts in the pathogenesis of age-related macular degeneration", Arch Ophthalmol. Apr. 2004; 122(4):598-614. Abstract only.
International Preliminary Report on Patentability for PCT/US08/80408 dated Apr. 20, 2010.
International Search Report for PCT/US08/80408 dated Dec. 17, 2008.
Written Opinion for PCT/US08/80408 dated Dec. 17, 2008.

* cited by examiner

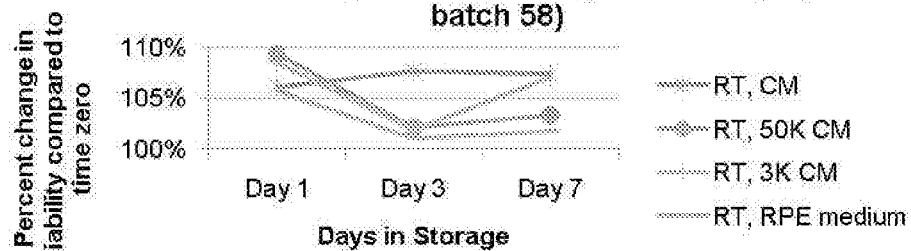
Fig. 18 Change in cell viability after storage (CM batch 58)
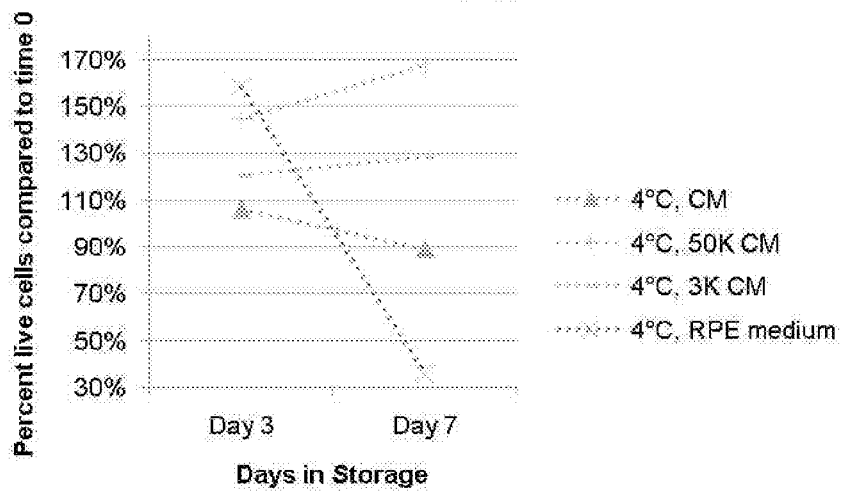
Fig. 19 Change in live cells after storage at 4°C
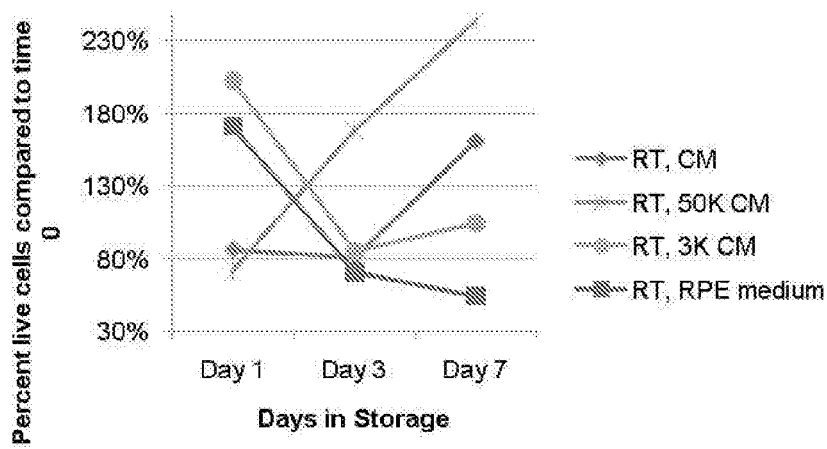
Fig. 20 Change in live cells after storage at room temperature

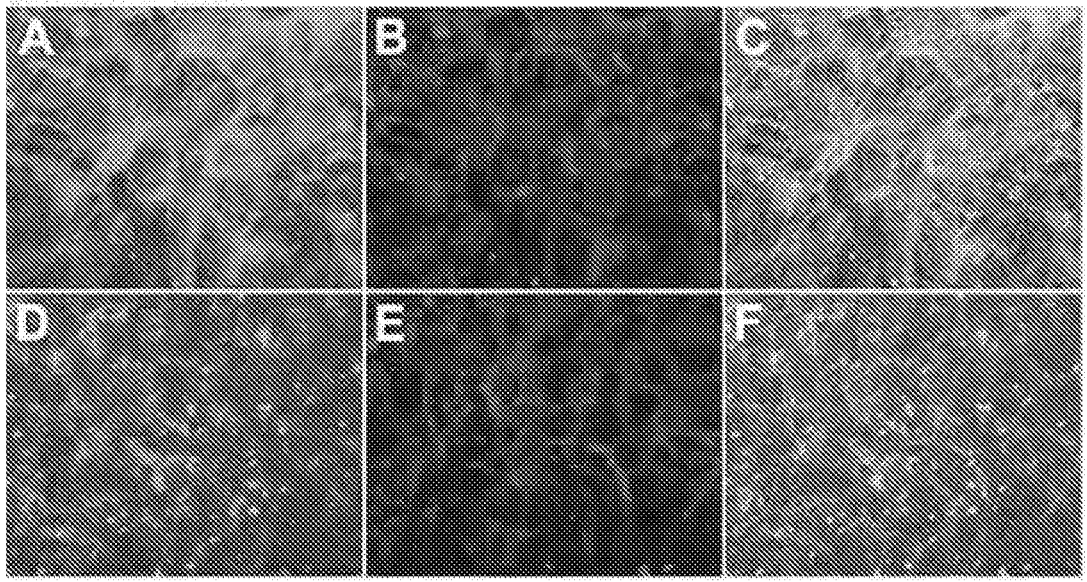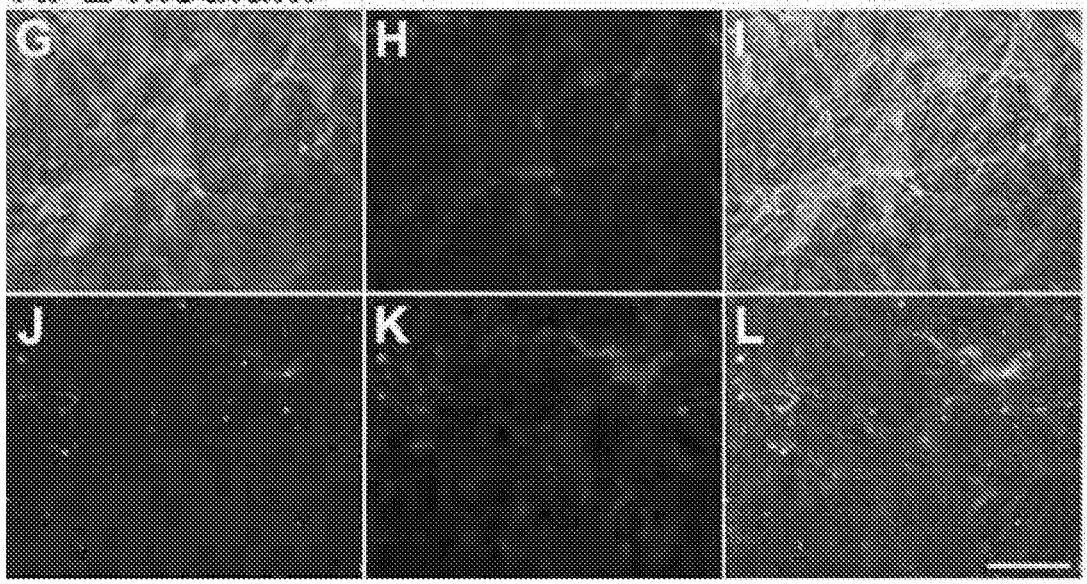
Fig. 33

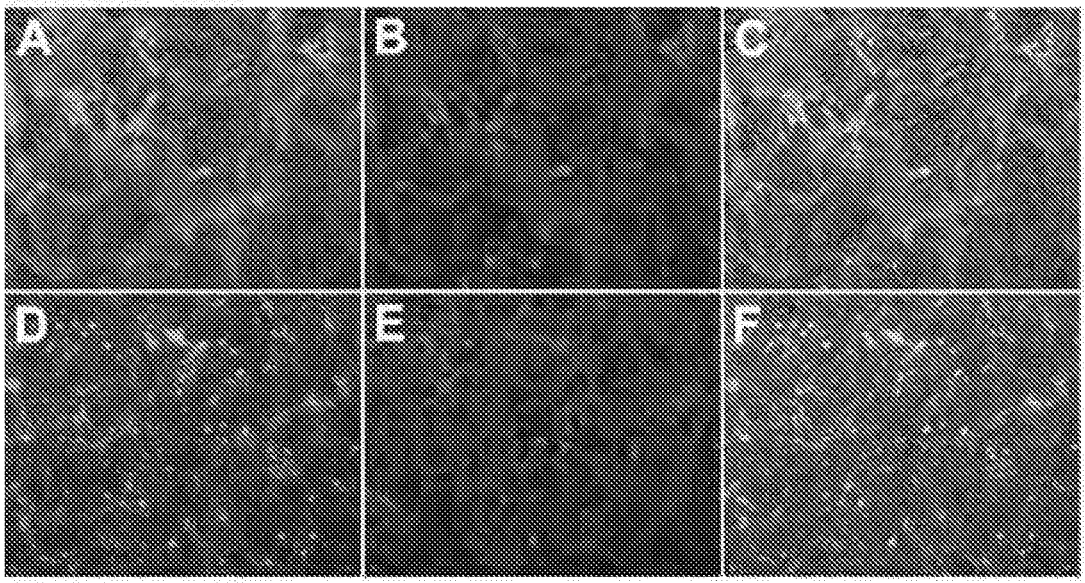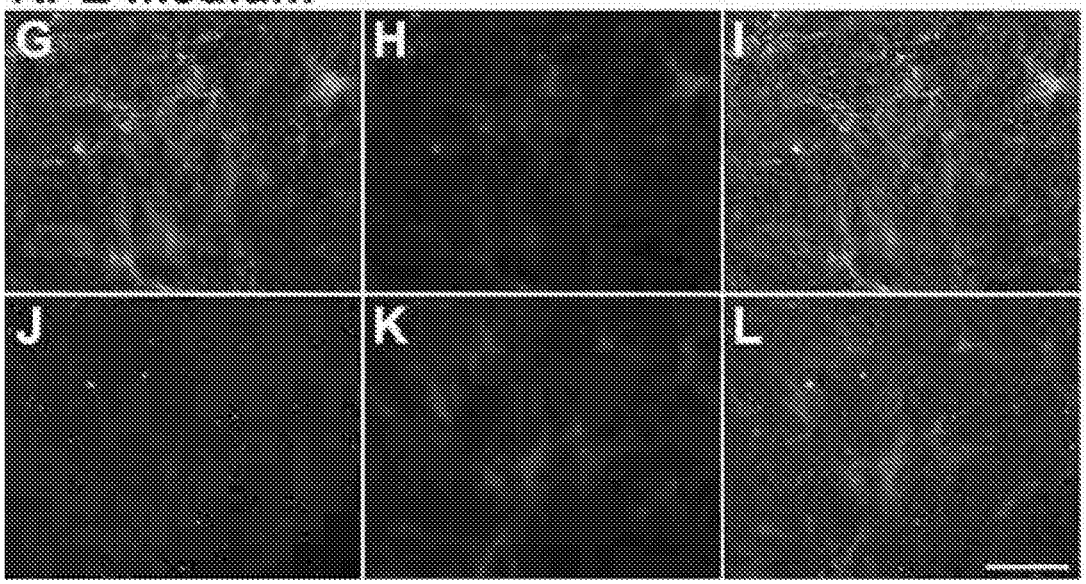
Fig. 34

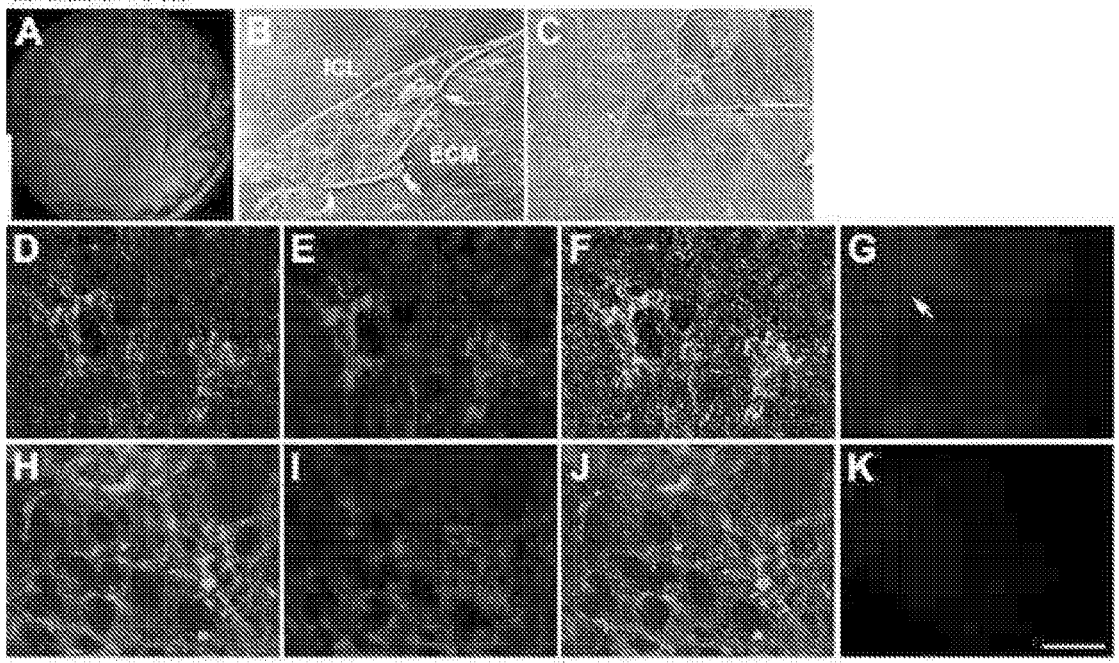
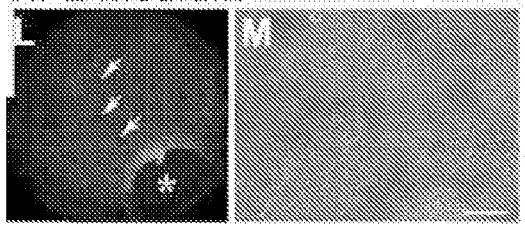
Fig. 35

PRODUCTION OF EXTRACELLULAR MATRIX, CONDITIONED MEDIA AND USES THEREOF

CROSS REFERENCE TO RELATED APPLICATIONS

This application claims priority of U.S. Provisional Application No. 61/471,951 filed on Apr. 5, 2011 and U.S. Provisional Application No. 61/561,224 filed on Nov. 17, 2011. This application is a continuation-in-part of U.S. patent application Ser. No. 12/738,839, which is a 35 U.S.C. §371 National Phase application of International Application Serial No. PCT/US2008/080408, filed Oct. 19, 2008, which claims benefit of priority under 35 U.S.C. §119(e) to U.S. Provisional Application No. 60/999,601 filed on Oct. 19, 2007. The disclosures of the aforementioned applications are incorporated herein by reference.

GOVERNMENTAL SUPPORT

The Research leading to the present invention was supported in part, by National Institutes of Health Grant No. NIH RO3 EY013690. Accordingly, the U.S. Government has certain rights in this invention.

FIELD OF INVENTION

This invention relates to the production of an extracellular matrix, conditioned media, and related uses.

BACKGROUND

Disease-related changes may mask extracellular matrix ligand availability to transplanted cells, impairing post-attachment events and leading, in turn, to cell death or inability of the cells to differentiate. In addition, disease-related changes in the extracellular matrix can promote cell death, leading to the clinical situation in which cell transplantation is contemplated.

One of the conditions in which cell transplantation may be useful is age-related macular degeneration. (In addition, other conditions affecting the macula, such as retinitis pigmentosa and Stargardt disease, may benefit from cell-based therapy.) The macula lutea is an area of the retina that is about 5000 µm in diameter. The center of the macula, the fovea, contains specialized photoreceptors and provides high acuity vision necessary for reading, driving, and recognizing faces. In order for light-sensing photoreceptors to function properly, they must be in intimate contact with a cell layer called the retinal pigment epithelium (RPE). The photoreceptors and RPE exchange nutrients and other materials. The choroid is a vascular layer of the eye wall interposed between the sclera and RPE, and its capillaries, termed the choriocapillaris, provide the blood supply to the RPE and photoreceptors. The RPE is separated from the choriocapillaris by a thin layer of collagenous tissue called Bruch's membrane.

Age-related macular degeneration (AMD) is the most important cause of new cases of blindness in patients older than 55 years of age in the industrialized world. RPE cells may be one of the targets of the pathological processes that cause AMD. Approximately 10% of patients with AMD lose central vision. Among the ~75% of AMD patients with central visual loss, abnormal blood vessels, termed choroidal new vessels (CNVs), grow from the choriocapillaris and leak fluid and blood under the RPE and macula (exudative or "wet" AMD), which causes visual loss. The stimulus for CNV growth in AMD is complex, and the biochemical pathways are now being identified. One critical element is vascular endothelial growth factor (VEGF), which is involved in CNV growth and leakage. Among ~25% of AMD patients with severe central visual loss, the RPE and foveal photoreceptors die in the absence of CNVs (atrophic or "dry" AMD, also termed geographic atrophy (GA)). No visually beneficial treatment exits for ~60-75% of AMD patients.

Existing therapy has significant limitations. Antioxidants, for example, do not seem to be effective in the prevention of early AMD (i.e., drusen, retinal pigmentary changes). The Age-Related Eye Disease Study (AREDS) did not show a statistically significant benefit of the AREDS vitamin and mineral formulation for either the development of new geographic atrophy or for involvement of the fovea in eyes with pre-existing geographic atrophy.

Pharmacological therapies (e.g., AVASTIN® and LUCENTIS®, both of which block the action of VEGF) that are pathway-based have provided the best treatment results for AMD patients that have ever been reported. Nonetheless, a need for improved therapy remains. Although LUCENTIS® treatment is associated with moderate visual improvement in 25-40% of patients according to the results of two randomized studies, the remaining 60-75% of patients are in urgent need of an alternative approach. Also, these medications currently are administered via repeated intravitreal injection, which entails some risk and inconvenience for the patient. Further, pharmacological therapy generally involves administration of a finite number of compounds and usually involves fluctuations in drug levels above and below the desired level.

Accordingly, novel methods and compositions are desired which would address these drawbacks of currently accepted treatment of AMD.

SUMMARY OF INVENTION

The instant invention addresses the drawbacks of the prior art by providing, in one aspect, a modified base matrix for promoting survival and/or differentiation of target cells thereon, the modified base matrix comprising a cell-made extracellular matrix (which is a mixture of proteins and other substances) on its surface.

In different embodiments of the invention, the step of creating the cell-made extracellular matrix may be achieved by culturing, on the base matrix, the cells capable of producing such extracellular matrix, and/or by treating the base matrix with solubilized components of the extracellular matrix and/or at least an active fraction of the conditioned media from the cells capable of producing such extracellular matrix. Combination of these approaches is also contemplated.

In another aspect, the invention provides a method of increasing survival and/or differentiation of target cells on a base matrix, the method comprising: creating a cell-made extracellular matrix on the base matrix to produce a modified base matrix and administering the target cells to the modified base matrix. In different embodiments of the invention, the matrices include, without limitations, those described above.

In another aspect, the invention provides a method of increasing survival and/or differentiation of target cells on a base matrix through providing a soluble formulation of the extracellular matrix or conditioned media to the apical surface of the cells to stimulate self-assembly and deposition of extracellular matrix and/or stimulation of mechanisms for cell survival and differentiation.

In further embodiments of the invention the base matrix may be a biological matrix, such as Bruch's membrane or a synthetic polymer based matrix.

The cells capable of producing the extracellular matrix are in different embodiments selected from corneal endothelial cells, RPE cells, human embryonic stem (ES) cells and any combinations thereof. In a preferred set of embodiments, the cells are corneal endothelial cells, including, without limitations, bovine corneal endothelial cells (BCE).

In different embodiments, the target cells suitable for the methods of the instant invention are selected from RPE cells, umbilical cells, placental cells, adult stem cells, human ES cells (or other embryonic stem cells), cells derived from human ES cells (e.g. RPE derived from ES cells, retinal progenitor cells), fetal RPE cells, adult iris pigment epithelial (IPE) cells, Schwann cells, and combinations thereof. The target cells may be derived from an autologous or an allogeneic source.

In another aspect, the invention provides a conditioned media from culturing the cells capable of producing the extracellular matrix. The cells capable of forming the extracellular matrix may be the cells as described above. In a preferred embodiment, the media is collected after the cells reach confluency.

In another aspect the invention provides an active fraction of the conditioned media, as described in the previous paragraph. The active fraction is characterized by the depletion of bioactive components having molecular weight less than 20 kD, preferably less than 30 kD, more preferably, less than 50 kD, more preferably, less than 70 kD, more preferably, less than 80 kD, more preferably, less than 90 kD, and most preferably, less than 100 kD. The active fraction may also be comprised of a combination of any of the above molecular weight fractions.

In yet another aspect, the invention provides a method of treating an eye disease associated with degradation of an in situ extracellular matrix in the eye; such treatment includes creating a modified base matrix and administering the target cells to the modified base matrix.

In different embodiments of this aspect of the invention, the modified base matrix is created according to any of the embodiments of the previous aspect of the invention. Further, the target cells are chosen as described in any of the embodiments of the previous aspects of the invention.

In yet another aspect, the invention provides a kit for improving survival and differentiation of target cells on a matrix. Generally, the kit includes at least an active fraction of the conditioned media or solubilized extracellular matrix according to any embodiments described herein. The kit may also include a base matrix. In another set of embodiments, the kit comprises a modified base matrix. Further, in any embodiments of this aspect of the invention, the target cells may be provided.

In a further aspect, the invention provides a method for making a conditioned medium. The method includes (i) obtaining a plurality of cells capable of forming a cell-made extracellular matrix; (ii) culturing the cells in a first medium for a period of time to form a second medium; and (iii) collecting the second medium thereby making the conditioned medium. In one embodiment, the first medium is free of serum. The cells can be selected from the group consisting of corneal endothelial cells, RPE cells, IPE cells, embryonic stem cells, bone marrow-derived stem cells, placental cells, and umbilical cells. Preferably, the cells are corneal endothelial cells, such as bovine corneal endothelial cells. The period of time can be 1-5 days, such as 2-4 days or 3 days.

The invention also provides a composition comprising, consisting essentially of, or consisting of a fraction of the aforementioned conditioned medium. In one embodiment, the fraction comprises, consists essentially of, or consists of molecules having MW of less than 3 kD. In another, the fraction comprises, consists essentially of, or consists of molecules having MW of less than 50 kD, e.g., 10-50 kD or 50 kD. In a preferred embodiment, the composition comprises, consists essentially of, or consists of a first faction and a second fraction of the medium, where (i) the first fraction composition comprises, consists essentially of, or consists of molecules having MW of less than 3 kD, and (ii) the second fraction composition comprises, consists essentially of, or consists of molecules having MW of 10-50 kD. For example, the fraction can comprise, consist essentially of, or consist of one or more proteins selected from those listed in Table 6 below. The just-described composition can be a pharmaceutical composition and contains a pharmaceutically acceptable carrier.

The above-described composition can be used for treating age-related macular degeneration (AMD). To that end, one can identify a subject in need of such treatment and administer to the subject an effective amount of the composition.

The above-described composition can also be used as a cell culture medium for use in storing, preserving, or inducing differentiation of cells or tissues. Accordingly, this invention also provides a packaging product containing the composition, a cell or a piece of tissue, and a container holding the composition. The cell can be selected from the group consisting of retinal pigment epithelial (RPE) cells, stem cells, and corneal cells. The tissue can be selected from the group consisting of RPE derived from precursor cells, RPE derived from human embryonic stem cells, RPE derived from iPSC stem cells, whole retinae, whole cornea, tissues, and neural tissues and organs. The cell can be in suspension or in a support matrix designed for cell delivery. The composition can be used at a temperature within the range of 0-40° C., such as 4-30° C. or 15-25° C. In one embodiment, the composition and the cell or tissue can be sealed in the container.

In any embodiment of this aspect of the invention, suitable non-limiting examples of the base matrices, the modified base matrices, and the target cells are those described in the other aspects of the invention.

BRIEF DESCRIPTION OF THE DRAWINGS

FIG. 18 shows change in cell viability after storage at room temperature using CM batch 58.

FIG. 19 shows change in live cells after storage at 4° C.

FIG. 20 shows change in live cells after storage at room temperature.

Postmortem clinical photographs showing subfoveal geographic atrophy before RPE seeding. CM vehicle: (B) Only a few dead cells (arrows) and cellular debris are present on the explant surface. (C) No cells are present on the Bruch's membrane surface. BCEC-CM: (E) RPE fully resurface Bruch's membrane in the area of geographic atrophy with a few very small defects (arrows). Localized areas of multilayering are present. Cell surfaces show abundant apical processes (inset). (F) In this field, cells resurfacing the BCEC-CM explant are predominantly bilayered. Cells directly on Bruch's membrane are small and tightly packed; flat cells appear to overlie the cells in contact with Bruch's membrane. (G) Flattened cell processes overlying cells on top of Bruch's membrane are indicated by arrowheads. The cell processes contain vesicles. CM vehicle ND, 0; BCEC-CM ND, 19.61±0.43. Scale bar: (E) 100 µm; (E, inset) 20 µm; (F) 50 µm; (G) 20 µm. Toluidine blue staining.

FIGS. 27A-G show paired explants from an 80-year-old male with intermediate-size drusen in the CM vehicle-cultured eye and intermediate and large drusen in the BCEC-CM-cultured eye, seeded with cultured adult RPE (isolated from a 70-year-old donor). CM vehicle: (A) Two drusen (closely clustered) were present in the macula (arrow and arrowhead, high magnification inset). The drusen are not easily visualized in these photomicrographs due to post mortem changes. (B) Very few large cells are observed on the explant surface (6 cells in this image field). Arrow points to a pair of very large, flat cells. (C) No cells are present on the surface of Bruch's membrane. BCEC-CM: (D) A cluster of drusen (arrow and high magnification inset) can be seen in the macula of the fellow eye. (E) The explant is fully resurfaced by a monolayer of cells that are highly variable in size. Some of the cells within the monolayer do not have intact cell membranes (cells that appear white in the low magnification image), and some cells have died with remnants of cellular debris (arrows). The high magnification inset shows that most of the cells are covered with short apical processes, including cells that are very large (fetal RPE that are of this size on submacular Bruch's membrane generally have smooth surfaces with no apical processes). One cell in the field exhibits surface blebs. (F, G) Cells resurfacing the explant are generally large and often pigmented. Localized areas of bilayering are present (F, arrowheads). CM vehicle ND, 0.14±0.14; BCEC-CM ND, 12.0±0.77. Scale bar: (E) 100 µm; (E, inset) 20 µm; (F) 50 µm; (G) 20 µm. Toluidine blue staining.

Figure 28:
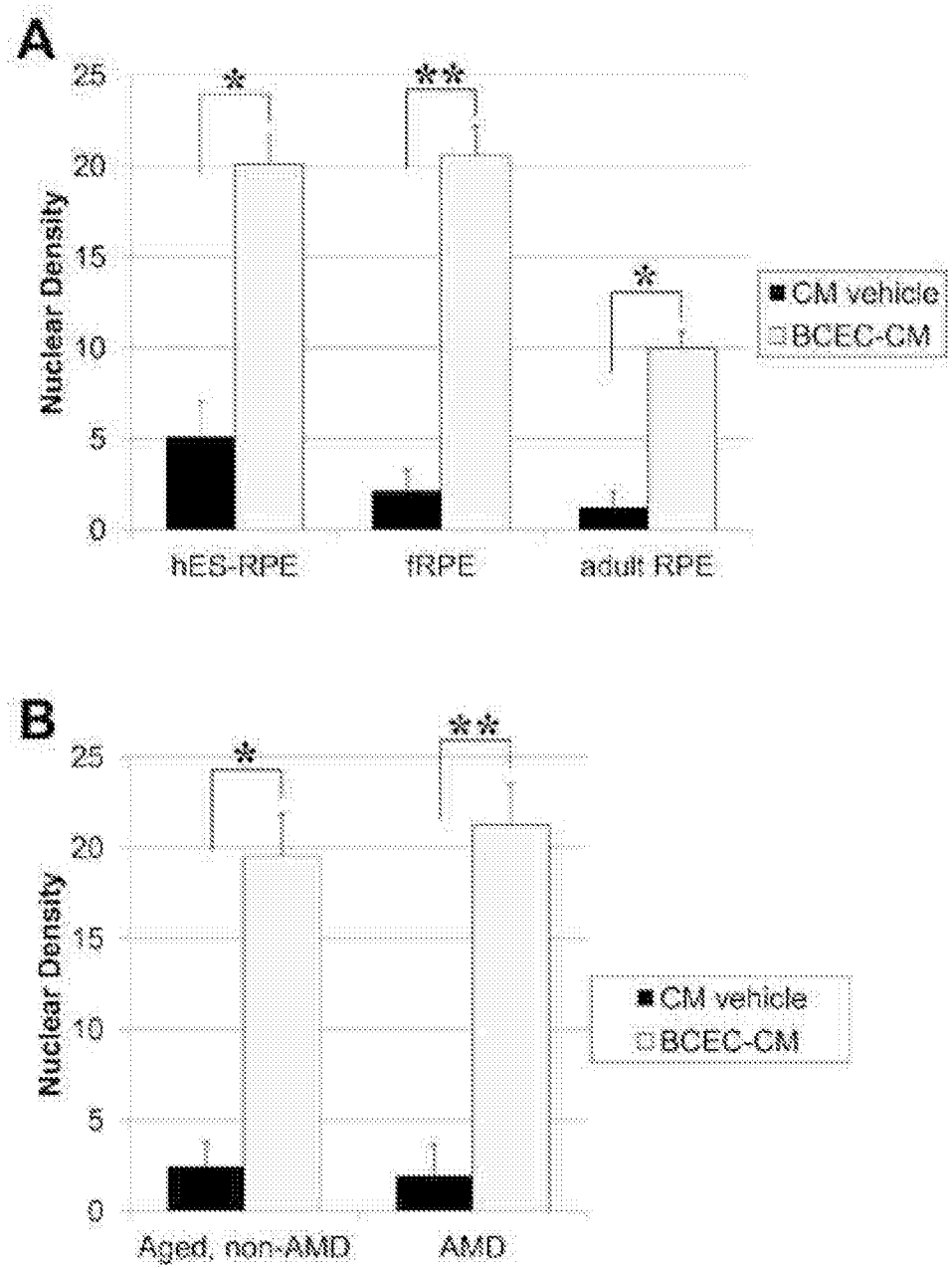

FIGS. 28A-B show nuclear densities of cells seeded on aged submacular Bruch's membrane explants after 21-day culture in conditioned medium vehicle (CM vehicle) or BCEC-conditioned medium (BCEC-CM) (paired explants from the same donor). (A) Nuclear density comparison of RPE derived from human embryonic stem cells (hES-RPE, N=6), cultured human fetal RPE (fRPE, N=22), and cultured human adult RPE (RPE donor ages 58, 71, 78 years; N=7). Within each group, significant differences were observed between cells cultured in CM vehicle and cells cultured in BCEC-CM. The nuclear density of cells cultured in CM vehicle was not statistically different between groups. The nuclear densities of hES-RPE and fRPE were not significantly different from each other but were significantly higher than the nuclear density of adult RPE after culture in BCEC-CM. (B) Comparison of nuclear densities of fRPE on age-matched, non-AMD vs. AMD Bruch's membrane at day-21. Explants seeded with fRPE on aged Bruch's membrane (N=9) were compared to explants seeded on AMD submacular Bruch's membrane (N=13). No significant differences were observed in the nuclear densities of fRPE on non-AMD vs. AMD explants for a given medium although the nuclear density was significantly higher in the presence of BCEC-CM vs. CM vehicle. Nuclear density values are counts of nuclei of cells directly in contact with Bruch's membrane, expressed as mean nuclear density/mm Bruch's membrane. Bars are mean nuclear density±standard error. *P<0.05; **P<0.001.

Figure 29:
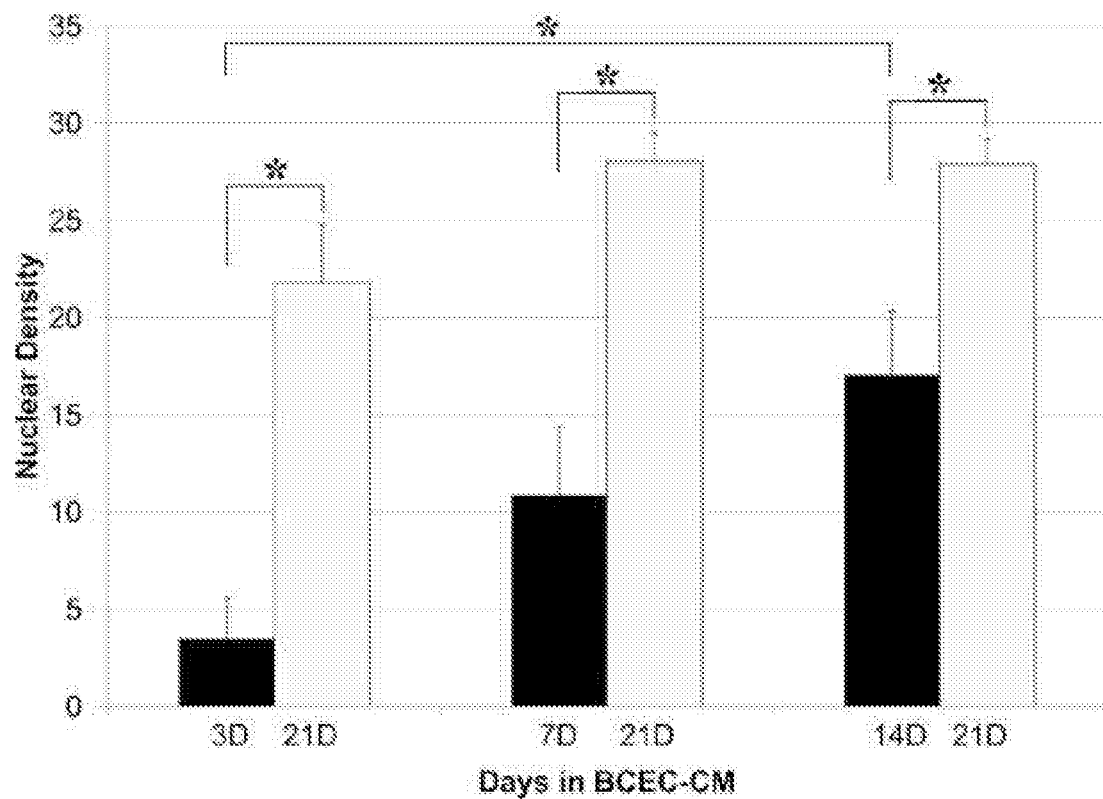

FIG. 29 shows nuclear densities of fetal RPE cultured in BCEC-CM for 3- (N=7), 7- (N=8) or 14-days (N=6) followed by culture in CM vehicle for a total culturing period of 21 days. Submacular Bruch's membrane explants from fellow eyes were cultured in BCEC-CM for the entire 21-day period. Nuclear densities were significantly higher when cultured for the entire 21-day period in BCEC-CM compared to shorter periods of time in BCEC-CM. Nuclear density after three-day culture was significantly lower than nuclear density after 14-day culture in BCEC-CM. Bars are mean nuclear density±standard error. *P<0.05.

Figure 30:
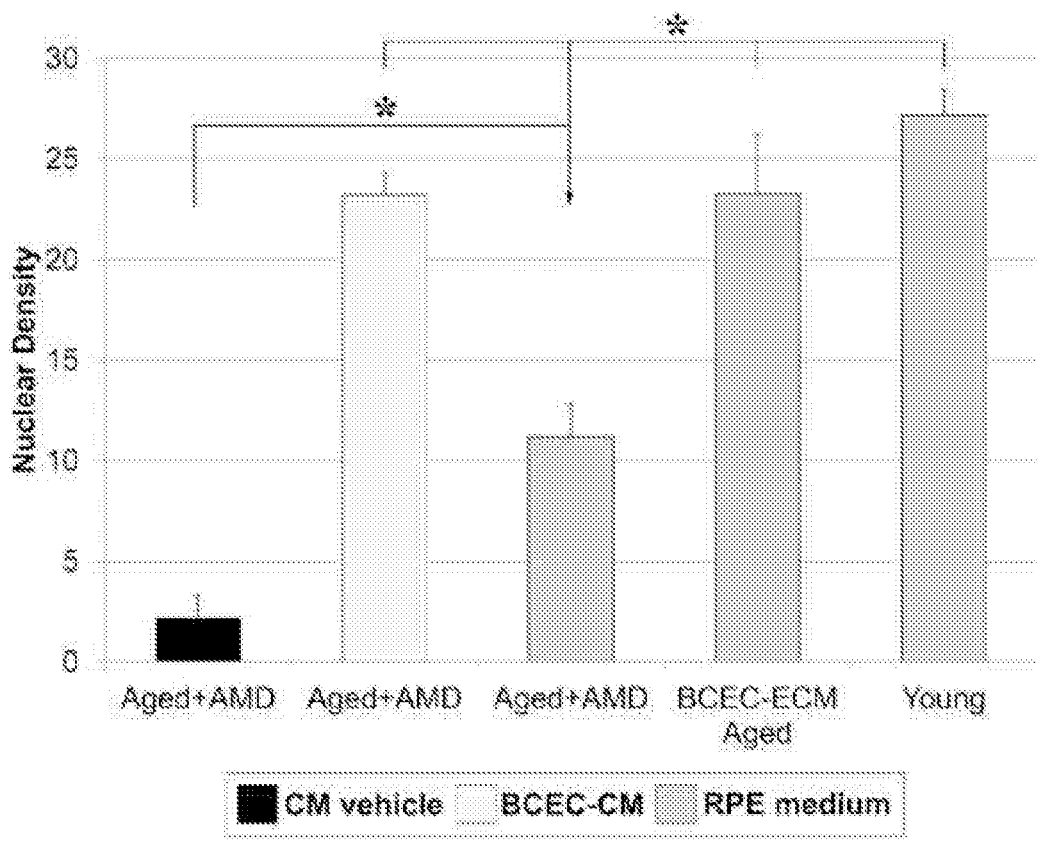

FIG. 30 shows comparison of fetal RPE nuclear density after 21-day culture in different media and on different surfaces. Nuclear densities of fetal RPE after culture in BCEC-CM on aged and AMD Bruch's membrane (N=43), BCEC-ECM-resurfaced aged Bruch's membrane cultured in RPE medium (N=11), and young Bruch's membrane cultured in RPE medium (N=5) were not significantly different. Culture on Bruch's membrane from aged and early AMD donors in RPE medium (N=33) resulted in significantly lower nuclear densities than that observed in BCEC-CM cultured, BCEC-ECM-resurfaced, and young Bruch's membrane explants. RPE nuclear density after culture in CM vehicle on aged and AMD Bruch's membrane (N=22) was significantly lower than culture in RPE medium on aged and early AMD explants. BCEC-CM explant nuclear densities are combined data from 21-day fetal RPE nuclear density counts of the Effects of BCEC-CM on Long-Term Cell Survival study (FIG. 28A) and 21-day BCEC-CM controls from the Cell Survival Following Different BCEC-CM Culture Times Study (FIG. 29). Data for BCEC-ECM resurfaced explants and young donor explants are from Sugino et al. *Invest Ophthalmol Vis Sci* 2011; 52:1345-1358. data for fetal RPE on aged (including early AMD) Bruch's membrane explants were combined data from Sugino et al. *Invest Ophthalmol Vis Sci* 2011; 52:4979-4997 and Sugino et al. *Invest Ophthalmol Vis Sci* 2011; 52:1345-1358 (data were not significantly different, P=0.745). Bars are mean nuclear density±standard error. *P<0.05.

FIGS. 31A-F show fetal RPE ECM deposition onto tissue culture dishes after 7-, 14-, and 21-day culture in BCEC-CM or RPE medium. ECM is deposited to a higher degree when cells are cultured in BCEC-CM (A-C) over the 21-day period compared to that observed after culture in RPE medium (D-F). Increase in the numbers of thick fibers can be seen in BCEC-CM culture with time while thick fiber deposition seems to be less extensive at all time points after culture in RPE medium. ECM coating of the tissue culture plastic is evident by the disappearance of the culture plastic striations (barely discernable in BCEC-CM cultures at day-7) at day-14 and -21. In RPE medium, culture plastic striations can be seen at day-7 and -14 but not at day-21, indicating that some material coats the culture dish. Scale bar, 50 µm; 0.1% Ponceau S stain, phase contrast.

FIGS. 32A-L show immunocytochemical labeling (epifluorescence) of collagen IV, laminin, and fibronectin deposition onto tissue culture dishes after 7-day culture in BCEC-CM or RPE medium. BCEC-CM: Collagen IV labeling (A) is visualized as a network of fibers with some thickened fibers and localized areas of continuous coating.

Laminin labeling (B, E) is similar of that of collagen IV although not as extensive. Laminin appears to colocalized with some collagen IV fibers (C, collagen IV, laminin overlay). Fibronectin labeling (D) is an open network of fibers with some areas of where fibers appear to have heavier deposition. Localized non-fibrous coating of the tissue culture dish can be seen adjacent to fibers. Fibronectin-laminin overlay (F) shows some co-localization of label. RPE medium: Collagen IV (A) labeling is more extensive than laminin (H, K). Very little fibronectin labeling (J) is present. Some co-localization of collagen and laminin is seen in the overlay (I). Labeling of all three ECM proteins is not as extensive as that seen after BCEC-CM culture (images for each protein photographed at same exposures). Scale bar, 200 µm.

Figure 32:
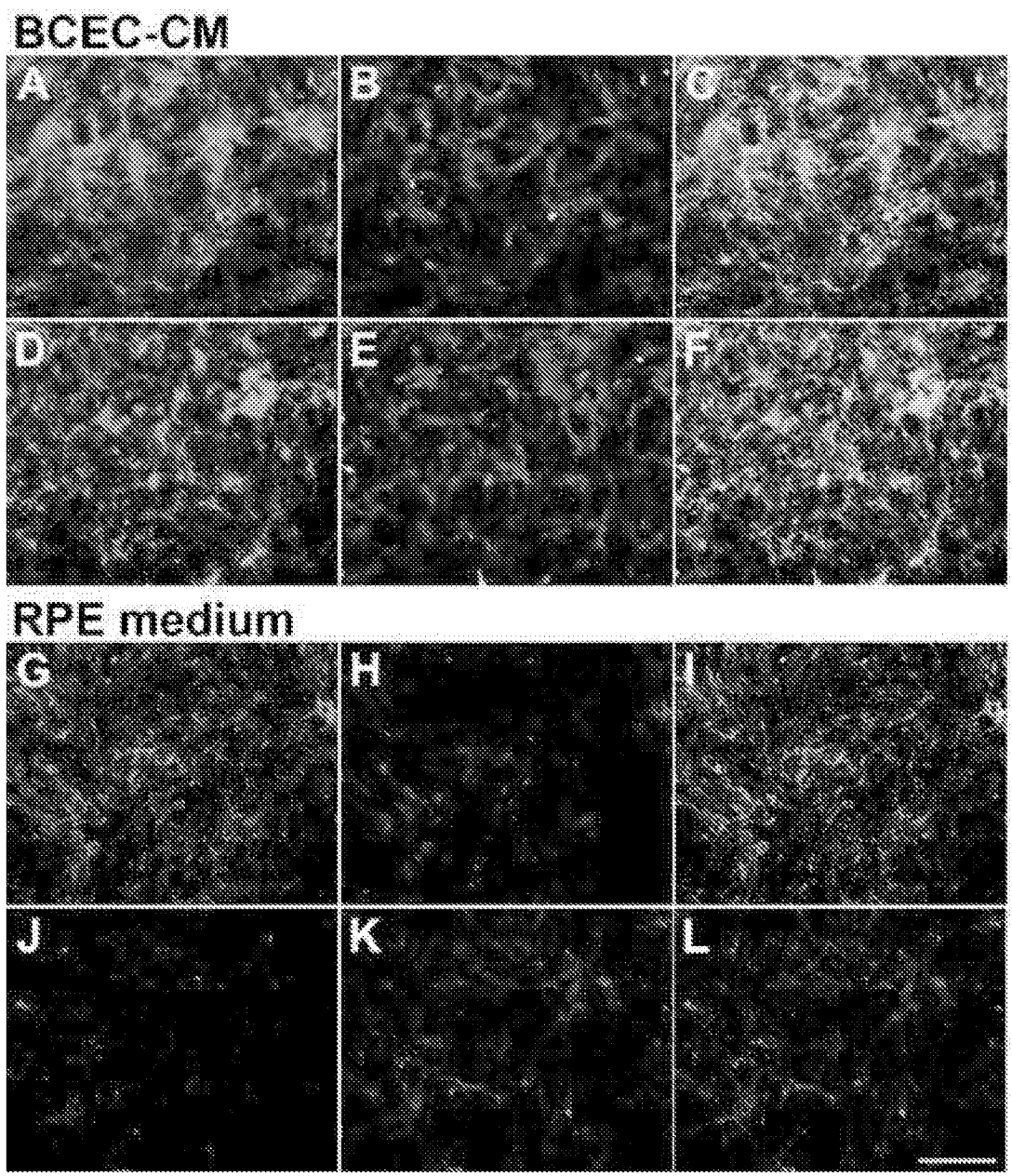

FIGS. 33A-L show immunocytochemical labeling (epifluorescence) of collagen IV, laminin, and fibronectin deposition onto tissue culture dishes after 14-day culture in BCEC-CM or RPE medium. BCEC-CM: Collagen IV (A), laminin (B, E) and fibronectin (D) deposition is more extensive than that seen at day-7 (FIG. 32). All three proteins show extensive resurfacing of the tissue culture dish with small defects in coverage. Collagen IV and laminin are highly co-localized (C) while fibronectin and laminin are co-localized in part (F). RPE medium: Collagen IV (G) and laminin (H, K) labeling are more extensive than at day-7 (FIG. 32) but are not as extensive as labeling seen after culture in BCEC-CM for the same time period. Very little fibronectin (J) is present. Images for each protein in the two conditions were photographed at the same exposure. Collagen IV and laminin are extensively co-localized (I) while fibronectin and laminin (L) are co-localized in part. (Intensity of fibronectin labeling has been increased for the overlay.) Scale bar, 200 µm.

FIGS. 34A-L show immunocytochemical labeling (epifluorescence) of collagen IV, laminin, and fibronectin deposition onto tissue culture dishes after 21-day culture in BCEC-CM or RPE medium. BCEC-CM: Similar to 14-day culture, collagen IV (A) and laminin (B, E) extensively resurface the culture dish and are highly co-localized (C). Fibronectin (D) does not appear to be as extensively deposited as collagen IV and laminin and is colocalized in part with laminin (F). RPE medium: Collagen IV (G) and laminin (H, K) appear to deposited at levels similar to those seen at day-14 and are not as extensive as that deposited after culture in BCEC-CM. Both proteins appear to be co-localized (I). Very little fibronectin was detected (J). Images for each protein in the two conditions were photographed at the same exposure. Scale bar, 200 µm.

FIGS. 35A-M show ECM deposition under fetal RPE on Bruch's membrane from a 70-year-old donor (no submacular pathology) after 21-day culture in BCEC-CM or RPE medium. BCEC-CM: (A) Calcein imaging of cells on Bruch's membrane prior to removal with ammonium hydroxide. The explant is resurfaced almost completely with small, highly fluorescent cells. Small defects are present in the RPE layer. (B) SEM of the surface of Bruch's membrane revealed after cell removal in an area where the ECM has been damaged (possibly at the time of cell removal or during confocal imaging manipulation), demonstrating the difference in surface morphology of the inner collagenous layer (ICL) vs. the newly deposited ECM. Arrows point to the folded edge of the ECM. (C) A network of open and fused fibers covered the surface of the ICL. The ECM forms a fairly continuous sheet in some areas. High magnification inset shows the ECM surface details. (D-F) Both collagen IV (D) and laminin (E) covered the explant with an extensive mesh-like deposition. There was some colocalization of label (F, overlay). (G) Control (no primary antibody, overlay) imaged at similar pinhole settings as (D) and (E) with higher detector gain in both FITC and rhodamine channels. Very little fluorescence is seen in either channel with some choroidal autofluorescence (FITC) seen in the upper left (arrow) of the image (tissue was not flat). (H-J) Fibronectin labeling (H) of ECM fibers was evident on the explant while laminin labeling (I), similar to that seen in (E), was seen in fibers, between fibers, and as punctate labeling associated with fibers. (Punctate laminin labeling shows up best in the overlay (J)). Fibronectin and laminin did not appear to be co-localized to any significant degree (J, overlay). (K) Control (no primary or secondary antibodies, overlay) imaged at the same settings as H-J. Only faint autofluorescence could be detected. RPE medium: (L) Calcein imaging of the explant shows cells resurfaced Bruch's membrane with several small defects in the RPE layer (arrows point to small RPE defects in the submacular area and a large defect on one edge (asterisk). Photographed at the same intensity settings as (A), the overall intensity of calcein imaging appears to be less than on (A) except at the edge of the large defect. (M) SEM examination of the surface of this explant revealed no ECM deposition confirming negative labeling (not shown) of all three markers by confocal examination. Collagen fibers are partially obscured by deposits. (A, L) epifluorescence; (B, C, M) SEM; (D-K) confocal compressed z-stacks. SEM scale bar, 10 µm; inset (C), 5 µm. Confocal scale bar, 50 µm.

DETAILED DESCRIPTION

In order to alleviate the drawbacks of the prior art, cell-based therapy may offer advantages over pharmacological therapy. Cell-based therapy to replace lost or diseased RPE has the potential to preserve and restore vision in: 1) age-related macular degeneration (AMD) patients with evolving atrophy and/or choroidal neovascularization, 2) patients suffering from traumatic RPE-Bruch's membrane injury, and 3) patients with other diseases associated with RPE dysfunction (e.g., Stargardt disease and some forms of retinitis pigmentosa). In addition to replacing lost or diseased RPE with cells capable of performing RPE functions, transplanted RPE may be able to rescue nearby dying photoreceptors through their known capacity to secrete substances such as neurotrophic factors and cytokines.

As noted above, pharmacological therapy involves administration of a finite number of compounds and usually involves fluctuations in drug levels above and below the desired level. In contrast, cells placed in situ express a plethora of molecules (e.g., neurotrophic factors, cytokines) that can inhibit pathological processes and rescue neurons that are damaged by disease. Moreover, they can express these molecules in amounts, combinations, and frequencies that are tailored precisely to molecular changes that occur from moment to moment. Thus, cells have the capacity to function as "factories" that produce many more substances at appropriate doses and times than can be managed with conventional pharmacological therapy. This pharmacological salutary capacity of cell-based therapy is termed "rescue".

Another capacity of cell-based therapy is "replacement," which refers to the ability of transplanted cells to replace native cells that have died. In diseases such as AMD, RPE and photoreceptor cell death constitutes a component of "irreversible" visual loss in many patients. Among AMD patients with evolving atrophy, RPE transplantation could be curative.

The first efforts to develop cell-based therapy for AMD involved RPE transplantation after CNV excision. Before current pharmacological therapy was available, CNV excision was proposed as a treatment for CNVs. In most AMD patients, CNV excision is associated with iatrogenic RPE defects due to the intimate association of RPE cells and the CNV. Combined RPE transplantation and CNV excision has been attempted in AMD eyes, but it has not yet led to significant visual improvement in most patients. In contrast, RPE transplantation in animal models of retinal degeneration has been proved to rescue photoreceptors and preserve visual acuity. Although animal studies validate cell transplantation as a means of achieving photoreceptor rescue, an important distinction between humans with AMD and laboratory animals in which RPE transplantation has been successful is the age-related modification of Bruch's membrane in human eyes, which may have a significant effect on RPE graft survival.

With normal aging, human Bruch's membrane, especially in the submacular region, undergoes numerous changes (e.g., increased thickness, deposition of extracellular matrix (ECM) and lipids, cross-linking of protein, non-enzymatic formation of advanced glycation end products). These changes and additional changes due to AMD could decrease the bioavailability of ECM ligands (e.g., laminin, fibronectin, and collagen IV) and cause the poor survival of RPE cells in eyes with AMD. Thus, although human RPE cells express the integrins needed to attach to these ECM molecules, long-term transplanted RPE cell survival on aged submacular human Bruch's membrane is impaired.

Because the changes in Bruch's membrane from aging and AMD are complex and may not be fully reversible, one approach is to establish a new ECM over Bruch's membrane. Adding exogenous ECM ligands (e.g., combinations of laminin, fibronectin, vitronectin, and collagen IV) can improve RPE attachment to aged Bruch's membrane to a limited degree. (Del Piore et al., *Curr Eye Res.* 2002; 25:79-89). These results are consistent with the hypotheses that ECM ligand availability may decrease with Bruch's membrane aging and that it is possible to increase ligand density on this surface.

It is doubtful that attention to individual ECM ligands without attention to their 3-dimensional organization will be highly effective (as indicated by the results of previous studies). The instant disclosure demonstrates that bovine corneal endothelial cells (BCE) can attach to Bruch's membrane and, more importantly, lay down ECM. Thus, Bruch's membrane can be resurfaced with a complex ECM that is known to support excellent RPE growth and differentiation and that is well-defined biologically (Tseng et al., *J Biol Chem.* 1981; 256:3361-5; Gospodarowitz et al, *J Cell Physiol.* 1983; 114:191-202; Robinson et al., *J Cell Physiol.* 1983; 117:368-76; Nevo et al., *Connect Tissue Res.* 1984; 13:45-57; Sawada et al., *Exp Cell Res.* 1987; 171:94-109; Kay et al., *Invest Ophthalmol Vis Sci.* 1988; 29:200-7).

The inventors have surprisingly found that RPE focal adhesion formation on aged submacular Bruch's membrane is abnormal compared to that seen on BCE-ECM-coated culture dishes. Without wishing to be bound by any particular theory, the inventors hypothesized that this early event, probably resulting from poor ECM ligand availability, underlies later degenerative changes in RPE cells on aged Bruch's membrane after they attach. RPE focal adhesion formation is markedly improved on BCE-ECM-coated aged submacular Bruch's membrane six hours after seeding. RPE cells seeded onto the BCE-ECM-coated Bruch's membrane uniformly resurface the submacular explants with small, compact cells of variable shape. As discussed in the examples, the inventors' data demonstrate that resurfacing by BCE-ECM enhances RPE cell long-term survival on aged submacular human Bruch's membrane by ~230% (see FIG. 2A-C and FIG. 3), which is in marked contrast to previous studies in which only modest improvement was seen following treatment with soluble ECM ligands. RPE long-term survival and differentiation are enhanced via this approach.

The research described in the instant application has demonstrated that survival of transplanted cells depends critically on the surface on which the transplanted cells grow. In two animal models, allogeneic RPE transplants can survive for at least short periods of time in the subretinal space and that freshly harvested RPE sheets or microaggregates are similarly successful. (Wang et al., *Invest Ophthalmol Vis Sci.* 2001; 42:2990-9; Wang et al., *Exp Eye Res.* 2004; 78:53-65). In pigs, there is more inflammation associated with freshly harvested sheets than with cultured dispersed cell transplants, possibly due to the greater trauma associated with sheet transplantation.

AMD-related changes as well as iatrogenic changes associated with choroidal new vessel (CNV) excision create a damaged Bruch's membrane surface in eyes undergoing CNV excision. (Nasir et al., Brit. J. Ophthalmol. 1997; 81:481-9; Zarbin, Arch Ophthalmol. 2004; 122:598-614). In most cases, surgical damage to Bruch's membrane includes removal of the RPE basement membrane and removal of portions of the inner collagenous layer (ICL). Aged adult RPE can resurface RPE defects on aged submacular human Bruch's membrane in organ culture only to a limited extent. (Wang et al., Invest Ophthalmol Vis Sci. 2003; 44:2199-2210) In addition to the surface affecting the ability of aged adult RPE to resurface RPE defects, aged RPE per se are impaired in their ability to attach and grow in culture and on Bruch's membrane. (Tsukahara et al., Exp Eye Res 2002; 74(2):255-266; Zarbin. Trans Am Ophthalmol Soc 2003; 101:499-519; Wang, et al., J Rehabil Res Dev 2006; 43: 713-22; Ishida, et al., Curr Eye Res. 1998; 17: 392-402).

Resurfacing is even more limited if RPE migration/ingrowth must occur on the ICL. The in vitro wound healing data accurately predict the outcome in AMD patients following CNV removal, who show incomplete ingrowth of RPE with associated photoreceptor degeneration. (Hsu et al., *Retina.* 1995; 15:43-52). Freshly harvested, aged adult RPE cells, such as would be used in autologous transplants, do not survive on aged submacular Bruchs membrane. (Tsukahara et al., *Exp Eye Res.* 2002; 74:255-66). Culturing adult RPE cells upregulates integrins necessary for cell attachment. (Zarbin, *Trans Am Ophthalmol Soc.* 2003; 101:499-520). However, aged adult RPE never grow as robustly on aged Bruch's membrane as young RPE. Histopathology of an AMD eye that underwent uncultured adult RPE transplantation confirms these predictions. (Del Priore et al., *Am J Ophthalmol.* 2001; 131:472-80).

Long-term studies of cultured fetal human RPE on aged submacular human Bruch's membrane show that many cells do not survive, and if they are present, they do not appear to be adequately differentiated. (Gullapalli et al., *Exp Eye Res.* 2005; 80:235-48). Of the various cell types studied to date (including adult stem cells, embryonic stem cells (differentiated into RPE-like cells), adult and fetal RPE, and adult iris pigment epithelial (IPE) cells), none appear to survive and differentiate adequately on aged submacular human Bruch's membrane. (Zarbin et al., 2003; Gullapalli et al., 2005; Gullapalli et al., *Trans Am Ophthalmol Soc.* 2004; 102:123-37; discussion 137-8; Itaya et al., *Invest Ophthalmol Vis Sci.* 2004; 45:4520-8).

Thus, in one aspect, the invention is drawn to a modified base matrix for survival and/or differentiation of RPE cells thereon, the modified base matrix comprising a cell-made extracellular matrix thereon.

In different embodiments, the base matrices suitable for the instant invention may be protein-based matrices, including, without limitations, collagen (including gelatin), solubilized human basement membrane, and fibrinogen-based formulations. These synthetic matrices can include mixtures optimized according to concentration of base formulations and additional cell-supporting molecules added to said formulations.

In other embodiments, the base matrices may comprise non-proteinaceous polymers, such as, for example, polycaprolactone (PCL), polylactic acid (PLA), polyglycolic acid (PGA), poly(lactide-co-glycolide) (PLGA), poly(methyl methacrylate) (PMMA), polyorthoester matrices, and any combinations thereof.

In yet another set of embodiments, the base matrices may be biological membranes, such as, for example a Bruch's membrane. In one embodiment, the Bruch's membrane used as a base matrix of the instant invention is an aged Bruch's membrane. The term "aged" essentially depends on a species source of the membrane used (e.g., assuming that the source of the membrane is human, the membrane over 40 years old, or 50 years old, or 60 years old, or 70 years old, or 80 years old, or 90 years old, or 100 years old). The species source of the Bruch's membrane include, without limitations primates, e.g., gorilla, chimpanzee, orangutan, and human. If the source of the membrane is not human, the age of the membrane should be adjusted accordingly, based on the life span of the source species.

The matrices described and/or exemplified in any of the embodiments of the invention may be located in vivo or in vitro.

The methods of production of the base templates depend on the nature of the template. For example, if the template is polymer-based (e.g., PCL based), it may be chemically synthesized. If the template is a biological membrane, as described above, it can be surgically harvested and cultured according to the methods known in the art, including, without limitations, those described in the Examples below.

Once the base matrix is chosen and obtained, it is modified with an extracellular cell-made matrix to produce a modified base matrix. The suitable cells capable of forming matrices are well known in the art and include, without limitations corneal endothelial cells (including, but not limited to, bovine cells), RPE cells (including, but not limited to, human), IPE cells (including, but not limited to, human), and stem cells (including, but not limited to, human embryonic stem cells, placental stem cells, umbilical stem cells, bone marrow-derived stem cells, neural progenitor cells).

The choice of the cells capable of forming the extracellular cell-made matrices ultimately depends on the nature of target cells that are to be grown on the modified base matrix. In a set of embodiments, wherein the target cells that are grown on the modified base matrix are RPE, corneal endothelial cells, e.g., bovine corneal endothelial cells (BCE) present a suitable option.

Another aspect of the invention is the application of conditioned media. It may be applied in one of three ways: 1) as a modification of the base matrix, 2) as a solution or in a biocompatible and degradable matrix applied to the apical surface of transplanted cells, or 3) as part of the vehicle in which the cells are transplanted.

The methods of culturing BCE cells are well known in the art although specifics of the methods may vary slightly (see, e.g., Bonanno et al., *Am J Physiol Cell Physiol* 277: C545-C553, 1999; Tseng et al., *J. Cell Biol* 1983; 97:803-809; Katz, et al, Invest Ophthal Vis Sci 1994; 35:495-502; Gospodarowicz, et al., Exp Eye Res 1977; 1:75-89; MacCallum et al., Exp Cell Res 1982; 139:1-13; Vlodaysky Curr Protocols Cell Biol 1999; 10.4.1-10.4.14. Briefly, according to the protocol published by Bonanno, the primary cultures from fresh cow eyes are established in T-25 flasks with 3 ml of DMEM, 10% bovine calf serum, and an antibiotic-antimycotic (100 U/ml penicillin, 100 µg/ml streptomycin, and 0.25 µg/ml Fungizone); gassed with 5% $CO_2$-95% air at 37° C., and media changed every 2-3 days. These are subcultured to three T-25 flasks and grown to confluence in 5-7 days. The resulting second-passage cultures are then subcultured onto coverslips or filters, reaching confluence within 5-7 days.

Another method of culturing BCE is to establish freshly isolated cells on tissue culture dishes (diameter 35, 60, or 100 mm) in Dulbecco's modified Eagle's medium (DMEM) supplemented with RPE complete media (DMEM with 2 mM glutamine, 15% fetal bovine serum, 2.5 µg/ml fungizone, 0.05 mg/ml gentamicin, 1 ng/ml basic fibroblast growth factor (bFGF)). Cells are grown in a humidified incubator at 10% $CO_2$-95% air at 37° C. until confluent with media change every 2-3 days. Upon confluency, cells are passaged at a split ratio of ~1:3.7. First passage cells are grown in RPE complete media until confluent; second passage cells are generated by passaging first passage cells at a split ratio of ~1:7.3.

ECM can be generated by culturing (including but not limited to) first, second, or fourth passage cells in ECM media (DMEM with 2 mM glutamine, 10% fetal bovine serum, 5% donor calf serum, 2.5 µg/ml fungizone, 0.05 mg/ml gentamicin, 1 ng/ml bFGF, 4% dextran). 1 ng bFGF is added every 2-3 days until cells are confluent. ECM can be harvested from cells at confluence or up to 3 months post-confluency. Time of ECM harvesting is specific to the cell depositing ECM. (BCE require less time to deposit ECM than RPE, including RPE derived from human ES.) Cells can be removed for ECM harvesting by exposure to 0.02M $NH_4OH$ and/or PBS and/or detergents (e.g., 0.5% triton X-100) and/or urea (2M).

Conditioned media is generated by growing cells following passage in maintenance media (ECM media without dextran). bFGF may or may not be added every 2-3 days. 48-72 hours prior to collection, cells are washed a minimum of 3× in DMEM with no supplements to remove serum. Media is collected after 48-72 hour culturing in MDBK-MM or other base medium.

In different embodiments of the invention, the modified base matrix may generally be created by at least three techniques: first, the matrix-forming cells are cultured on the base matrix; second, the matrix is deposited by cells onto culture dishes and harvested; and third, the matrix-forming cells are cultured separately from the base matrix, and the tissue culture media from the matrix-forming cells is collected. Harvested deposited ECM and/or media from culture may be administered to the base matrix, may be applied to the apical surface of cells, or may be used as a vehicle for cell transplantation. Apical application of the ECM and/or conditioned media can be by one of the following methods (including but not limited to): injection of the ECM and/or conditioned media solely or in a biocompatible, biodegradable matrix and/or injection following transplant cell attachment or placement onto Bruch's membrane; incorporated into the overlying material (e.g., gelatin) used for transplanting cell sheets or embedded single cells or cell aggregates. The combination of these techniques is also contemplated.

If the first or second option is employed, the matrix-formed cells may be stripped from the base matrix by chemical methods, such as, for example, NH$_4$OH or Urea or detergent wash or PBS soaking. Enzymatic methods (e.g., trypsin digestion) are less desirable due to possible protein damage.

If the third option is employed, it is important to keep in mind that serum, which may be present in the conditioned media, usually contains ligands of the cell-made (extracellular) matrix in the media. Accordingly, the suitable media should preferably be serum free, or at the very least, serum depleted to reduce the likelihood of inducing an inflammatory/immune response in the transplant recipient.

After sufficient time, e.g., at least 7 days or at least until cultures reach 100% confluency, or at least 1 week after confluency, or at least 2 weeks after confluency, or at least 3 months after confluency) the modified base matrix is formed to a degree sufficient to improve survival and differentiation of the cells which are to be grown on the modified base matrix (i.e., target cells). In other words, the sufficient time may be less than 3 months, or less than 2 weeks post-confluency, or less than 1 week post-confluency, or less than 7 days. As discussed above, the target cells may include, without limitations, RPE, umbilical cells, placental cells, adult stem cells, ES cells, bone marrow-derived stem cells, fetal RPEs, adult iris pigment epithelial (IPE) cells, neural progenitor cells, Schwann cells, and any combination thereof, and may be derived from an autologous or an allogeneic source.

In another aspect, the invention provides a method of increasing survival and/or differentiation of target cells on the base matrix, the method comprising: creating cell-made extracellular matrix on said base matrix to produce a modified base matrix and administering to said modified base matrix said target cells.

According to this aspect, the base matrix and the modified base matrix include, without limitations, the base matrices and the modified base matrices as described according to the previous aspect of the invention or as disclosed in the examples below.

The target cells include, without limitations, the target cells described above. In one embodiment, the cells are RPE. The RPE cells may be chosen or differentiated from multiple sources. For example, RPE may be differentiated from stem cells, such as embryonic or adult stem cells, or RPE may be fetal RPE. The methods of in vitro differentiation of RPE are known in the art.

For example, if one desires to differentiate the RPE from ES cells, US Publication 20070196919 discloses a suitable exemplary method for doing so. Briefly, the H-1 (WA-01) human embryonic stem cell line may be obtained from a commercial or a non-commercial source, such as Wicell Research Institute. The cells are cultured and passaged on a feeder layer made of irradiated mouse embryonic fibroblasts. Embryoid bodies are formed by treating undifferentiated hES colonies with 1 mg/ml of type IV collagenase (Invitrogen) and resuspending them in a 6-well ultra-low attachment plate (VWR) in the presence of media containing DMEM:F12 (Gibco), 10% knockout serum (Invitrogen), B-27 supplement (Invitrogen), 1 ng/ml mouse noggin (R&D Systems), 1 ng/ml human recombinant Dkk-1 (R&D Systems), and 5 ng/ml human recombinant insulin-like growth factor-1 (IGF-1) (R&D Systems). The cells are cultured as embryoid bodies for 3 days. On the fourth day, the embryoid bodies are plated onto poly-D-lysine-Matrigel (Collaborative Research, Inc)-coated plates and cultured in the presence of DMEM: F12, B-27 supplement, N-2 Supplement (Invitrogen), 10 ng/ml mouse noggin, 10 ng/ml human recombinant Dkk-1, 10 ng/ml human recombinant IGF-1, and 5 ng/ml human recombinant basic fibroblast growth factor (bFGF) (R&D Systems). The media is changed every 2-3 days.

Adult cells may also be used for creating RPE cells. For instance, retinal and corneal stem cells themselves may be utilized for cell replacement therapy in the eye. In addition, neural stem cells from the hippocampus have been reported to integrate with the host retina, adopting certain neural and glial characteristics (see review of Lund, R. L. et al., 2003, *J. Leukocyte Biol.* 74: 151-160). Neural stem cells prepared from fetal rat cortex were shown to differentiate along an RPE cell pathway following transplantation into the adult rat subretinal space (Enzmann, V. et al., 2003, *Investig. Ophthalmol. Visual Sci.* 44: 5417-5422). Bone marrow stem cells have been reported to differentiate into retinal neural cells and photoreceptors following transplantation into host retinas (Tomita, M. et al., 2002, Stem Cells 20: 279-283; Kicic, A. et al., 2003, *J. Neurosci.* 23: 7742-7749). An ocular surface reconstruction in a rabbit model system, utilizing cultured mucosal epithelial stem cells, has also been reported.

In other embodiments, other cell types may be used for the methods of the instant invention. For example, US Publication 20050037491 (the '491 publication) reports that placental or umbilical cells injected into an eye of a dystrophic RCS rat differentiate into cells exhibiting at least some RPE characteristics, as assessed by ERG recording, rod and cone responses, a- and b-wave recording, histological examination, and Nissl staining.

In the experiments of the '491 publication, cultures of human adult umbilical and placental cells (passage-10) were expanded for 1 passage. All cells were initially seeded at 5,000 cells/cm$^2$ on gelatin-coated T75 flasks in Growth Medium. For subsequent passages, all cells were treated as follows. After trypsinization, viable cells were counted after trypan blue staining. Briefly, 50 microliters of cell suspension was combined with 50 microliters of 0.04% w/v trypan blue (Sigma, St. Louis Mo.), and the viable cell number, was estimated using a hemocytometer. Cells were trypsinized and washed three times in supplement free-DMEM:Low glucose medium (Invitrogen, Carlsbad, Calif.). Cultures of human umbilical placental and fibroblast cells at passage-11 were trypsinized and washed twice in Leibovitz's L-15 medium (Invitrogen, Carlsbad, Calif.). For the transplantation procedure, dystrophic RCS rats were anesthetized with xylazine-ketamine (1 mg/kg i.p. of the following mixture: 2.5 ml xylazine at 20 mg/ml, 5 ml ketamine at 100 mg/ml, and 0.5 ml distilled water), and their heads secured by a nose bar. Cells devoid of serum were resuspended ($2 \times 10^5$ cells per injection) in 2 microliters of Leibovitz, L-15 medium (Invitrogen, Carlsbad, Calif.) and transplanted using a fine glass pipette (internal diameter 75-150 micrometers) transsclerally. Cells were delivered into the dorso-temporal subretinal space of anesthetized 3-week old dystrophic-pigmented RCS rats (total N=10/cell type).

As discussed throughout this disclosure, treatment of the base matrix with a conditioned media from BCE cells is sufficient for improved survival and/or differentiation of the target cells. Accordingly, in another aspect, the invention provides a conditioned media from cultured cells capable of producing the cell-made matrix, according to any embodiment, as described above. In addition, the inventors have surprisingly discovered that experiments with media harvested from passage-2 cultures show that media harvested from cells that have been in culture for 2 weeks after reaching confluency is not as supportive as media harvested at earlier time points (50% confluent, confluent, 1 week after confluency). Thus, in a preferred embodiment, the conditioned culture medium is harvested from the cells that have not been confluent for more than 2 weeks.

The inventors have also discovered that the whole conditioned media is not necessary for the improved survival and/or differentiation of the RPE on the modified base matrix. Thus, in another aspect, the invention is drawn to the active fraction of the conditioned culture media, according to any of the embodiments described above. Specifically, the inventors have found that high molecular weight components are sufficient for the initial beneficial effect of the conditioned culture media. Specifically, such an active fraction may be characterized by having its low molecular weight components depleted. However, low molecular weight components may be important in long-term survival and differentiation.

In different embodiments, the active fraction is characterized by the depletion of bioactive components having molecular weight less than 20 kD, preferably less than 30 kD, more preferably, less than 50 kD, more preferably, less than 70 kD, more preferably, less than 80 kD, more preferably, less than 90 kD, and most preferably, less than 100 kD. The active fraction may be characterized by any combination of components separated according to size or other methods (e.g., high pressure liquid chromatography (HPLC)).

The depletion of low molecular weight or other nonessential components may be achieved by many methods, including, without limitation, filtration, size fractionation by gel filtration or gradient centrifugation, HPLC (separation according to charge, size, or hydrophobicity), immunoprecipitation, affinity column separation, and the like. However, it is important that the methods of depletion of low-molecular weight compounds should not result in protein cleavage nor should it disrupt secondary and tertiary protein structures of any needed components in the medium.

While it is possible to surgically remove CNVs, CNV excision is associated with iatrogenic RPE defects due to the intimate association of RPE cells and the CNV. (Thomas et al., *Am J Ophthalmol* 1991; 111:1-7; Nasir et al., *Br J Ophthalmol* 1997; 81:481-489; Castellarin et al., *Retina* 1998; 18:143-149; Hsu et al., *Retina* 1995; 15:43-52; Rosa et al., *Arch Ophthalmol* 1996; 114:480-487). Combined RPE transplantation and CNV excision has been attempted in AMD eyes, but it has not led to significant visual improvement in most patients. (Algvere et al., *Graefes Arch Clin Exp Ophthalmol* 1994; 232:707-716; Del Priore et al., *Am J Ophthalmol* 2001; 131:472-480; Binder et al., *Am J Ophthalmol* 2002; 133:215-225; Tezel et al., *Am J Ophthalmol* 2007; 143:584-595; Joussen et al., *Am J Ophthalmol* 2006; 142:17-30). Potential causes of RPE transplant failure in human patients include immune rejection, inability of transplanted RPE cells to survive and differentiate on aged submacular Bruch's membrane, and choriocapillaris atrophy, all causing death of the RPE graft. In contrast, RPE transplants rescue photoreceptors and preserve visual acuity in animal models of retinal degeneration. (Li et al., *Exp Eye Res* 1988; 47:911-917; Coffey et al., *Exp Neurol* 1997; 146:1-9; Lund et al., *Proc Natl Acad Sci USA* 2001; 98:9942-9947; Wang et al., *Invest Ophthalmol Vis Sci* 2008; 49:416-421; Gias et al., *The European journal of neuroscience* 2007; 25:1940-1948).

An important distinction between humans with AMD and laboratory animals is the age-related modification of Bruch's membrane that occurs in human eyes. With normal aging, human Bruch's membrane, especially in the submacular region, undergoes numerous changes (e.g., increased thickness, deposition of extracellular matrix (ECM) and lipids, cross-linking of protein, nonenzymatic formation of advanced glycation end products). (Guymer et al., *Prog Retin Eye Res* 1999; Marshall et al., *The Retinal Pigment Epithelium*. New York: Oxford University Press; 1998:669-692; 18:59-90; Abdelsalam et al., *Surv Ophthalmol* 1999; 44:1-29). Pauleikhoff and coworkers reported an age-related decline in the presence of laminin, fibronectin, and collagen IV in the RPE basement membrane. (Pauleikhoff et al., *Ophthalmologe* 2000; 97:243-250). It is possible that changes in submacular Bruch's membrane permeability and choriocapillary density may contribute to age-related RPE death. However, it was found that RPE survival is also impaired on aged submacular Bruch's membrane explants in organ culture, where diffusion of nutrients is not a factor in cell survival. This finding suggests that there are additional factors within aged Bruch's membrane itself that adversely affect RPE survival and that modification of Bruch's membrane may have a significant effect on RPE graft survival in patients with AMD. (Gullapalli et al., *Exp Eye Res* 2002; 74:255-266).

As discussed above and shown in the examples below, in the instant invention, the use of modified base matrix according to any embodiment of the invention promotes survival and/or differentiation of cells transplanted onto this matrix. In embodiments where the base matrix is an aged Bruch's membrane or a Bruch's membrane from an eye undergoing macular degeneration, survival and/or differentiation of transplanted RPE was improved when the Bruch's membrane was modified with extracellular matrix from BCE cells. Importantly, the experiments were performed in human eyes, thus validating the methods and compounds of the instant invention for human treatment.

Accordingly, in one aspect, the methods according to the instant inventions may be performed for treatment of humans suffering from AMD (whether the wet AMD or the dry AMD). As mentioned above, retinal degenerative diseases constitute the leading causes of blindness in the industrialized world. AMD, the most prevalent of these, can be treated pharmacologically, although at this time the majority of patients do not recover lost vision. RPE cells may be a primary target of the pathological processes that cause AMD.

The goal of cell-based therapy as a treatment for AMD patients is to replace diseased or dying RPE cells, which provide metabolic support for the photoreceptors. RPE transplantation could prevent further vision loss and might even, in some cases, lead to vision improvement in selected AMD patients. Cell-based therapy in AMD patients has not reached its full potential due to the failure of cells to survive and become functional in the diseased AMD eye.

As disclose herein, the present invention provides a biologically synthesized mixture (bovine corneal endothelial cell-conditioned media, BCEC-CM) that improves transplanted RPE survival by more than 10-fold when tested in an organ culture bioassay utilizing aged and AMD human donor eyes. It was found that BCEC-CM significantly improved cell survival on aged and AMD Bruch's membrane (the surface on which cells must survival in patients)

using fetal RPE, aged adult RPE, and RPE generated from human embryonic stem cells. Identification of the bioactive molecules in BCEC-CM allows for the development of an adjunct to cell transplantation therapy in patients with AMD to ensure successful cell transplant integration and functionality.

In one embodiment, the present invention provides BCEC-CM and conditioned media comprising bioactive molecules derived therefrom for therapeutic use in AMD. Specifically, it provides fractions of BCEC-CM identified via molecular cut filtration possessing bioactivity, one in the <3 kDa filtrate and one found in a 10-50 kDa fraction. These fractions, in combination, ensure cell survival on Bruch's membrane. The bioactive molecule or molecules in each of these fractions in BCEC-CM can serve as an adjunct to cell transplantation therapy in patients with AMD.

In other embodiments, the methods of treatment comprise modifying Bruch's membrane with the cell made extracellular matrix, according to any embodiments described herein, and wherein the Bruch's membrane is located in vivo. Essentially, in different embodiments, Bruch's membrane is modified when the at least the active fraction of the conditioned media (or the whole conditioned media) of any of the embodiments described above or exemplified below can be applied basally as a substrate to coat the surface of Bruch's membrane, in a mixture with cells, or apically in a biocompatible matrix.

It is also worth noting that this invention has been shown to support adult and embryonic stem cells and retinal pigment epithelial cells (adult and fetal) on human Bruch's membrane, including Bruch's membrane from AMD eyes. Accordingly, in different embodiments, different types of cells may be applied within the methods of this aspect of the invention.

The compositions containing the extracellular matrix (e.g., at least the active fraction of the conditioned media according to any embodiment of the instant invention) can be applied to Bruch's membrane in living patients through a variety of strategies, e.g., direct application to the subretinal space.

In another embodiment, the scaffold (i.e., the base matrix), such as, for example, a polymeric scaffold such as PCL, can be delivered into the subretinal space. In different embodiments, the scaffold is modified with the extracellular matrix (resulting in the modified base matrix, as described above and exemplified below. Further, such modified base matrix may be delivered in combination with a scaffold that contains cells to be transplanted to the patient's eye. The suitable cells have been described above.

As used herein, the terms "treat" or "treatment" or "treating" etc., refer to executing a protocol in an effort to alleviate signs or symptoms of a disease in a subject. Alleviation may occur either before or after appearance of these signs or symptoms. In addition, these terms do not require a complete alleviation of the signs or symptoms, do not require a cure, and include protocols resulting in only marginal effects on a patient.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

In another aspect, the invention provides a kit for treatment of AMD (both wet AMD and dry AMD). Generally, the kit would include a set of instructions and at least the active fraction of the conditioned media, as described in any of the embodiments of the instant invention, and may comprise the unfractionated conditioned media, also, according to any of the embodiments of the instant invention. Alternatively, the kit may comprise the cells capable of producing the cell-made extracellular matrix, according to any of the embodiments of the instant invention. Specifically and without limitations, the cells capable of producing the cell-made extracellular matrix include BCE cells. Alternatively, the kit may include ECM generated and harvested from cell-deposited matrices in solubilized or non-solubilized form.

Optionally, the kit may provide the base matrix, according to the embodiments described above. The base matrix may be a natural polymer (e.g., a protein-based base matrix), a synthetic polymer (e.g., PCL), a biological membrane (e.g., Bruch's membrane), or a combination thereof.

In another set of embodiments, the kit may comprise a modified base matrix, according to any of the embodiments described herein. In any of the embodiments of the kit, suitable target cells may also be provided, according to any of the embodiments described above.

The set of instructions may be provided in any media, including, without limitations, written, graphic, audio recording, video recording, and electronic media.

In yet another aspect, the invention provides a novel medium for and method of storing and differentiating cells for transplantation. Cell-based therapy represents a promising approach, which may be sight-preserving and/or restoring for patients with these diseases. However, cell-based therapies are complicated by the necessary step of growing, differentiating and storing cells for transplantation. Given the severe consequences of AMD and the often irreversible vision loss which may occur, there exists a need for specifically-designed and improved methods of preparing cells for transplantation.

The present invention provides a novel medium for and method of differentiating, storing and preserving cells for transplantation. The medium was developed as a measure to improve the viability and functionality of cells or tissues, prior to transplantation. It can be used with various types of cells and tissues, including, but not limited to, ocular cells, ocular tissue and neural tissue. One application of the medium is the storage and shipment from cell manufacturer to an end user (e.g., surgeon). The medium can further serve as a cell culture medium, to induce rapid differentiation of RPE cells, as well as other cells and tissues. Accordingly, this invention provides a novel medium for storage and differentiation which provides the significant advantage of improving the health and functionality of cells, tissues or organs, at the time of transplantation.

In one embodiment, the present invention provides a storage and preservation medium for use prior to transplantation of various biological transplants, including, but not limited to, cells, retinal pigment epithelial (RPE) cells, RPE derived from various cells, RPE derived from human embryonic stem cells, RPE derived from iPSC stem cells for neurodegenerative diseases, corneal cells, whole retinae, whole cornea, tissues, neural tissues and organs. This medium will support RPE viability during long-term storage, without media replacement. Furthermore, the cells can be in suspension or in a support matrix designed for cell delivery.

In another embodiment, the present invention provides a cell culture medium to induce and maintain rapid differentiation of retinal pigment epithelial cells. In a further embodiment, the present invention provides a cell culture medium, for RPE, as well as other cells, which allows and assures rapid attachment onto untreated surfaces, including, but not limited to, tissue culture plastic without coating for attachment (e.g., laminin, fibronectin, and matrigel).

As disclosed herein, the medium is based on secreted molecules generated as conditioned media (CM) containing bovine corneal endothelial cell (BCEC) secreted molecules, either the CM itself, components of the CM or a combination of components based on the identification of active molecules in BCEC-conditioned media. The medium of present invention can be used as a storage/preservation medium without changing or replenishing. This medium can also be used as a cell culture medium for inducing rapid differentiation in RPE when changed three times per week.

The present invention offers distinct advantages over technology currently in existence. Storage and preservation media currently exist for corneas but there is no medium specifically developed for use with RPE or for other similar types of cells. The composition and concentration of the components of the present invention vary significantly from that of existing cornea storage media. Furthermore, when used as a differentiation medium, the present invention features a rapid induction of differentiation, which exceeds that of standard RPE culture media. Morphological indicators of differentiation in fetal RPE demonstrate that the onset of differentiation occurs very rapidly (e.g., within one week when seeded at 3164 cells/mm$^2$), and the cells achieve a level of differentiation that is only observed (if at all) in long-term fetal RPE culture in standard RPE culture media.

Finally, when used as a cell culture medium for RPE, a BCEC-conditioned medium induces unexpected rapid attachment of cells onto untreated tissue culture plastic (attachment as soon as one hour following seeding) and effects accelerated growth and differentiation. On the other hand, a standard RPE culture medium attachment takes approximately 24 hours on untreated tissue culture plastic, with a marked difference in the rate of growth. This aspect of the present invention, a reduction of the time required to achieve differentiated RPE (or other cells, tissues or organs), provides a substantial advantage in the field of manufacturing. For example, in the case of induced pluripotent stem cells (iPSC), BCEC-conditioned media can reduce the time a patient has to wait for autologous cell transplantation.

The role of the medium of the present invention as a storage medium presents a marked improvement over existing technology. In order to solidify its usefulness, quantitative analysis of cell viability at different time points can be performed, in order to compare cell death rates in different media. Additionally, maintenance of RPE markers can be compared in different media with time in culture. Since another method of cell introduction at the time of transplantation is single-cell suspensions, it can also be determined, as part of the present invention, whether RPE can maintain viability in suspension in BCEC-CM. Generally, RPE are anchorage-dependent cells that undergo apoptosis if not attached to a suitable substrate. Since BCEC-CM contains many soluble ECM ligands, this medium can likely support cells in suspension. Injection of fresh, as opposed to frozen, cells could be advantageous for cell transplantation of since frozen cells must recover after thaw and tend to attach and grow sluggishly compared to fresh cells. Additionally, frozen cells must be washed to remove DMSO (in freezing solution) while fresh cells could be injected directly from the storage vial.

The present invention aims to identify the cell-supporting components in BCEC-CM and to manufacture a solution comprised of small molecules and human recombinant proteins for commercial development. Although an RPE medium appears to support cells to a similar degree as BCEC-CM (except at the condition noted previously), the presence of fetal bovine serum in the medium is not ideal (xenogeneic proteins). The storage solution for commercial development can be a newly-developed product with a unique formation or can be molecules added to Optisol to increase effectiveness.

Since the presence of mRNA does not necessarily predict protein presence, the present invention can include a determination of the expression of RPE differentiation markers (proteins) with time in culture. Long-term cultures of fetal RPE on BCEC-ECM and on tissue culture plastic in standard RPE media and BCEC-CM can be compared. Preliminary data indicate that protein expression of late differentiation markers (RPE65 and bestrophin) cannot be detected in the conditions tested to date (3 weeks). If fetal RPE differentiates more rapidly in BCEC-CM than in standard RPE media, similar studies on hES-RPE (Advanced Cell Technology) can be performed.

The invention will now be described in the following non-limiting examples.

EXAMPLES

Example 1

Long-Term Survival of Fetal RPE on Aged Submacular Human Bruch's Membrane is Impaired Fetal RPE (3164 cells/mm$^2$) were seeded on aged human submacular Bruch's membrane debrided to expose the superficial surface of the inner collagenous layer. To create surfaces exposing the RPE basement membrane, RPE were gently wiped off the RPE/choroid/sclera explant using a wet surgical sponge. To create surfaces exposing the surface of the inner collagenous layer beneath the RPE basement membrane (i.e., superficial ICL), following RPE removal as indicated previously, a moistened surgical sponge was use to abrade the RPE basement membrane. In general, the area of RPE basement membrane debridement was created by approximately 5 wipes of the moistened sponge in each of 4 directions (rotating the explant 90 degrees after each series of 5 wipes). (V. K. Gullapalli, et al., Exp Eye Res 2005; 80(2):235-248). Cells were seeded onto the sclera/choroid explant and cultured for 21 days and evaluated for resurfacing with scanning electron microscopy (SEM) and light microscopy (LM). Nuclear density counts (mean±SD) of fetal RPE on aged submacular human Bruch's membrane at day-1 (basement membrane, N=7; superficial ICL, N=7), day-7 (basement membrane, N=6; superficial ICL N=6), day-14 (basement membrane N=7), day-21 (superficial ICL, N=6) were performed on 5 non-adjacent slides in the central 3 mm of the section (includes the submacular region of Bruch's membrane). Cells on tissue culture dishes coated with BCE-ECM (N=1) are included for comparison. Cells were seeded at a density of 3164 cells/mm$^2$ for all time points and surfaces.

Figure 1:
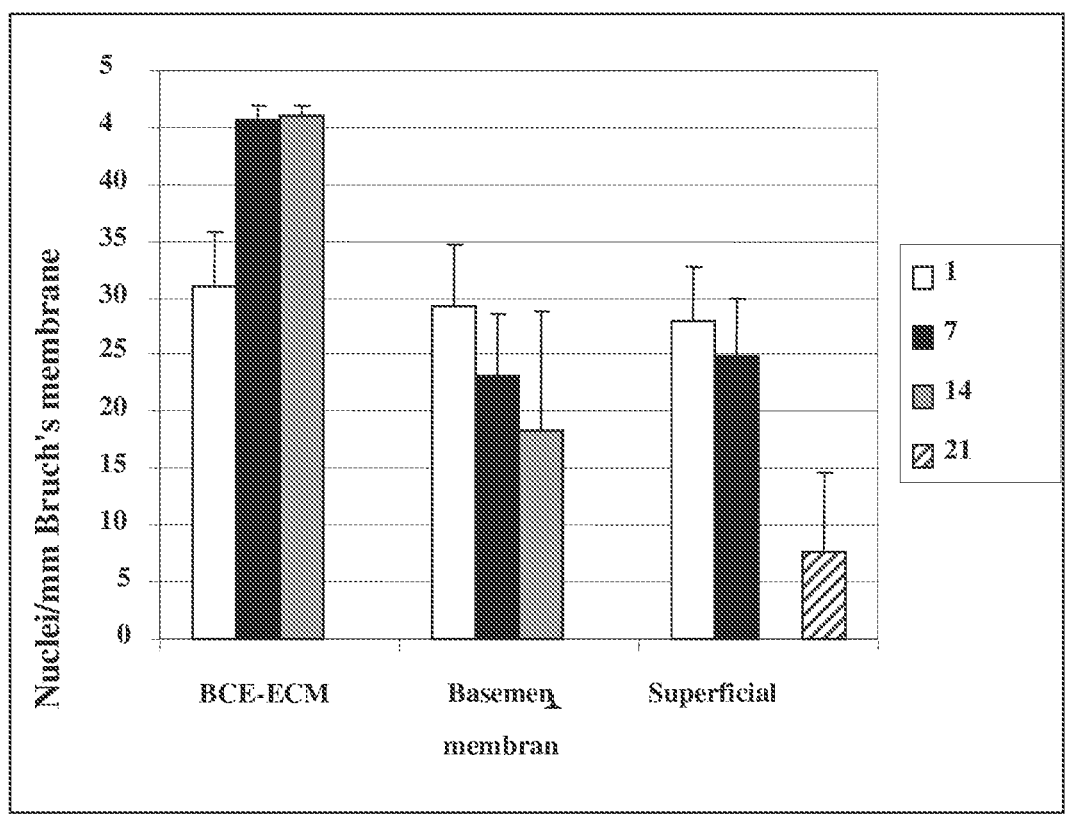
FIG. 1 demonstrates that long-term survival of fetal RPE on aged submacular human Bruch's membrane is impaired if the surface (basement membrane or superficial surface of the inner collagenous layer (ICL)) is not treated.

Fetal RPE survival on submacular Bruch's membrane decreased with time, regardless of the surface on which the cells are seeded (e.g., RPE basement membrane or the surface of the inner collagenous layer (superficial ICL)) (See FIG. 1, modified from V. K. Gullapalli, et al., Exp Eye Res 2005; 80(2):235-248.) (Transplanted RPE will encounter superficial ICL in situ if native RPE are removed by CNV excision.) In contrast, density increased to 45 nuclei/mm$^2$ if RPE are grown on bovine corneal endothelial cell extracellular matrix (BCE-ECM)-coated culture dishes.

Example 2

Fetal RPE Resurfacing on Aged Bruch's Membrane Resurfaced with Bovine Corneal Endothelial Matrix (BCE-ECM)

Figure 2:
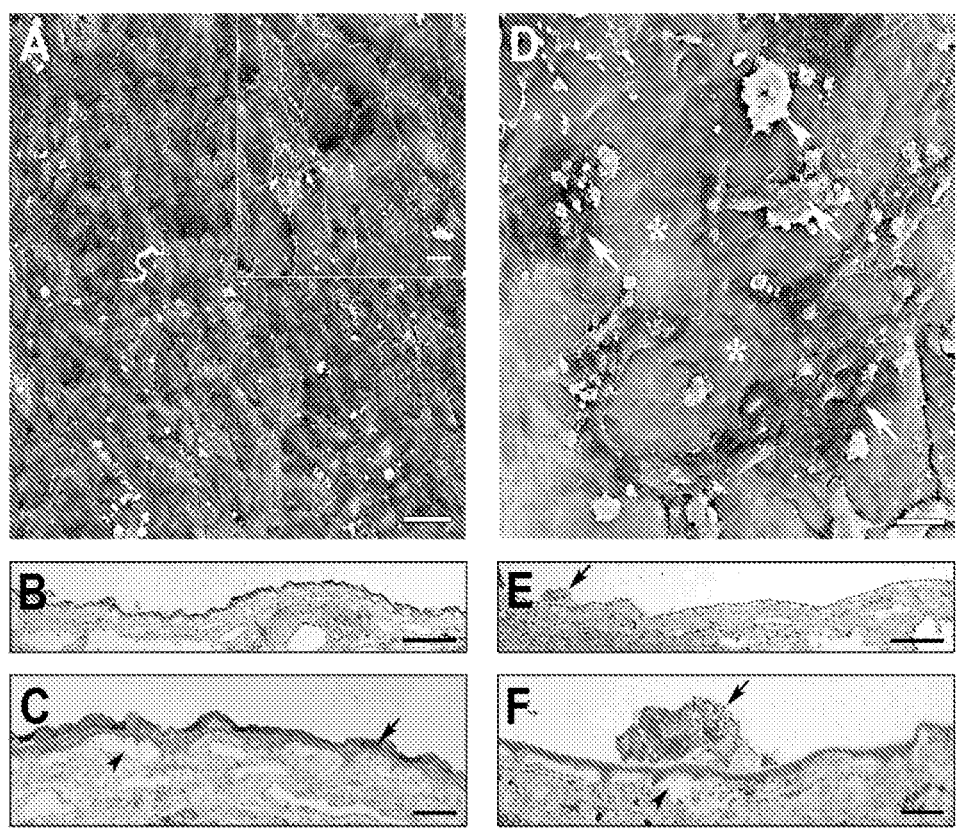
FIG. 2 demonstrates fetal RPE resurfacing on aged human submacular Bruch's membrane is improved following resurfacing with bovine corneal endothelial cell extracellular matrix (BCE-ECM).

BCE (3164 cells/mm$^2$) were cultured on the inner collagenous layer of aged human submacular Bruch's membrane (65 yr. old donor) for 14 days to allow ECM deposition. Cells were culture in the same way as cells cultured for ECM deposition on culture dishes (see paragraph 0056). Following BCE removal with NH$_4$OH to expose the newly deposited ECM and extensive washing with PBS, explants were seeded with fetal RPE (3164 cells/mm$^2$) and cultured for 21 days. The results of these experiments are illustrated in FIG. 2.

FIG. 2A is a scanning electron micrograph (SEM), showing that fetal RPE fully resurfaced the treated explant with large, flat polymorphic cells. Cells showed varying amounts of short apical processes on their surfaces (insert). Mag. bar 50 μm; insert mag bar 10 μm.

FIGS. 2B and 2C are light micrographs (LMs). As shown in FIG. 2B, cells fully resurfaced the treated explant and are in a monolayer. Mag. bar 100 μm. FIG. 2C is a higher magnification of the explant shown in FIG. 2B, allowing one to discern the variable morphology of the cells. Cells are tightly adherent to the explant surface. Arrow in FIG. 2C points to the nucleus of a cell in the monolayer; arrowhead to a choriocapillaris vessel. Mag. bar 20 μm.

As a negative control, submacular Bruch's membrane of the fellow eye was incubated in serum-free media with no BCE for 14 days followed by exposure to NH$_4$OH, rinsing with PBS and fetal RPE seeding and culturing for 21 days.

FIG. 2D is a SEM of the RPE on the untreated Bruch's membrane surface. Notably, fetal RPE incompletely resurfaced the untreated inner collagenous layer. Islands of large, flattened cells are present (arrows). Dead, dying, or poorly attached cells are also present on the surface or attached to the flattened cells (arrowhead). Asterisk, exposed inner collagenous layer surface. Mag. bar 50 μm.

FIGS. 2 E and 2F show a representative view of the RPE on untreated Bruch's membrane. In this section, there is only a single clump of cells (arrow). Mag. bar 100 μm. FIG. 2F is a high magnification of the clump of cells shown in FIG. 2E. Arrow points to a cell in the clump that is not intact. Arrowhead points to a choriocapillaris vessel. Mag. bar 20 μm.

Example 3

Resurfacing Bruch's Membrane with a Biologically Deposited Extracellular Matrix (ECM) Improves Cell Survival Bovine corneal endothelial cells (BCE, passage-2) were seeded onto human submacular superficial ICL of Caucasian donors over 55 years old at a density of 3164 cells/mm$^2$ and cultured for 14 days to allow ECM deposition or treated for 14 days with serum-free media only. Following BCE removal with NH$_4$OH and extensive rinsing, fetal RPE (passage-2-5) were seeded at the same density onto the treated Bruch's membrane surface and cultured for 21 days. The fellow eye was treated similarly except no BCE were seeded.

Figure 3:
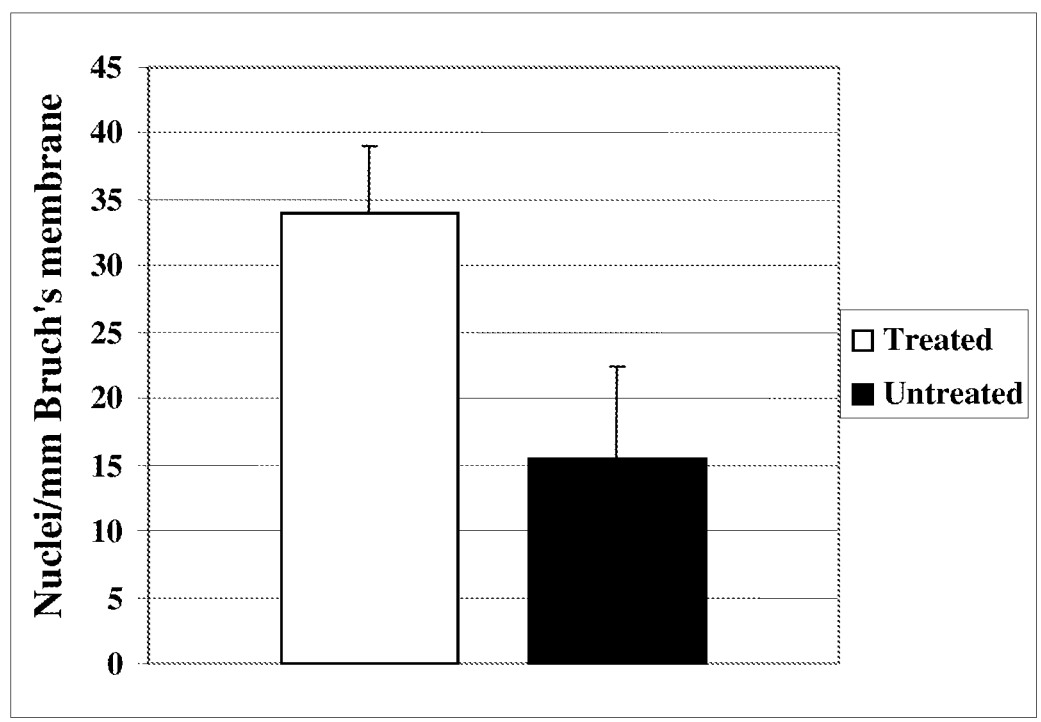
FIG. 3 demonstrates that resurfacing aged human submacular Bruch's membrane with a biologically deposited extracellular matrix (ECM) improves long-term RPE survival compared to untreated Bruch's membrane by over 200%.

RPE seeding density was 3164 cells/mm$^2$ for 21-day incubations to determine long-term survival and morphology. FIG. 3 shows the cumulative data from 9 explant pairs. Counts are mean fetal RPE nuclei/mm Bruch's membrane (±SEM).

A statistically significant 230% (p=0.006) increase in cell density is seen at day-21 on treated explants compared to explants treated with serum-free DMEM only (FIG. 3) or explants in which cells were seeded directly on Bruch's membrane with no prior treatment (FIG. 1, day-21 superficial ICL (striped bar)).

Example 4

Bovine Corneal Endothelial Cells (BCE) Secrete ECM Components into the Overlying Media During ECM formation, in addition to basal secretion, BCE secrete ECM components into the media (BCE-conditioned media, BCE-CM), and the composition and relative amounts of the components vary with culture time and passage number. Secretion of ECM components into the overlying media is most abundant in early passage cells (up to passage-2) and exceeds basal ECM deposition in quantity. (Tseng et al. *J Biol Chem* 1981; 256:3361-3365).

Serum-free BCE-conditioned media (BCE-CM) was prepared from passage-2 cells that were cultured in serum-free Dulbecco's modified Eagle's medium (DMEM) for 48 hrs. An initial sample concentrated using a 30 kD cut-off filter identified 20 proteins by MS/MS-MALDI. The proteins in an additional sample of conditioned media, unfiltered, were subjected to 2D LC-MS/MS, and samples were analyzed with MALDI-TOF and QTOF.

These analyses identified 84 proteins (at least one peptide having C.I. values of >95%). Conditioned media from the same preparation was also analyzed by 2D gel separation, and selected spots (142) were analyzed by MALDI-TOF. This analysis identified 45 different proteins. A combined total of 109 proteins were identified using these methods (Table 1).

TABLE 1

Protein components of two different samples of bovine corneal endothelial cell conditioned media (BCE-CM) as determined by MS/MS-MALDI, LC-MS/MS (MALDI-TOF and Q-TOF), and MS/MS-MALDI of selected 2D gel spots. Proteins were identified based on at least one peptide with C.I. value 95% or more.

| Name | Protein Description |
| --- | --- |
| IGF-1 | prepro-insulin-like growth factor I |
| IGFBP-2 | Insulin-like growth factor-binding protein-2 |
| IGFBP-4 | insulin-like growth factor-binding protein-4 |
| IGFBP-7 | PREDICTED: similar to insulin-like growth factor binding protein 7 (predicted), partial |

TABLE 1-continued

Protein components of two different samples of bovine corneal endothelial cell conditioned media (BCE-CM) as determined by MS/MS-MALDI, LC-MS/MS (MALDI-TOF and Q-TOF), and MS/MS-MALDI of selected 2D gel spots. Proteins were identified based on at least one peptide with C.I. value 95% or more.

| Name | Protein Description |
| --- | --- |
| FN | Fibronectin (FN) |
| hypothetical protein | hypothetical protein LOC504471 |
| H factor 1 | H factor 1 (complement) |
| C3 | Chain B, Structure Of Mammalian C3 With An Intact Thioester At 3a Resolution |
| C3 | Complement component 3 |
| C3d | Complement component C3d |
|  | PREDICTED: similar to Complement C3 precursor, partial |
|  | Complement C3 precursor [Contains: Complement C3 beta chain; Complement C3 alpha chain; C3a anaphyl |
| C4 | PREDICTED: similar to Complement C4 precursor |
| CCP modules | CCP modules 3-12, with parts of CCP 2 and 13 |
| collagen, type I | collagen, type I, alpha 2 |
| collagen, type III | collagen, alpha-1 (III) chain |
| collagen, type V | type V preprocollagen alpha 2 chain |
| collagenase type IV | collagenase type IV precursor |
| TIMP2 | tissue inhibitor of metalloproteinase 2 |
| MMP2 | matrix metalloproteinase 2 |
| EGF-containing fibulin-like extracellular matrix protein 1 | PREDICTED: similar to EGF-containing fibulin-like extracellular matrix protein 1 isoform a precursor |
|  | PREDICTED: similar to EGF-containing fibulin-like extracellular matrix protein 1 isoform b |
| fibulin-3, FIBL-3 | EGF-containing fibulin-like extracellular matrix protein 1 precursor |
| fibulin-1 | fibulin-1 C |
| SPARC protein | SPARC protein |
| Osteonectin | secreted protein, acidic, cysteine-rich (osteonectin) |
| ESM-1 | PREDICTED: similar to Endothelial cell-specific molecule 1 precursor (ESM-1 secretory protein) |
| apolipoprotein A | apolipoprotein A-I precursor |
| apolipoprotein E | apolipoprotein E |
|  | apolipoprotein E precursor |
| EC-SOD | PREDICTED: similar to Extracellular superoxide dismutase [Cu—Zn] precursor (EC-SOD) isoform 2 |
| PCSK9 | PREDICTED: similar to proprotein convertase subtilisin/kexin type 1 inhibitor precursor |
| alpha-actin | alpha-actin |
| Alpha-cardiac actin | PREDICTED: similar to Actin, alpha cardiac (Alpha-cardiac actin) isoform 1 |
| Beta-actin | Actin, cytoplasmic 1 (Beta-actin) |
| actinin | PREDICTED: similar to actinin alpha 4 isoform 3 |
|  | actinin, alpha 1 |
| POTE-2 | PREDICTED: similar to Prostate, ovary, testis expressed protein on chromosome 2 |
| Dkk-3 | PREDICTED: similar to Dickkopf related protein-3 precursor (Dkk-3) (Dickkopf-3) (hDkk-3) |
|  | dickkopf homolog 3 |
| cathepsin L | cathepsin L |
| Fibulin-1 | PREDICTED: similar to Fibulin-1 precursor isoform 1 |
| Thrombospondin-1 | Chain A, Crystal Structure Of The Thrombospondin-1 N-Terminal Domain |
| Vimentin | Vimentin |
| PGDS | prostaglandin D2 synthase precursor |
| ITI | PREDICTED: similar to inter-alpha trypsin inhibitor heavy chain precursor 5 isoform 1 |
| nidogen | nidogen |
| Entactin | PREDICTED: similar to Nidogen precursor (Entactin) isoform 3 |
| Osteonidogen | PREDICTED: similar to Nidogen-2 precursor (NID-2) (Osteonidogen) |
| MGP | matrix Gla protein |
| HSPG | PREDICTED: heparan sulfate proteoglycan 2 |
|  | heparan sulfate proteoglycan perlecan |
|  | PREDICTED: similar to Basement membrane-specific heparan sulfate proteoglycan core protein precursor |
| nephronectin | PREDICTED: similar to nephronectin isoform b |
| FSTL1 | Follistatin-related protein 1 precursor (Follistatin-like 1) (TGF-beta-inducible protein TSC-36) |
| FSTL3 | PREDICTED: similar to Follistatin-related protein 3 precursor (Follistatin-like 3) (Follistatin-rel |
| LTBP-2 | Latent-transforming growth factor beta-binding protein 2 precursor (LTBP-2) |
| albumin | albumin |
| transthyretin | transthyretin |
| NPC | Alveolar macrophage chemotactic factor (Neutrophil chemotactic protein) (NPC) |
| CTGF | connective tissue growth factor |

TABLE 1-continued

Protein components of two different samples of bovine corneal endothelial cell conditioned media (BCE-CM) as determined by MS/MS-MALDI, LC-MS/MS (MALDI-TOF and Q-TOF), and MS/MS-MALDI of selected 2D gel spots. Proteins were identified based on at least one peptide with C.I. value 95% or more.

| Name | Protein Description |
| --- | --- |
| Dimeric Bovine Tissue-Extracted Decorin | Chain B, Dimeric Bovine Tissue-Extracted Decorin, Crystal Form 2 |
| GOLPH2 | PREDICTED: similar to golgi phosphoprotein 2 |
| KIAA1133 | PREDICTED: similar to KIAA1133 protein |
| GST | glutathione S-transferase, GST {N-terminal} {EC 2.5.1.18} [cattle, erythrocytes, Peptide Partial, 2 |
| serine protease | serine protease |
| SMC1 | mitosis-specific chromosome segregation protein SMC1 homolog |
| superfast myosin | PREDICTED: similar to superfast myosin heavy chain |
| AEBP1 | AE binding protein 1 |
| angiomodulin | angiomodulin |
| anti-PPS | anti-pneumococcal capsular polysaccharide immunoglobulin heavy chain variable region |
| N-cadherin | Cadherin-2 precursor (Neural-cadherin) (N-cadherin) (CD325 antigen) |
| CD44 | CD44 antigen precursor (Phagocytic glycoprotein I) (PGP-1) (HUTCH-I) (Extracellular matrix receptor) |
| APT | Chain A, Crystal Structure Of The First Active Autolysate Form Of The Porcine Alpha Trypsin |
| ACTH | preproadrenocorticotropic hormone (ACTH) corticotropin corticotropin-like interm lobe peptide |
| cystatin C | cystatin C (amyloid angiopathy and cerebral hemorrhage) [Bos taurus] |
| fibromodulin | fibromodulin |
| galanin | galanin |
| polypeptide | precursor polypeptide (AA −31 to 1139) |
| PTGDS | prostaglandin H2 D-isomerase |
| microglobulin | similar to beta 2-microglobulin |
| lumican | lumican |
| gelsolin | gelsolin |
| cadherin 11 | cadherin 11, type 2 preproprotein |
| Transferrin | Serotransferrin precursor (Transferrin) (Siderophilin) (Beta-1-metal-binding globulin) |
| PDI | Protein disulfide-isomerase A3 precursor (Disulfide isomerase ER-60) (ERP60) |
| Nucleobindin 1 | Nucleobindin 1 |
| Calnuc | Chain A, Nmr Solution Structure Of The Calcium-Binding Domain of Nucleobindin (Calnuc) |
| Osteonectin | Secreted protein, acidic, cysteine-rich |
| Beta-globin | Hemoglobin subunit beta (Hemoglobin beta chain) (Beta-globin) |
| Alpha enolase | Alpha enolase |
| FHOS2S splicing variant [ | FHOS2S splicing variant |
| Aldehyde dehydrogenase | aldehyde dehydrogenase family 1, subfamily A1 |
| LDHA | Lactate dehydrogenase-A |
| ATIC-ALK | Tropomyosin 4-anaplastic lymphoma kinase fusion protein Tyrosine 3-/tryptophan 5-monooxygenase activation protein, epsilon polypeptide |
| Human Annexin A2 | Chain A, Structure Of Human Annexin A2 In The Presence Of Calcium Ions |
| Peroxiredoxin 1 | Peroxiredoxin 1 |
| Peroxiredoxin 6 | Peroxiredoxin 6 |
| Anti-oxidant protein 2 | Anti-oxidant protein 2 (non-selenium glutathione peroxidase, acidic calcium-independent phospholipa) |
| NME4 | Expressed in non-metastatic cells 1 protein |
| biglycan | biglycan |
| clusterin | clusterin osteoglycin plasminogen activator inhibitor type 1, member 2 transketolase |

Example 5

Bovine Corneal Endothelial Cell Conditioned Media (BCE-CM) can Improve RPE Cell Survival on Aged Human Submacular Bruch's Membrane BCE-CM containing serum was prepared by exposing newly confluent cultures of BCE to RPE complete media (DMEM with 2 mM glutamine, 15% fetal bovine serum, 2.5 µg/ml fungizone, 0.05 mg/ml gentamicin, 1 nag/ml bFGF) for 3 days. Media was centrifuged and supernatant stored frozen. Submacular aged human Bruch's membrane explants were debrided to expose the superficial inner collagenous layer; 3164 cells/mm$^2$ were seeded on each explant and cultured for 21 days. Explants with cells were cultured in serum-containing BCE-CM or RPE complete media.

Figure 4:
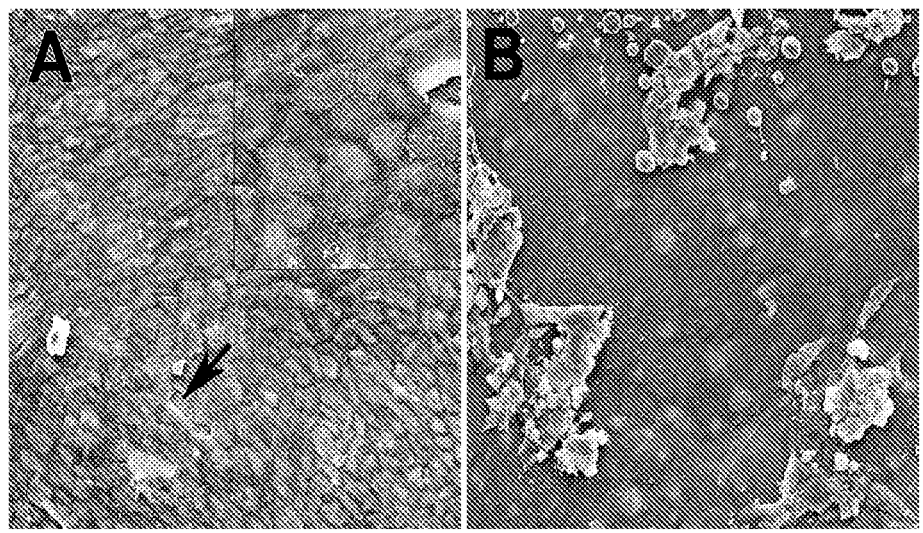
FIG. 4 illustrates RPE survival on submacular human Bruch's membrane of an AMD donor (age 79 years) cultured in serum-containing bovine corneal endothelial cell-conditioned media (BCE-CM) vs. routine RPE culture media. In the absence of Bruch's membrane treatment, these RPE cells generally show poor survival on human submacular Bruch's membrane of AMD eyes after 21 days in organ culture.

Preliminary data using serum-containing BCE-CM as media for RPE following seeding onto peripheral (N=2) and submacular Bruch's membrane (N=1, with submacular drusen) shows BCE-CM used as media supports better RPE attachment and long-term survival than RPE complete media (FIG. 4). In the experiments illustrated in FIG. 4, submacular human Bruch's membrane of an AMD donor (age 79 years) was treated with serum-containing bovine corneal endothelial cell-conditioned media (BCE-CM) vs. routine RPE culture media; BCE-CM was prepared by exposing passage-2 BCE for 3 days in RPE complete media containing serum. The explant to be treated had a greater number of large submacular drusen than the control explant, which means it was the more severely diseased of the two eyes. A. RPE cultured in BCE-CM, day 21. Cells fully resurface the treated explant with a few small defects (arrow). High magnification insert shows short apical processes on the surface of some cells and along cell borders. B. RPE cultured in RPE complete media, day-21. The explant is sparsely resurfaced with patches or clumps of RPE. Original magnifications 200×; insert 1000×.

Figure 5:
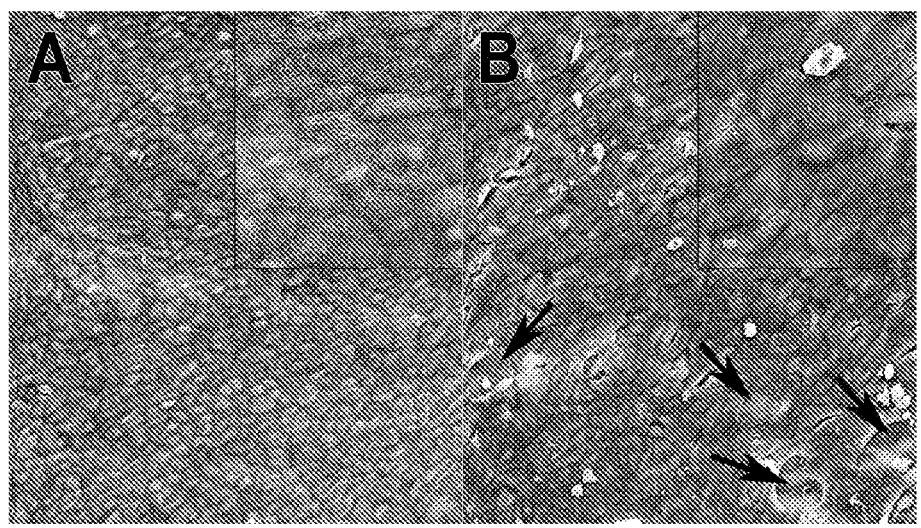
FIG. 5 illustrates improved RPE survival with 21 day exposure to serum-containing BCE-CM compared to 2 day exposure on human peripheral Bruch's membrane from a non-AMD donor (age 80 years).

The inventors have also shown serum-containing BCE-CM used as media during the duration of the incubation (21 days) showed better cell morphology and resurfacing on peripheral inner collagenous layer of Bruch's membrane than explants where BCE-CM was changed to standard RPE media (which also contains serum) after 2 days (FIG. 5). In these experiments, RPE survival on peripheral Bruch's membrane from a non-AMD donor (age 80 years) was investigated. A. Aged human peripheral Bruch's membrane explant cultured for 21 days in BCE-CM. Explant is fully resurfaced with a fairly uniform monolayer of cells. High magnification insert shows short apical processes covering the surface of the cells. B. Aged human peripheral Bruch's membrane (isolated from fellow eye of that shown in A) explant cultured for 2 days in BCE-CM then placed in RPE complete media for 19 days. Explant is incompletely resurfaced (arrows point to defects) with cells of varying size and morphology. High magnification insert shows the cells have a few very short apical processes, and the cells are fairly large and smooth. Original magnifications: 200×; inserts: 1000×.

Example 6

Bovine Corneal Endothelial Cell Conditioned Media (BCE-CM) Supports Rapid RPE Attachment and Spreading on Non-Tissue Culture Treated Plastic to a Similar Degree as Cells on BCE-ECM-Coated Tissue Culture Plastic Soluble ECM can affect cell shape and metabolism in addition to stimulating production of ECM molecules. The inventors performed studies to determine: 1) whether soluble components in BCE-CM can be used instead of BCE-ECM to coat culture dishes and support fetal RPE growth and differentiation; and 2) whether BCE-CM used as media for cell suspension and seeding can support cells on non-tissue culture treated dishes (NTC). Since serum contains ECM ligands (e.g., vitronectin and fibronectin), these studies were performed in serum-free media as the most stringent test of cell support. Because of RPE dependence on serum in the media for long-term survival, experiments were performed for 3 days only.

Serum-free conditioned media (sfBCE-CM) was prepared from passage-2 cultures as described above. sfBCE-CM was applied in media or by coating non-tissue culture treated dishes (NTC) unconcentrated or in concentrated form (8-fold, using a 30 kD cut-off filter). Negative control was cells seeded and cultured in DMEM only. Fetal RPE (passage-3) were seeded at a density of 526 cells/mm$^2$ for all attachment studies. To determine whether non-protein components of BCE-CM contribute to early attachment and spreading of fetal RPE, sfBCE-CM was heated to 80° for 15 minutes, centrifuged, and the supernatant was used as media for attachment and seeding of fetal RPE. The importance of intact protein components in BCE-CM evidenced by cell behavior in heat-treated sfBCE-CM was confirmed by treatment with proteinase K agarose beads (removed prior to cell suspension and seeding) before and after heat treatment.

sfBCE-CM used either as media (Table 2, A) or as a substrate to coat tissue culture dishes (Table 2, B) supported rapid RPE adhesion and cell division in serum-free conditions. sfBCE-CM-treated dishes supported rapid attachment and spreading by 1 hour (Table 2, B), similar to BCE-ECM-treated dishes (Table 2, D). Fetal RPE seeded in heat inactivated and/or proteinase K-treated BCE-CM behaved similar to those on NTC (Table 2A, C). Cells seeded onto 8× sfBCE-CM did attach and spread but to a slightly lesser degree than on unconcentrated CM. The best morphology (uniform spreading, less filopodia formation) was observed in cells on BCE-ECM and in sfBCE-CM used as media or as a coating substrate. Experiments are in progress to determine whether differences in cell behavior are observed in media harvested from BCE of different passages and times in culture.

TABLE 2

Fetal RPE behavior in serum-free BCE conditioned media (sfBCE-CM) under different culture conditions. Cells were seeded at the same density for all experiments. A. Effect of sfBCE-CM as media for attachment and growth. sfBCE-CM, heat inactivated sfBCE-CM, and sfBCE-CM treated with proteinase K are compared. B. Effect of sfBCE-CM as a surface treatment for attachment and growth on non-tissue culture treated (NTC) dishes, either unconcentrated or concentrated 8X using a 30 kD cut-off filter. Cells were suspended and cultured in either DMEM or sfBCE-CM. C. Control (cells on untreated NTC dishes with DMEM as media). D. Control (cells on BCE-ECM with DMEM as media).

| Experimental Condition | 1 Hour | Day-1 | Day-3 |
| --- | --- | --- | --- |
| A. RPE CELL ATTACHMENT AND GROWTH IN sfBCE-CM | | | |
| sfBCE-CM | ~40% spread | ~70-80% spread, almost confluent | Confluent, uniform cell size, few vacuoles |
| sfBCE-CM, heat inactivated | Rounded | Few cells, filopodia | More cells than at day-1 but very few, poor morphology. |
| sfBCE-CM, proteinase | Rounded | Rounded | Rounded |

TABLE 2-continued

Fetal RPE behavior in serum-free BCE conditioned media (sfBCE-CM) under different culture conditions. Cells were seeded at the same density for all experiments. A. Effect of sfBCE-CM as media for attachment and growth. sfBCE-CM, heat inactivated sfBCE-CM, and sfBCE-CM treated with proteinase K are compared. B. Effect of sfBCE-CM as a surface treatment for attachment and growth on non-tissue culture treated (NTC) dishes, either unconcentrated or concentrated 8X using a 30 kD cut-off filter. Cells were suspended and cultured in either DMEM or sfBCE-CM. C. Control (cells on untreated NTC dishes with DMEM as media). D. Control (cells on BCE-ECM with DMEM as media).

| Experimental Condition | 1 Hour | Day-1 | Day-3 |
|---|---|---|---|
| K treatment with and without prior heat inactivation | | | |
| B. sfBCE-CM SURFACE COATING OF NTC DISHES FOLLOWED BY RPE SEEDING WITH DMEM OR sfBCE-CM MEDIA | | | |
| sfBCE-CM, DMEM | 40-50% spread | High density, confluent in center, some multi-nucleate cells | Confluent, small cells, good, morphology, few vacuoles |
| sfBCE-CM, sfBCE-CM | ~70% spread | Moderate density, filopodia and lamellipodia | Elongate cells with filopodia and lamellipodia, subconfluent |
| 8X sfBCE-CM, MW>30K, DMEM | ~60% spread | High density of cells, confluent in center, similar to 1X BCE-CM, DMEM | Almost confluent, more variable morphology than 1X BCE-CM, DMEM |
| 8X sfBCE-CM, MW>30K, sfBCE-CM | 50-60% spread | Moderate density of cells, filopodia and lamellipodia | Elongate cells with filopodia and lamellipodia, subconfluent |
| C. NEGATIVE CONTROL | | | |
| NTC plastic, DMEM | Rounded | Rounded | Few elongated cells |
| D. POSITIVE CONTROL | | | |
| BCE-ECM surface | ~50-90% spread | Majority cells are spread but not confluent, some filopodia | Cells spread and proliferating, almost confluent |

Preliminary experiments with media harvested from passage-2 cultures show that media harvested from cells that have been in culture for 2 weeks after reaching confluency is not as supportive as media harvested at earlier time points (50% confluent, confluent, 1 week after confluency) (data not shown). Protein composition analysis is currently underway to determine changes in the media harvested at these different time points to determine what proteins may account for the decreased cell support.

Example 7

Figure 6:
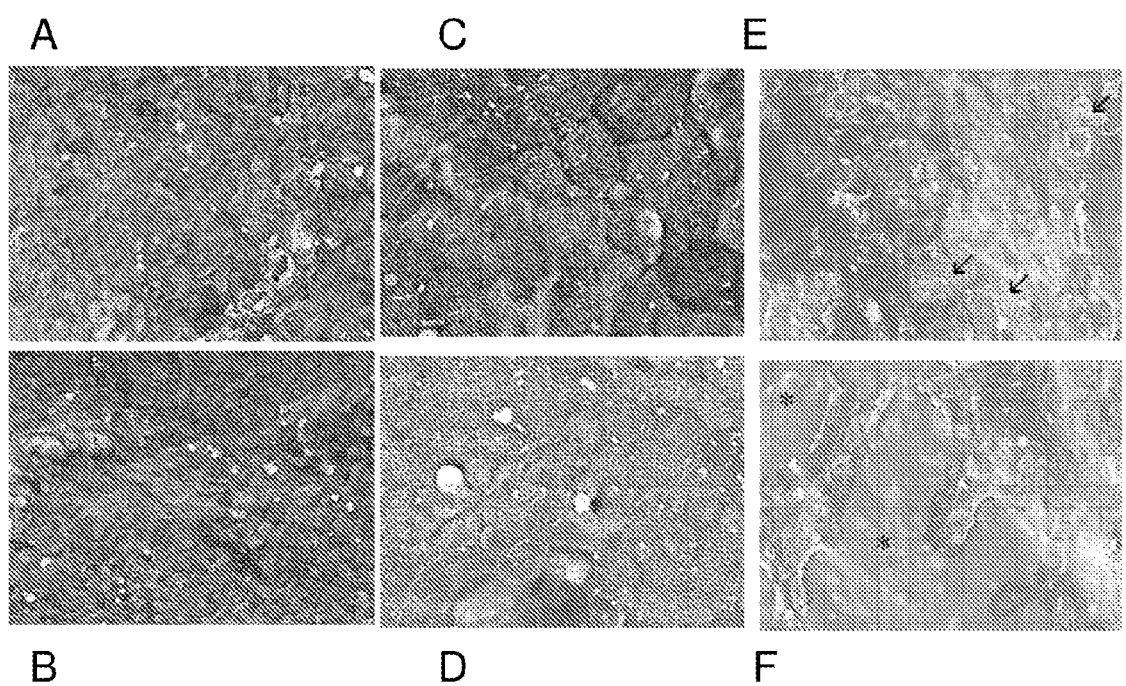
FIG. 6 demonstrates that overnight treatment with serum-free BCE-conditioned media results in improvement of RPE survival and differentiation on human submacular Bruch's membrane.

Soaking in Serum Free BCE-CM can Improve Cell Survival on Aged AMD Bruch's Membrane FIG. 6 demonstrates that even a relatively short treatment (i.e., overnight) leads to improvement in RPE survival on and resurfacing of Bruch's membrane. In this experiment, submacular Bruch's membrane from an 80 year-old Caucasian male donor was debrided to expose the superficial inner collagenous layer. Large submacular drusen were present on Bruch's membrane of both eyes, and the eye treated with BCE-CM showed more deposits (i.e., was the more severely diseased of the two eyes). Bruch's membrane was treated by overnight soaking of the explant in serum-free BCE-CM; the fellow eye explant was soaked for the same period of time in regular serum-free media (DMEM). Fetal RPE were seeded onto both Bruch's membrane explants at a seeding density of 3164 cells/mm². Both explants were cultured in RPE complete media for 21 days.

The explant treated with the conditioned media as described in the previous paragraph shows almost 100% resurfacing with a few small defects (FIG. 6A, B, original magnification 200×). The high magnification images (1000×) show small cells with varying amounts of apical processes (a differentiation feature) (FIG. 6C, D). In contrast, the untreated explant shows incomplete resurfacing by very large flat smooth cells (FIG. 6 E, F, original magnification 200×). Areas of cellular debris are evident where the cells have died (arrows). Asterisks indicate areas not resurfaced.

Example 8

Treatment of Aged Bruch's Membranes with BCE Conditioned Media Improves Survival of RPE Derived from Human ES Cells In order to investigate whether treatment of surfaces with BCE-conditioned media improves survival and/or differentiation of RPE other than fetal RPE, the following experiments were performed. Fresh (not frozen) RPE derived from human ES cells (hES-RPE obtained from Advanced Cell Technology, Inc.) of intermediate pigmentation were seeded onto the inner collagenous layer of submacular Bruch's membrane from a 63 year-old Caucasian female at a seeding density of 3164 cells/mm². There was no evident pathology in the macula of either eye. The treated explant was cultured in serum-containing BCE-CM while the untreated explant was cultured in RPE complete media. Explants were harvested after 21 days in culture.

Figure 7:
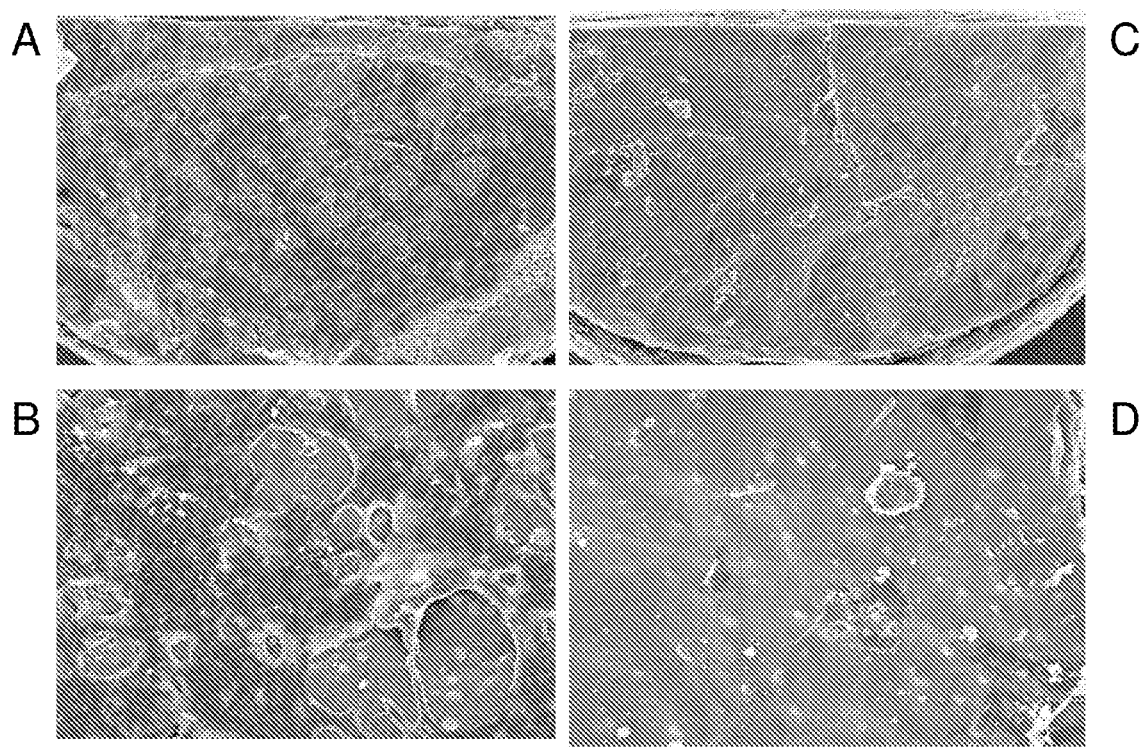
FIG. 7 demonstrates that RPE derived from human embryonic stem cells successfully survive on aged human submacular Bruch's membrane treated with serum-free BCE-conditioned media (BCE-CM) (A, B), compared to untreated submacular Bruch's membrane (C, D).

The results of these experiments are illustrated in FIG. 7. The treated explant (FIG. 7 A, B) demonstrated some degree of resurfacing by the hES-RPE with defects in coverage. The cells were very flat and did not show prominent differentiated features. The untreated explant (FIG. 7C, D) showed only sparse coverage, with only a few cells in the submacular region of the explant. Thus, BCE-CM treatment improved hES-RPE survival on aged human Bruch's membrane.

Example 9

Active Components in BCE-CM Supporting Early Attachment and Spreading in Cell Culture Different preparations of sfBCE-CM of different molecular weight cut-off were prepared to determine the MW fraction of active components in sfBCE-CM. Media were reconstituted to 1× following filtration. Retentate solutions of MW>3 kD, >10 kD, >30 kD, and >50 kD and filtrate solutions of MW<3 kD, <10 kD, <30 kD, and <50 kD were prepared. RPE (passage-4) were suspended in each solution and seeded onto non-tissue cultured treated plastic (NTC) as detailed above. In a separate study, sfBCE-CM was filtered using a 100 kD molecular cut off filter, yielding filtrates of <100 kD and retentates of >100 kD. Fetal RPE (passage-3) behavior was observed in the 2 solutions up to day-2.

The active cell-supporting components in BCE-CM appear to at least include molecular weight (MW) 30 kD and higher. Based on day-3 observations of vacuole formation (early apoptotic changes) in RPE cultured in retentate fractions containing proteins of molecular weight less than 30 kD, it appears that proteins present in the low molecular weight fractions may have a negative effect on the cells. Molecular weight fractions of 100 kD and higher supported rapid initial RPE attachment in serum-free media. In this assay, it was not found that molecular weight fractions below 100 kD supported rapid attachment and spreading in serum-free media to any degree. Yet, as will be discussed in Example 12 below, two additional bioactive fractions were identified that contributed to cell survival on human submacular Bruch's membrane.

Thus, it appears that high molecular weight fractions (>100 kD) are important in initial RPE attachment and spreading in serum-free conditions.

TABLE 3

Fetal RPE behavior in serum-free BCE conditioned media of different molecular weights. RPE were seeded at the same density for all experiments. The effects of sfBCE-CM as media for attachment and growth, prepared by centrifugal filtration of different MW cut-offs (retentates above MW 3, 10, 30, 50, 100 kD and filtrates below MW 3, 10, 30, 50, 100 kD) are shown.

| Molecular weight fraction of sfBCE-CM | 1 Hour | Day-1 | Day-3 |
| --- | --- | --- | --- |
| Low MW (<3, 10, 30, or 50 kD) | Rounded | Rounded | Rounded |
| High MW (>3, 10, 30, or 50 kD) | 30-40% spread | >3 kD confluent, >10, 30, or 50 kD almost confluent to confluent with intercellular gaps | All confluent, >3 kD smallest cells with most vacuoles; >10 kD vacuoles, uniform cell size; >30 kD less vacuoles, uniform cell size; >50 kD mixed sizes, no vacuoles |
| sfBCE-CM (unfiltered control for above studies) | 30-40% spread | Confluent with intercellular gaps | Confluent, mixed sizes, few vacuoles |
| >100 kD | ~70% attached and spread | ~90% spread, some filopodia (more than seen in cells on BCE-ECM) | No observations |
| <100 kD | 80-90% attached, round | 20-30% spread, others are round, abundant filopodia | No observations |
| sfBCE-CM (unfiltered control for 100 kD cut-off studies) | ~70% attached and spread | ~90% spread, some filopodia | No observations |

Example 10

BCE Conditioned Media is Effective at Dilutions Up to 20×

Fetal RPE (passage-3, 526 cells/mm$^2$) were seeded onto non-tissue culture treated plastic in dilutions of serum-free BCE conditioned media (sfBCE-CM, 1:1 to 1:80 dilutions) to determine the maximum effective dilution of BCE-CM for support of initial RPE attachment and spreading. Negative control was cells seeded in serum-free DMEM. Results (Table 4). Support of attachment and spreading was seen in BCE-CM diluted up to 1:10 in serum-free DMEM. Cells in 1:20 and higher dilutions show increasingly poor attachment and morphology at day-1 after seeding.

TABLE 4

Fetal RPE behavior in diluted serum-free BCE-conditioned media.
Fetal RPE were suspended in different dilutions of serum-free
BCE-CM and seeded onto non-tissue culture treated dishes.

| Dilution of sfBCE-CM | 1 Hour | Day-1 |
|---|---|---|
| 1:1 | ~60-70% attached and spread | ~90-95% attached and well spread |
| 1:5 | ~60-70% attached and spread | ~90-95% attached and well spread |
| 1:10 | ~50-55% attached and spread | ~90% attached and well spread |
| 1:20 | ~50 attached and spread | ~60% attached, not as well spread as higher concentrations. Cells aggregated. |
| 1:40 | ~30-40% attached and spread | ~30-40% attached, variably spread. Cells aggregated; variable morphology with lamellipodia, filopodia. Some cells elongated, some not spread. |
| 1:80 | <5% attached and spread | <10% attached, some elongated minimal spreading. Cells aggregated; all of poor morphology with elongation, filopodia and lamellipodia. |
| DMEM (negative control) | Rounded, few spread | All rounded. |

Example 11

Figure 8:
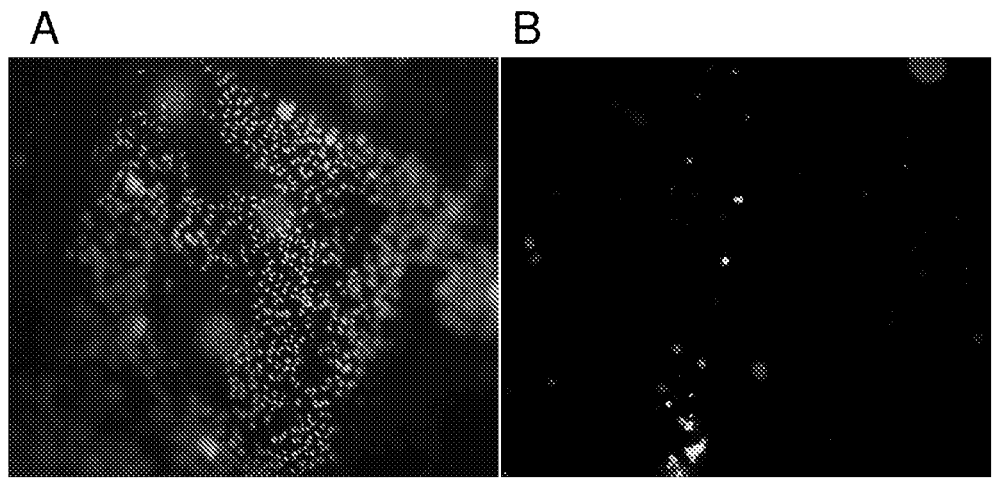
FIG. 8 illustrates that soaking a polycaprolactone (PCL) scaffold in serum-free BCE-conditioned media (BCE-CM) results in improved initial RPE attachment (A) compared to no BCE-CM treatment (B).

RPE can Attach and Grow on PCL Scaffolds 1052 fetal RPE/mm$^2$ were seeded onto 5 mm diameter PCL scaffolds and cultured for 1 day. To assess attachment onto the scaffolds, cell behavior was compared on scaffolds with no treatment (FIG. 8, B) vs. scaffold soaked in serum-free BCE conditioned media (sfBCE-CM, soaked for ~1 hr. at 37° C.) to allow protein adsorption (FIG. 8, A). Cells were cultured in DMEM or in sfBCE-CM. RPE were visualized on the scaffolds with calcein imaging. RPE appeared to attach only to scaffolds treated with or cultured in sfBCE-CM (Table 5, 1 day and FIG. 8). Greatest attachment and spreading were observed in cells seeded onto sfBCE-CM-soaked scaffolds.

Figure 9:
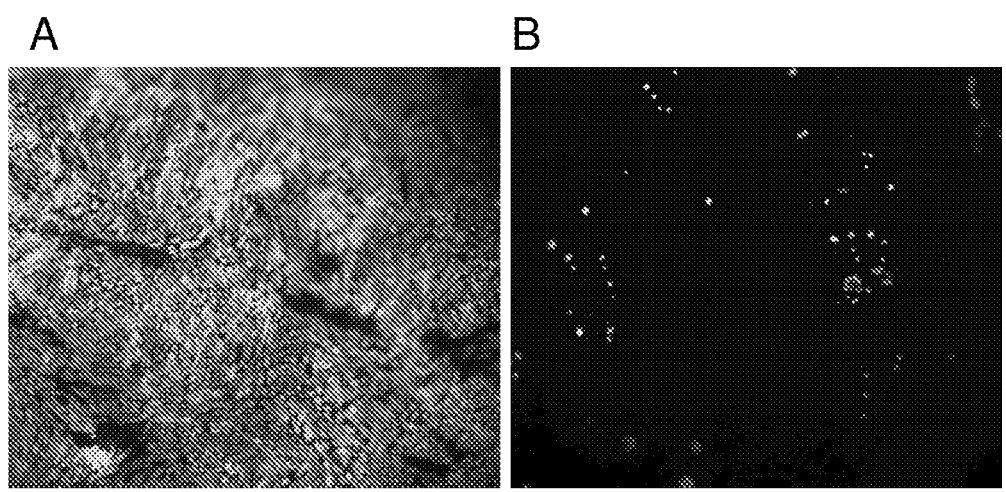
FIG. 9 illustrates that fetal RPE attachment and survival at 5 days is improved if the RPE are initially cultured in serum-free BCE-conditioned media for 2 days (A) vs. no BCE-CM treatment (B).

To determine whether cells could eventually adhere and spread on the scaffolds, scaffolds were exposed to sfBCE-CM by either soaking (FIG. 9, A), followed by cell seeding and culturing in DMEM for 2 days or using sfBCE-CM as media for 2 days. Controls were cells on untreated scaffolds in DMEM for 2 days (FIG. 9, B). Cultures were changed to RPE complete media (DMEM with 2 mM glutamine, 15% fetal bovine serum, 2.5 µg/ml fungizone, 0.05 mg/ml gentamicin, 1 ng/ml bFGF) after day 2 and cultured for 3 days. RPE were able to resurface the scaffolds only if the scaffold was pre-soaked in sfBCE-CM or sfBCE-CM was used as media for two days (see FIG. 9 and Table 5, 5 days).

To determine whether untreated scaffolds could support eventual resurfacing by RPE, assays were carried out to examine cell behavior on untreated scaffolds that were cultured in RPE complete media for 7 days. Cells were seeded at the same density as that onto Bruch's membrane (3164 cells/mm$^2$).

Figure 10:
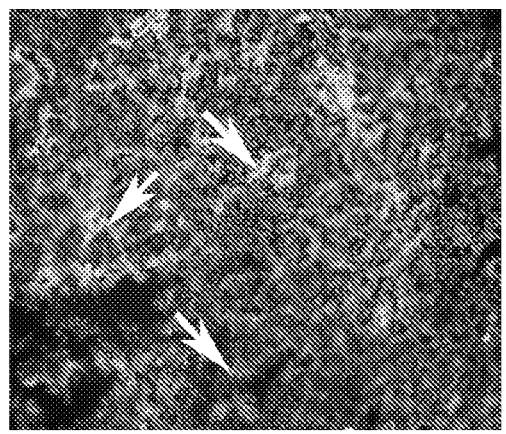
FIG. 10 illustrates that fetal RPE cultured in RPE complete media can attach and resurface an untreated PCL scaffold, but by 7 days the cells do not exhibit density arrest.

RPE fully resurfaced the untreated scaffold although the cells did not appear to density arrest by this time point (FIG. 10, arrows point to areas of multilayer formation). It was observe similar multilayer formation in RPE seeded onto tissue culture plastic and onto glass coverslips.

PCL scaffolds can support initial fetal RPE attachment and resurfacing if exposed to sfBCE-CM as a substrate coating the scaffold or as media overlying seeded cells. Although untreated scaffolds may support long-term survival of RPE in serum-containing media, modification of the scaffold or addition of ECM ligands may be necessary to support differentiated cell monolayers.

TABLE 5

Fetal RPE behavior on PCL scaffolds that were either untreated or soaked in serum-free BCE conditioned media (sfBCE-CM). For 1-day studies, cells on untreated scaffolds were cultured in sfBCE-CM or DMEM; cells on sfBCE-CM-soaked scaffolds were cultured in DMEM. For 5 day studies, cells were cultured on untreated or sfBCE-CM-soaked scaffolds for 2 days in DMEM or sfBCE-CM followed by media change to RPE complete media. For 7-day studies, untreated scaffolds were cultured in RPE complete media. Cell behavior on BCE-ECM-coated culture dishes (no scaffold controls) is included for day-1 and day-7 data for comparison.

| Time in Culture | Scaffold Treatment | Media | Cell Behavior |
|---|---|---|---|
| 1 day | None | DMEM | Few rounded cells |
|  | None | sfBCE-CM | Many cells, many are spread |
|  | sfBCE-CM | DMEM | Many cells, many are spread |
|  | BCE-ECM on plastic | DMEM | Many cells, majority are spread |
| 5 days | None | 2 d DMEM, 3 d RPE complete media | Few rounded cells |
|  | None | 2 d sfBCE-CM, 3 d RPE complete media | Fully resurfaced |

TABLE 5-continued

Fetal RPE behavior on PCL scaffolds that were either untreated or soaked in serum-free BCE conditioned media (sfBCE-CM). For 1-day studies, cells on untreated scaffolds were cultured in sfBCE-CM or DMEM; cells on sfBCE-CM-soaked scaffolds were cultured in DMEM. For 5 day studies, cells were cultured on untreated or sfBCE-CM-soaked scaffolds for 2 days in DMEM or sfBCE-CM followed by media change to RPE complete media. For 7-day studies, untreated scaffolds were cultured in RPE complete media. Cell behavior on BCE-ECM-coated culture dishes (no scaffold controls) is included for day-1 and day-7 data for comparison.

| Time in Culture | Scaffold Treatment | Media | Cell Behavior |
| --- | --- | --- | --- |
| | sfBCE-CM | 2 d DMEM, 3 d RPE complete media | Fully resurfaced |
| 7 days | None | RPE complete media | Fully resurfaced, some multi-layering |
| | BCE-ECM on plastic | RPE complete media | Fully resurfaced, monolayer |

Example 12

Identification of Bioactive Fractions that Support Cells on Human Aged and AMD Bruch's Membrane and Molecules of BCEC-CM In this example, BCEC-CM was fractionated to identify fractions having therapeutic activity. Briefly, BCEC-CM was collected from passage-2 BCEC after 72 hour exposure to Madin-Darby Bovine Kidney Maintenance Medium. The collected BCEC-CM was subject to ultrafiltration utilizing centrifugal filters of sizes ranging from 3 to 300 kDa. After separation, the fractions were tested for bioactivity by analyzing RPE survival on human submacular Bruch's membrane explants established from aged and AMD donor eyes. The protein component of the bioactive fraction was analyzed by mass spectrometry.

The bioactive fraction was identified as those molecules found in the filtrate generated after ultrafiltration using a 50 kDa filter. Mass spectrometry of the 50 kDa filtrate of two different BCEC-CM preparations identified 72 common secreted proteins, including 5 growth factors. Subfractionation of the 50 kDa filtrate showed decreased bioactivity in the filtrate after ultrafiltration utilizing a 30 kDa filter, indicating some bioactivity was contained in the 30-50 kDa fraction, and complete loss of bioactivity after removal of the 10-50 kDa fraction. Ultrafiltration of the 50 kDa fraction utilizing a 3 kDa filter also showed complete loss of activity in the retentate (3 kDa-50 kDa), indicating that bioactivity was present in the <3 kDa filtrate.

Bioactive molecules were found in a fraction generated by molecular weight cut off filtration. This bioactive fraction is comprised of molecules found in the fraction generated after filtration using a 50 kDa filter. Bioactive molecules supporting long-term survival of cells on aged and AMD submacular Bruch's membrane are found in several subfractions of the 50 kDa fraction: a low molecular weight subfraction (below 3 kDa) and a 10-50 kDa subfraction. This finding indicates there are at least two bioactive molecules in BCEC-CM. Subsequent mass spectrometry analysis of the protein component of the 50 kDa fraction identified four candidate growth factors (proteins that stimulate cells in a variety of ways including growth stimulation, cell death prevention, and cell functionality and maturity acquisition). Molecules found in the low molecular weight fraction support rapid cell attachment, spreading, and growth in cell culture.

Figure 11:
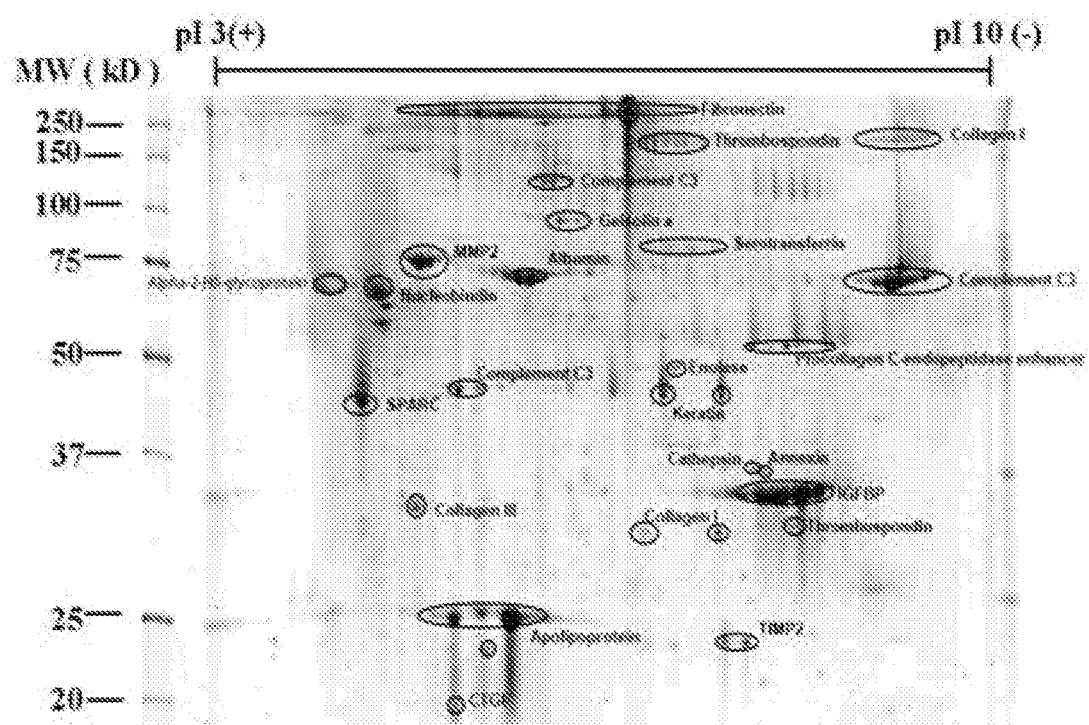
FIG. 11 shows a two-dimensional gel with spot identification of BCEC-CM (uncut, consisting of all fractions).
Figure 12:
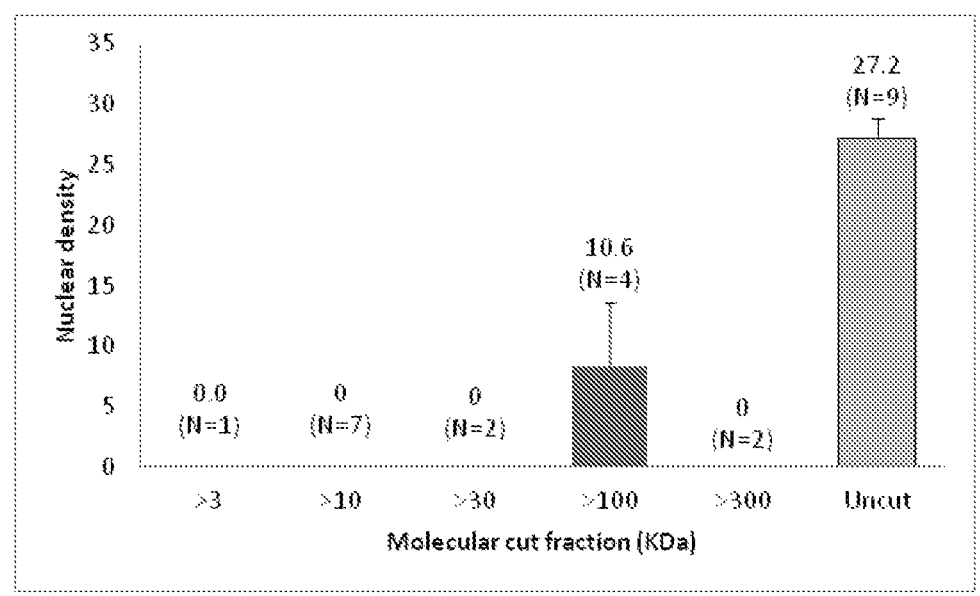
FIG. 12 provides graphical analysis of cell survival (nuclear density) on aged and AMD Bruch's membrane in molecular cut filtrates utilizing 3-300 kDa filters: the nuclear densities after culture in the retentates (comprising molecules above the filter size) are compared to BCEC-CM that has not be subject to ultrafiltration (uncut).
Figure 13:
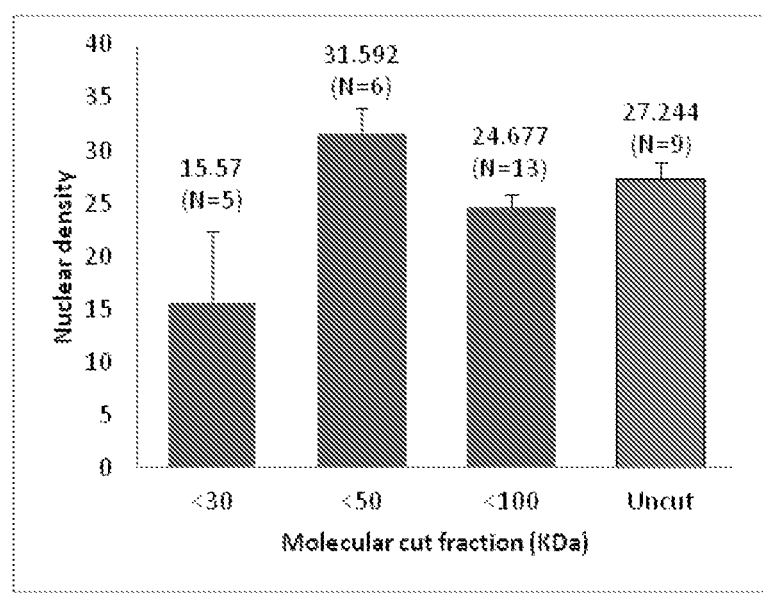
FIG. 13 represents results of cell survival (nuclear density) on aged and AMD Bruch's membrane in molecular cut filtrates utilizing 30-100 kDa filters. The nuclear density after culture in the filtrates is compared to BCEC-CM that has not been subject to ultrafiltration (uncut).
Figure 14:
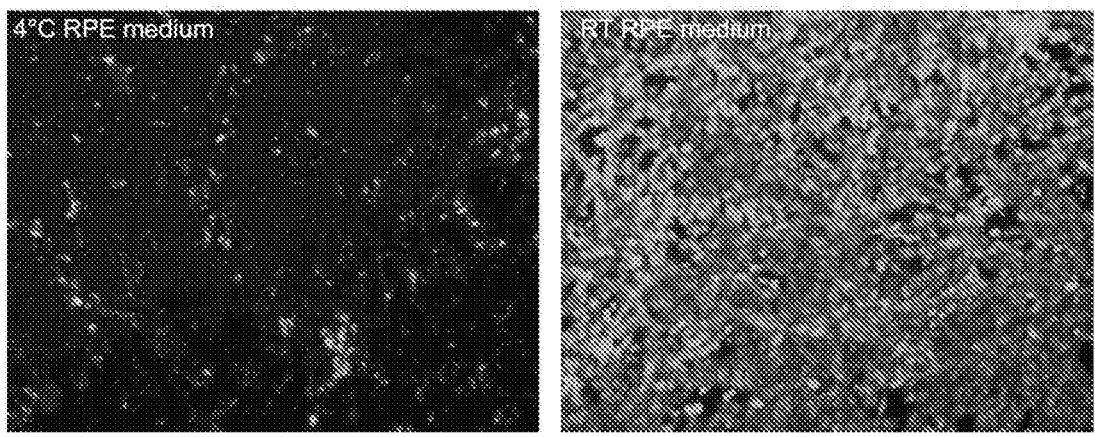
FIG. 14 shows comparison of cell viability at day-3 in an RPE medium at 4° C. (left) and room temperature (RT, right), where Live/dead tests performed at day-3 showed more cell death in the RPE medium at 4° C. than at room temperature (red: ethidium homodimer staining of dead nuclei; green: calcein staining of live cells). There did not appear to be any intact cells remaining in the 4° C. RPE medium well after staining.
Figure 15:
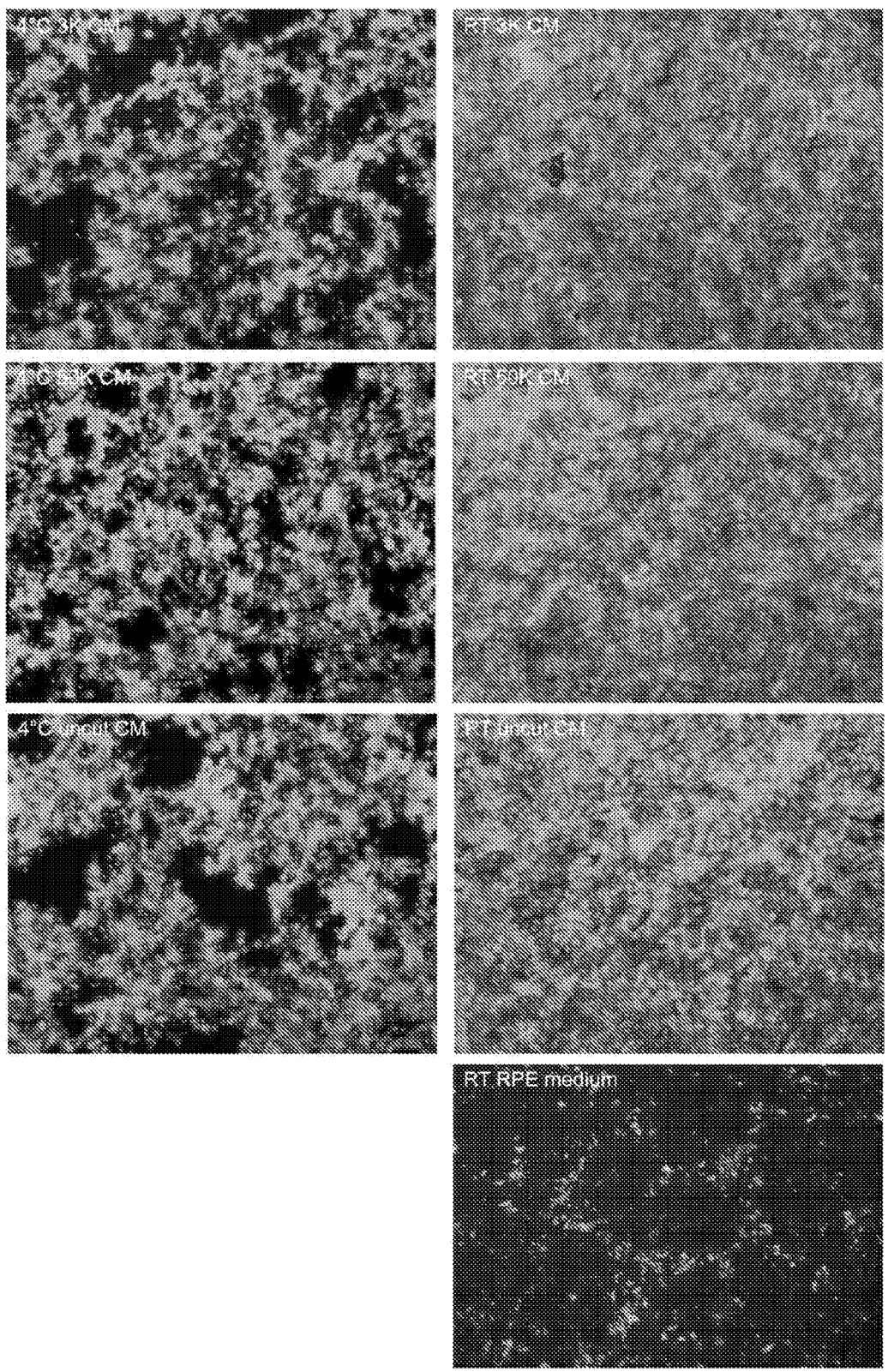
FIG. 15 shows cell viability at day-7 in CM, CM molecular cut filtrates, and RPE medium at 4° C. (left column) and room temperature (right column); at day-7, the majority of cells remaining after live/dead staining were dead in CM and CM fractions at 4° C. The majority of cells in CM and CM fractions at room temperature were alive and confluent with small defects while only cell debris remain in the well stored in the RPE medium.

Preliminary two-dimensional gel and mass spectrometry spot ID analysis (see FIG. 11, Table 6 below) showed abundant large molecular weight extracellular matrix ligands (collagens and fibronectin). These molecules (specifically, fibronectin) have been shown to support RPE attachment in cell culture and to support initial attachment on Bruch's membrane. To determine if high molecular weight components contribute to cell survival on Bruch's membrane, RPE survival was analyzed in large molecular weight retentates. Molecular cut removal of low molecular weight components showed little or no bioactivity in the retentate fractions (see FIG. 12). The results of testing the high molecular weight retentates (FIG. 12) indicate that a low molecular weight fraction in the 3 kDa filter filtrate must be present in order for BCEC-CM to show complete bioactivity.

TABLE 6

Proteins Obtained by Molecular Cut Filtration and Identified by Mass Spectrometry

| IPI ID | Protein | MW | Gene | Function |
| --- | --- | --- | --- | --- |
| IPI00691126 | C—X—C motif chernokine 6 | 12 | CXCL5 | cytokine |
| IPI00699064 | DKK3 protein | 38 | DKK3 | cytokine |
| IPI00714868 | Protein FAM3C | 25 | FAM3C | cytokine |
| IPI00839037 | Uncharacterized protein | 13 | PF4 | cytokine |
| IPI00696930 | Uncharacterized protein | 55 | EFEMP1 | enzyme |
| IPI00702154 | Lysyl oxidase-like 1 | 65 | LOXL1 | enzyme |
| IPI00710136 | Angiogenin-1 | 17 | ANG | enzyme |
| IPI00760446 | Ribonuclease, RNase A family, 4 | 17 | RNASE4 | enzyme |
| IPI00686503 | Platelet-derived growth factor subunit | 24 | PDGFA | growth factor |
| IPI00698668 | Connective tissue growth factor | 38 | CTGF | g owth factor |
| IPI00706240 | growth arrest-specific 6 | 74 | GAS6 | growth factor |
| IPI00731393 | PDGFD protein | 42 | PDGFD | growth factor |

TABLE 6-continued

Proteins Obtained by Molecular Cut Filtration and Identified by Mass Spectrometry

| IPI ID | Protein | MW | Gene | Function |
|---|---|---|---|---|
| IPI01018572 | Insulin-like growth factor I variant 2 | 21 | IGF-1 | growth factor |
| IPI00714018 | Insulin-like growth factor I | 17 | | growth factor |
| IPI00685095 | Cystatin-C | 16 | CST3 | other |
| IPI00685504 | Alpha 1 type VIII collagen (Fragment) | 73 | COL8A1 | other |
| IPI00688802 | Uncharacterized protein | 136 | NID1 | other |
| IPI00688875 | Follistatin-related protein 3 | 28 | FSTL3 | other |
| IPI00690094 | Galectin-1 | 15 | LGALS1 | other |
| IPI00692839 | Uncharacterized protein | 44 | | other |
| IPI00698975 | SPARC | 35 | SPARC | other |
| IPI00702294 | Plasminogen activator inhibitor 1 | 45 | | other |
| IPI00704150 | Vitamin K-dependent protein S | 75 | PROS1 | other |
| IPI00705697 | Insulin-like growth factor-binding | 34 | IGFBP2 | other |
| IPI00706624 | Procollagen C-endopeptidase | 48 | PCOLCE | other |
| IPI00707101 | Alpha-2-HS-glycoprotein | 38 | AHSG | other |
| IPI00707467 | Follistatin-related protein 1 | 35 | FSTL1 | other |
| IPI00707932 | collagen alpha-2(VIII) chain | 67 | COL8A2 | other |
| IPI00708244 | Collagen alpha-2(I) chain | 129 | COL1A2 | other |
| IPI00708990 | Uncharacterized protein | 148 | LTBP1 | other |
| IPI00709059 | Angiopoietin-related protein 7 | 39 | ANGPTL7 | other |
| IPI00709084 | Metalloproteinase inhibitor 1 | 23 | TIMP1 | other |
| IPI00710025 | Factor XIIa inhibitor | 52 | | other |
| IPI00710385 | Prolargin | 44 | PRELP | other |
| IPI00710453 | Matrix Gla protein | 12 | MGP | other |
| IPI00711862 | Epididymal secretory protein E1 | 17 | NPC2 | other |
| IPI00712084 | Thrombospondin-1 | 130 | THBS1 | other |
| IPI00712366 | Fibromodulin | 43 | FMOD | other |
| IPI00712524 | collagen, type IV, alpha 2, partial | 165 | COL4A2 | other |
| IPI00713428 | ADM | 21 | ADM | other |
| IPI00713573 | Uncharacterized protein | 109 | COL6A1 | other |
| IPI00716121 | Pigment epithelium-derived factor | 46 | | other |
| IPI00718311 | Isoform 1 of Proactivator polypeptide | 58 | PSAP | other |
| IPI00718620 | Insulin-like growth factor-binding | 28 | IGFBP4 | other |
| IPI00730859 | Uncharacterized protein | 139 | LTBP3 | other |
| IPI00731756 | Uncharacterized protein | 24 | SCG5 | other |
| IPI00824031 | LTBP1 protein | 147 | LTBP1 | other |
| IPI00838716 | Uncharacterized protein (Fragment) | 102 | CHRD | other |
| IPI00840999 | PCSK1N protein | 27 | PCSK1N | other |
| IPI00883474 | gelsolin a | 86 | GSN | other |
| IPI00905045 | collagen alpha-1(XI) chain | 182 | COL11A1 | other |
| IPI00906401 | Uncharacterized protein (Fragment) | 25 | IGFBP6 | other |
| IPI00733988 | collagen type 5 alpha 1-like | 30 | | other ECM |
| IPI00716123 | Mimecan | 34 | OGN | other ECM |
| IPI00685447 | 72 type IV collagenase | 74 | MMP2 | peptidase |
| IPI00705266 | Uncharacterized protein | 102 | ADAMTS5 | peptidase |
| IPI00712538 | HtrA serine peptidase 1 | 67 | HTRA1 | peptidase |
| IPI00713459 | A disintegrin and metalloproteinase | 136 | ADAMTS3 | peptidase |
| IPI00713505 | Complement C3 (Fragment) | 187 | C3 | peptidase |
| IPI00714873 | Serine protease 23 | 42 | PRSS23 | peptidase |
| IPI01004181 | bone morphogenetic protein 1-like | 107 | BMP1 | peptidase |
| IPI00717574 | Carboxypeptidase E | 53 | | peptidase |
| IPI00689362 | Transthyretin | 16 | TTR | transporter |
| IPI00690534 | Serotransferrin | 78 | TF | transporter |
| IPI00708398 | Uncharacterized protein | 70 | ALB | transporter |
| IPI00712693 | Apolipoprotein E | 36 | APOE | transporter |
| IPI00713780 | Uncharacterized protein | 24 | APOD | transporter |
| IPI00715548 | Apolipoprotein A-I | 30 | APOA1 | transporter |
| IPI00866855 | IGFBP7 protein | 29 | IGFBP7 | transporter |
| IPI00697184 | retinol-binding protein 4 | 23 | Secreted | transporter |
| IPI00867435 | NID2 protein | 143 | Secreted? | other |

Testing of the filtrates revealed complete bioactivity can be retained in filtrates utilizing the 50 kDa filter, indicating that the bioactivity is comprised of molecules of molecular weight at or near 50 kDa and lower. Although there appears to be a trend towards decreased nuclear density in the <30 kDa filtrate, the difference is not significant (Kruskal-Wallis One Way Analysis of Variance on Ranks, P=0.092).

The results of these examples indicate that there are a minimum of two bioactive molecules in BCEC-CM, one found in the <3 kDa filtrate and one found in the 10-50 kDa fraction and that bioactive molecules in both fractions must be present to ensure cell survival on Bruch's membrane.

Example 13

Differentiation Medium for RPE

In this example, studies were performed to determine whether fetal RPE mature more rapidly in BCEC-CM compared to standard RPE medium, where onset of maturity was based on mRNA expression of late RPE differentiation markers, bestrophin and RPE65. More specifically, fetal RPE were seeded at a high seeding density (3164 cells/mm$^2$) onto BCEC-ECM coated tissue culture dishes and maintained in culture for 21 days in the aforementioned RPE medium or BCEC-CM. The media were changed 3×/week. At day-21, the cells were harvested off the tissue culture dishes for real time PCR mRNA analysis of bestrophin and RPE65.

It was found that the cells cultured in BCEC-CM appeared to have patches of cells that looked more mature (morphologically) than cells in the RPE medium. In contrast, the cells in the RPE medium appeared to be more uniform in appearance. The cells cultured in BCEC-CM expressed approximately 10× more RPE65 and 50× more bestrophin mRNA than the cells cultured in the RPE medium.

Example 14

Bovine Corneal Endothelial Cell Conditioned Medium as Storage Medium

In this example, assays were carried out to examine the properties of CM in preserving confluent fetal RPE monolayers under conditions likely to occur during shipping and storage of cells attached to a substrate prior to use in patients.

a. Cell Behavior after Storage in RPE Medium, Optisol, and CM (Batch 34AB)

In this assay, the substrate was tissue culture plastic (TCP) or TCP coated with bovine corneal endothelial cell extracellular matrix (ECM). Optisol is a medium developed for corneal storage. Passage 2 fetal RPE were seeded on ECM or directly on TCP and cultured in standard RPE medium for 11 days. At the start of the storage period, cells were placed in one of the following three media:

(i) RPE medium: DMEM base medium (HEPES, inorganic salts, amino acids, vitamins, glucose, sodium pyruvate), bFGF, fetal bovine serum, glutamine, gentamicin, and fungizone;

(ii) Optisol (Bausch and Lomb, Inc., proprietary cornea preservation medium) "Optisol base powder", chondroitin sulfate, dextran, sodium bicarbonate, antibiotics and fungizone, sodium pyruvate, glutamine, mercaptoethanol, and amino acids; and (iii) CM: MDBK-MM base medium (Sigma Aldrich proprietary formulation including HEPES, human recombinant peptides (insulin and possibly others), amino acids, and sodium bicarbonate), CM harvested after 3 day exposure of MDBK-MM to confluent bovine corneal endothelial cell cultures.

Experiments were carried out at 4° C. (refrigerator) and at room temperature in sealed culture plates or dishes with no media change. Although it is unlikely a surgical site will have a 37° C. CO$_2$ incubator suitable for storing cells for patient use, the viability of storing fetal RPE was compared in such an incubator. In these preliminary studies, the onset of cell death was estimated by initial appearance of defects in the RPE monolayer.

TABLE 7

Onset of cell death after storage in Optisol, CM, or RPE medium

| Substrate/temperature | Optisol | CM | RPE |
|---|---|---|---|
| TCP/4° C. | <7 days | ~21 days | ~21 days |
| TCP/RT | <3 days | >21 days | <7 days |
| ECM/4° C. | <10 days | <10 days | <10 days |
| ECM/RT | | <3 days | <3 days |
| ECM/37° C. (unsealed) | | <7 days | <7 days |
| TCP/37° C. (unsealed) | | 14-<21 days | 14-21 days |

The results were shown in Table 7. It was found that Optisol was relatively poor at preserving RPE viability. All cells stored in Optisol were of abnormal morphology at early time points. Both CM and RPE media generally maintained fetal RPE viability to a similar degree except CM was better at preserving RPE at room temperature if the cells were on tissue culture plastic. Fetal RPE cultured on an extracellular matrix that supports rapid cell attachment and growth in cell culture, showed poor viability regardless of the storage medium.

b. Storage of Confluent RPE Cultures in CM (Batch 58) Molecular Cut Fractions

In this assay, confluent fetal RPE cultures (passage 3 or 4, 7-13 days in culture) grown on tissue culture plastic were stored at room temperature or 4° C. in sealed 48 well plates with no medium change for up to 7 days. The storage media were RPE medium and CM, including 3 kD and 50 kD CM molecular cut filtrates. Live/death assessment was performed at day-3 or day-7. The results are shown in Table 8 below, where the values reflect the days in storage when loss of cells in the RPE monolayer was observed.

TABLE 8

Onset of cell death after storage in RPE medium and CM molecular cut fractions

| Storage medium | 4° C. | RT |
|---|---|---|
| RPE | 3-4 D | 3-4 D |
| 3K CM | 4 D-<7 D | >7 D |
| 50K CM | 4 D-<7 D | 7 D->7 D |
| Uncut CM | 4 D-<7 D | >7 D |

It was found that onset of cell death was sooner than in the previous study (Table 7 vs. Table 8), possibly due to variability between CM batches and/or the fetal RPE passage number and time in culture. An additional consideration for comparisons between experiments for storage at room temperature is the variability in ambient temperature. RPE medium effective storage times were consistently short for both temperatures. Storage times in CM, including CM fractions were longer than RPE for storage at room temperature. The 3 kD and 50 kD filtrates storage times were similar to CM that had not be subject to molecular cut filtration ("uncut CM").

Example 15

Storage of Cell Suspensions

In this example, assays were performed to examine the ability of CM for shipping and storing fresh cell suspensions on wet ice or ambient temperature. Such ability offers an alternative to using frozen cells for patient transplants. Frozen cells require storage in liquid nitrogen, shipment on dry ice or under liquid nitrogen, and thaw, rinse, and resuspension in delivery vehicle for patient use. Cells recovered from thaw attach and grow slower than fresh cells with some cell death occurring from freezing and subsequent manipulations. Ideally, fresh cells would be stored in a solution similar to that of the delivery vehicle so no or few manipulations are required.

a. Cell Viability after Storage in CM Vs. RPE Medium

Previous studies indicated that RPE undergo apoptosis if not attached to a suitable substrate by 24 hours (Tezel et al. *Graefes Arch Clin Exp Ophthalmol* 1997; 235:41-47). In this assay, studies were performed to determine if cell suspensions can retain any degree of viability after storage.

Briefly, fetal RPE cell suspensions (100,000 in 100 ul) in the CM or RPE medium (contains fetal bovine serum, glutamine, and basic fibroblast growth factor) were placed in sealed microfuge tubes. The tubes were stored at room temperature or 4° C. for 1, 2, 3, or 7 days. At the end of the storage period, the numbers of live and dead cells were determined by trypan blue staining and the remaining cells plated on tissue culture plates and cultured in fresh storage medium to assess viability.

Figure 16:
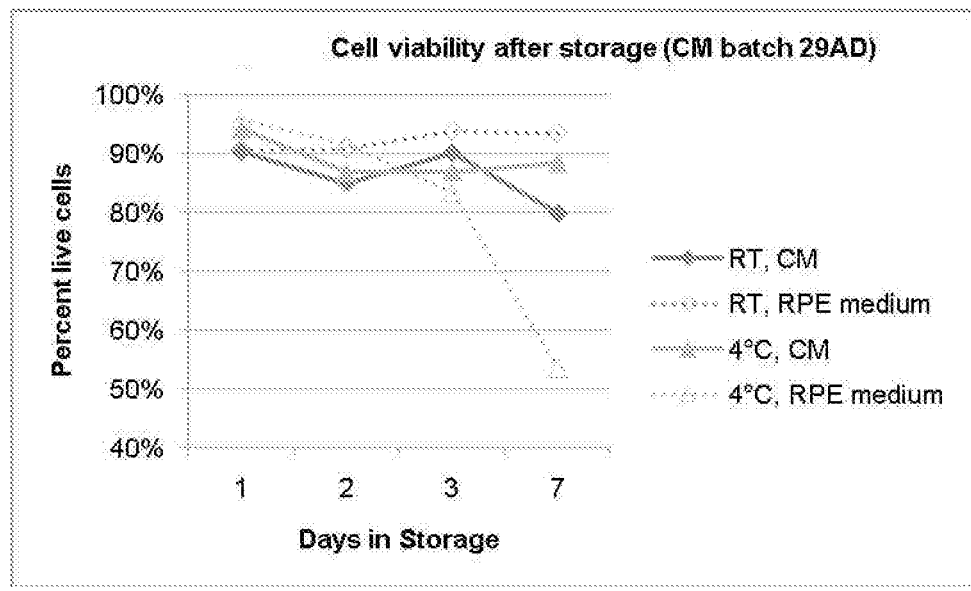
FIG. 16 shows cell viability after storage using CM batch 29AD.

FIG. 16 illustrates cell viability, expressed as the percent of live cells at the end of each storage period, for fetal RPE suspensions in CM or RPE medium at room temperature (RT) or 4° C. The results showed that fetal RPE suspensions can retain a high degree of viability when stored in sealed microfuge tubes at 4° C. and room temperature for up to 3 days in storage. At 7 days in storage, cells stored in the RPE medium at 4° C. showed a marked drop in percent of live cells. At room temperature, cells were clumped in both media, making viability assessment difficult. Harvested cells from each storage time showed rapid attachment, spreading, and growth when cultured on tissue culture plastic. All cultures were confluent by day-7 in culture except for the 7-day storage, room temperature cells that were stored in CM. These data show that it is possible to store cell suspensions for a short period of time with little loss in cell viability.

b. Storage of Cell Suspensions in Molecular Cut Fractions of CM (CM Batch 58)

The studies of part a in Example 14 above were repeated with additional storage in 3 kD and 50 kD CM molecular cut filtrates. To determine the change in cell numbers with time in culture, time 0 viability counts were performed for each tube of cells to be stored. To better assess cell numbers in tubes stored at room temperature, cell clumps were treated with trypsin for the 3 and 7 day storage time points. Cell viabilities in all media were below the levels measured at time 0 at days 3 and 7.

Figure 17:
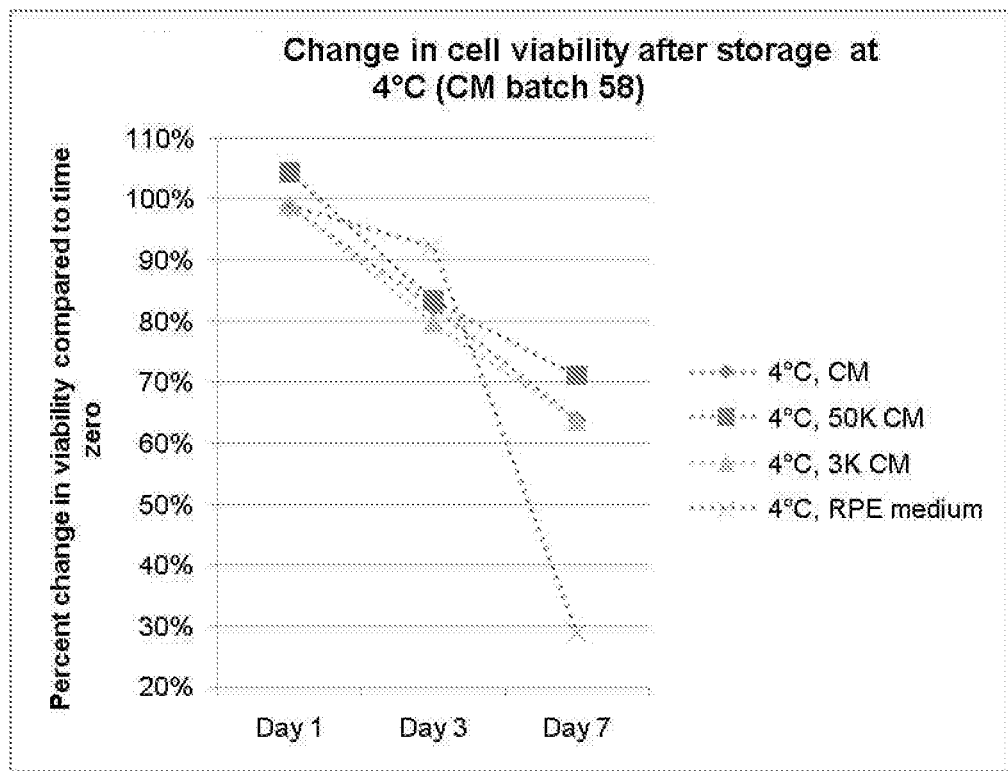
FIG. 17 shows change in cell viability after storage at 4° C. using CM batch 58.
Figure 21:
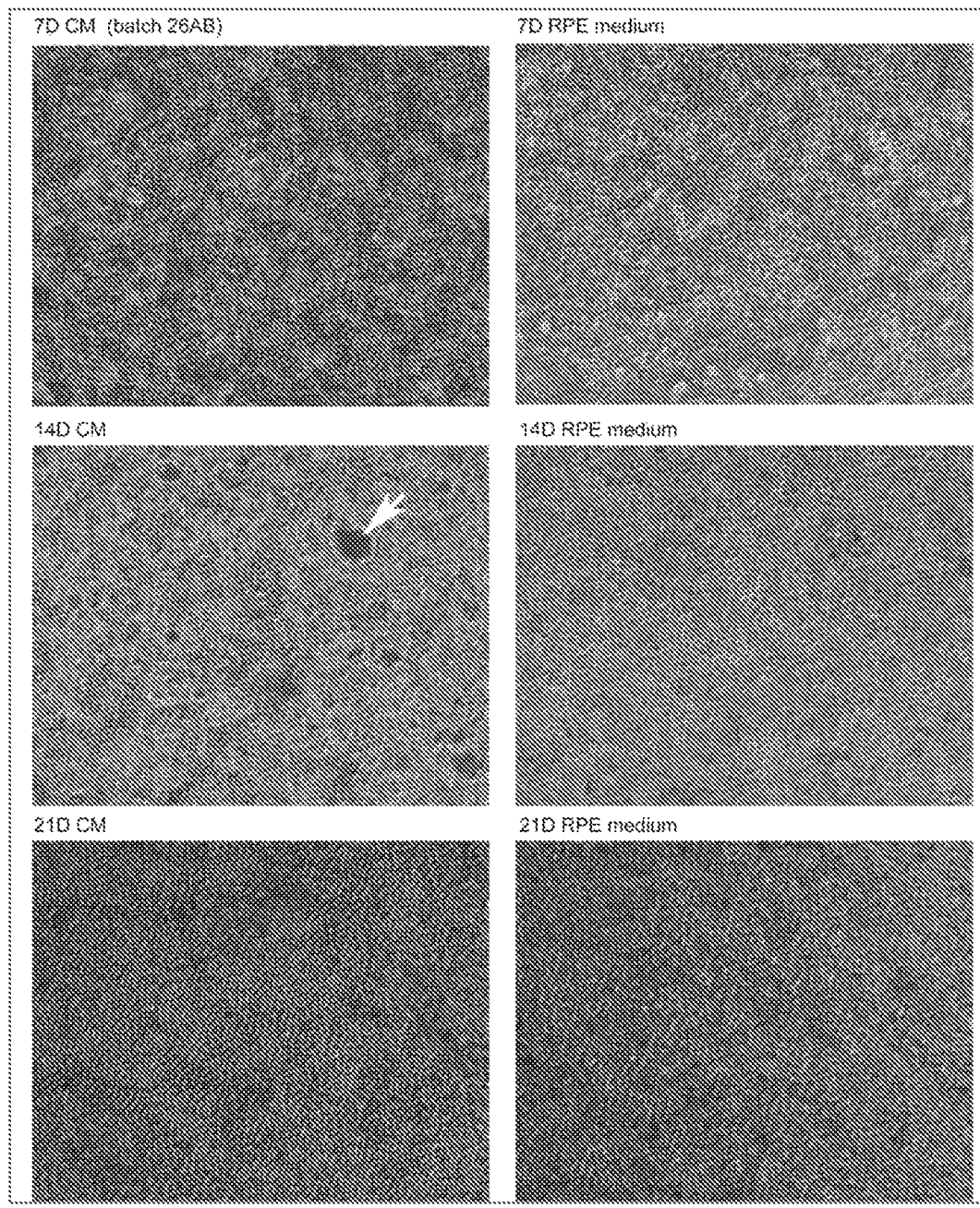
FIG. 21 shows comparison of cell behavior after seeding and culture on tissue culture plastic in CM (left column) vs. RPE (right column) medium with media change 3×/week; the images were taken at approximately the same location for all 3 time points.

It was found that, consistent with the previous experiment (FIG. 16), poorest viability was observed in cells stored at 4° C. in the RPE medium (FIG. 17). At room temperature storage, all cells maintained viability levels above that measured at time zero (FIG. 18). Cells stored in CM and CM fractions showed better preservation of live cells than those stored in RPE medium at 4° C. (FIG. 19). The change in cell numbers in the RPE medium at day-7 is consistent with the drop in cell viability at this time point. The day-1 data are not shown since the counting method was not the same as days 3 and 7. The increase in live cell numbers at day-3 compared to time 0 indicated that the cells were dividing. Cells in 50 kD CM appear to maintain cell division at day-7.

As shown in FIG. 20, storage in 3 kD CM and the RPE medium at room temperature showed increased number of live cells at day-1 while live cell numbers dropped to similar levels in 50 kD CM and uncut CM. Similar to storage at 4° C., cells in the RPE medium show a drop in live cells with time in culture. The cells in 50 kD CM appeared to be dividing during 3 and 7 day storage periods with number of live cells at day-7 well above the time 0 levels. The cells in uncut CM showed a marked rise in the number of live cells at day-7 compared to time 0 levels.

Example 16

CM as Culture Medium

In this example, assays were performed to examine whether CM could offer an advantage over a standard RPE culture medium as a defined, serum-free medium.

a. Comparison of Cell Behavior in CM Vs. RPE Medium

Studies of fetal RPE behavior (when cultured in CM vs. RPE medium) show that CM can support fetal RPE to some degree when cultured directly on tissue culture plastic. It was found that cells in CM rapidly attached, spread, and grew to confluence. The ability of CM to support cells in long-term cultures is highly variable and may depend on the batch of CM and/or the fetal RPE starting culture (passage number, length of time in culture prior to harvest). In some CM cultures, some cell death occurred between day-14 and day-21. In other cases, CM cultures were similar in size at 14 and 21 days although the cells may be more pigmented at day-21.

Lastly, it was found that some CM supported cells to a higher degree with mature cells at day-21 compared to day-14. In RPE medium, some cell death and/or cessation of cell division appeared to occur between day-7 and day-21 in some cultures as the cultures were similar in appearance or the cells are larger at day-21. Additionally, the presence of pigmented clumps of dead cells could be seen in many cultures at these time points. In comparing parallel cultures of CM and RPE medium, CM appeared to preserve cell viability longer than RPE medium. Studies are in progress to determine cell behavior in CM vs. RPE medium on single human ECM proteins (e.g. laminin, collagen I, collagen IV).

The set of figures in FIGS. 21A-F are parallel cultures at different culture times. It was found that fetal RPE attached and spread rapidly in early cultures. As shown in the figures, by 7 days, both cultures appeared similar. At day-14, the appearance of mature RPE could be seen in both cultures; some of the cells were very small and appeared to have rounded (columnar) vs. flat surfaces. There appeared to be more of these highly differentiated cells in the CM culture vs. RPE medium culture. The white arrow points to a cluster of highly pigmented RPE. These could be dead/dying RPE that are shed from the culture. By 21 days, the cells were larger in both media, indicating that some cell death occurred.

b. Culture with Limited Viability of RPE in RPE Medium

In this example, additional assays were performed to examine effects of CM and the RPE medium on cell behavior.

Figure 22:
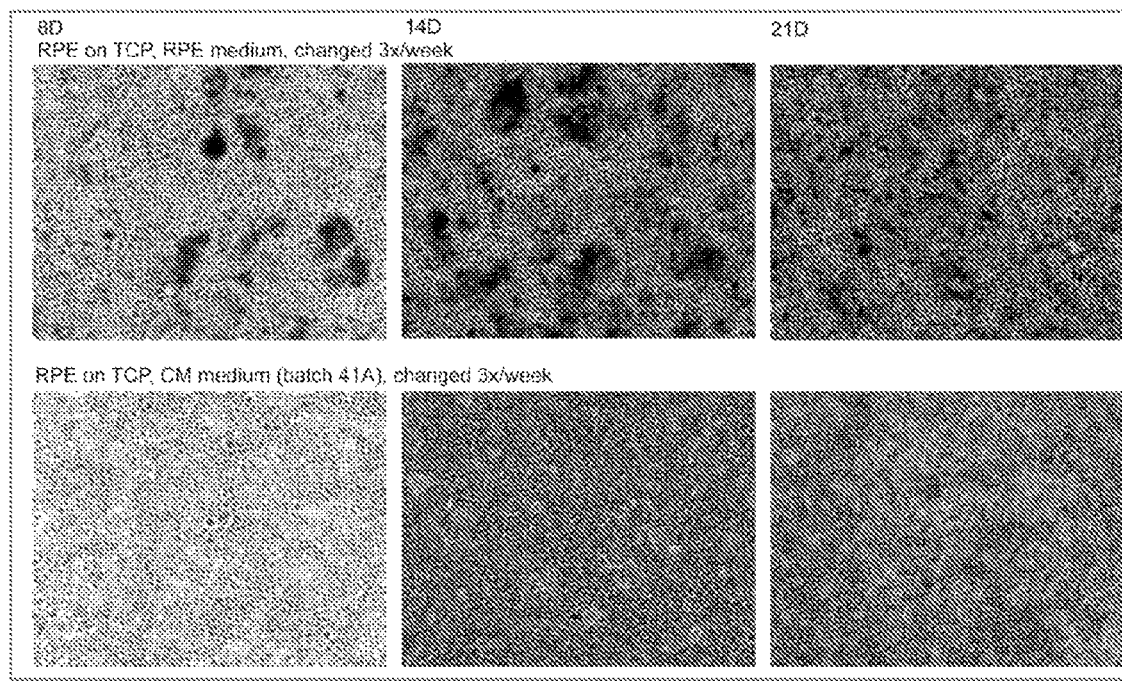
FIG. 22 shows comparison of cell behavior after seeding and culture on tissue culture plastic in RPE medium (top row) vs. CM (bottom row) with media change 3×/week.
Figure 23:
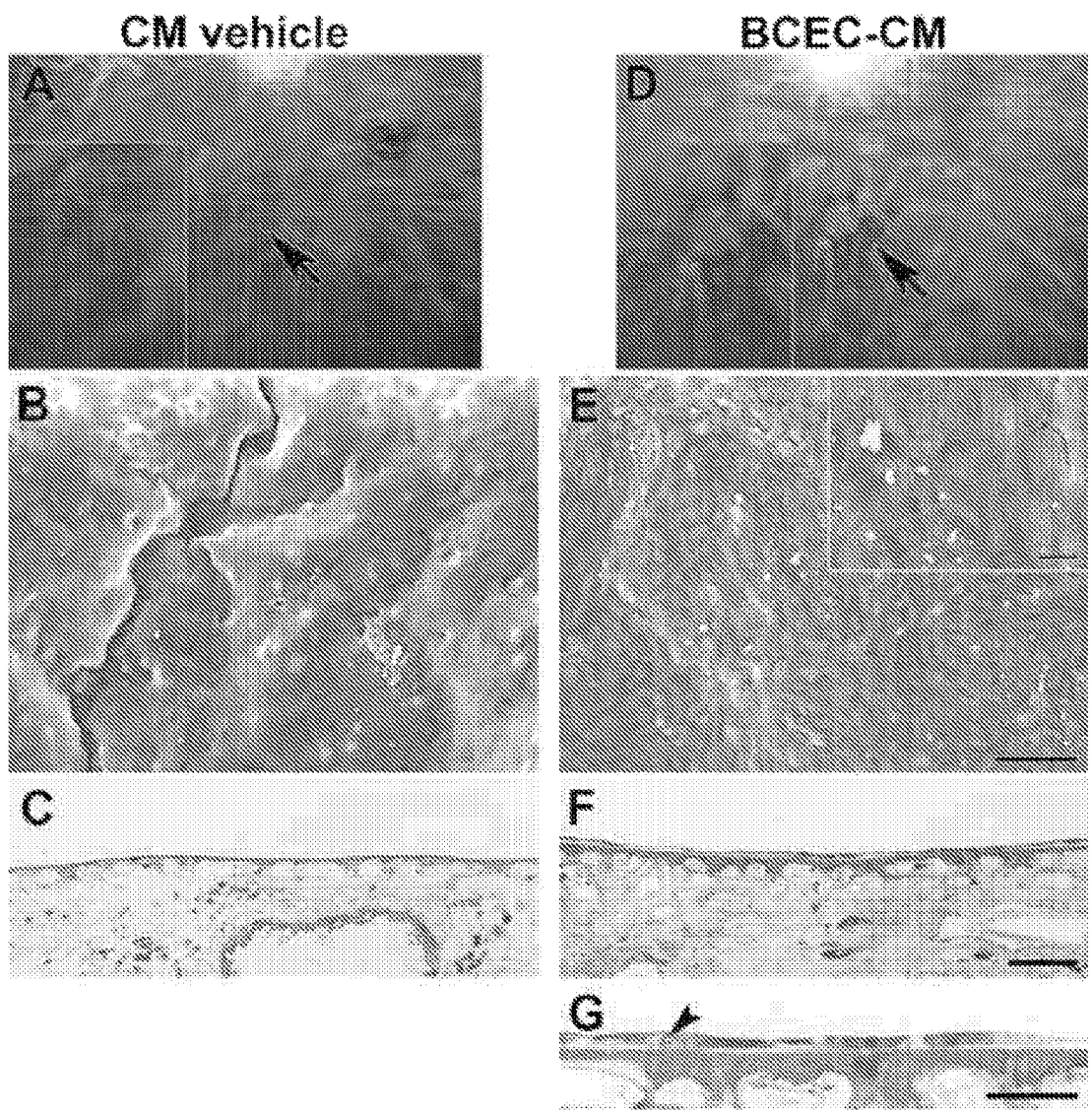
FIGS. 23A-G show paired submacular explants from a 74-year-old female with soft drusen, seeded with hES-RPE. CM vehicle: (A) Postmortem clinical photograph shows soft drusen (arrow) in the macula. Inset is a higher magnification image of the area indicated by the arrow. The drusen are not easily visualized in this photomicrograph due to post mortem changes. (B and C) No intact cells are seen on the cultured explant. BCEC-CM: (D) Arrow points to a patch of confluent soft drusen in the macula of the fellow eye, shown in the high magnification inset. (E) Cells almost fully resurface the explant with small defects in coverage. Cells are variable in size and shape. Insert. Cells are generally flat with most exhibiting short apical processes on their surfaces. (F and G) Cells resurfacing the explant are in a monolayer of very flat and elongate cells. Arrowhead (G) points to cell containing vesicles. CM vehicle nuclear density (ND), 0; BCEC-CM ND, 19.90±0.35. Scale bar: (E) 100 µm; (E, inset) 20 µm; (F) 50 µm; (G) 20 µm. Toluidine blue staining.

In a set of parallel cultures (see FIG. 22), RPE in the RPE medium on tissue culture plastic showed some degree of cell death as early as 8 days in culture with the appearance of pigmented clusters on top of the RPE monolayer. The cells in the RPE medium were of similar size at all three time points. The RPE appeared to be smaller when cultured in CM indicating cell division occurred.

c. Expression of RPE Differentiation Markers in Cells Cultured in CM Vs. RPE Medium Assays were carried out to examine mRNA expression levels 21 days after seeding on tissue culture plastic utilizing a different CM batch than that used in Example 13. It was found that the fetal RPE cultured in CM expressed 9.6× more Bestrophin and 1.28× more RPE65 than the cells cultured in the RPE medium. Western blot also showed Bestrophin protein present as strong bands in 14- and 21-day CM cultures with faint (if present at all) bands in parallel RPE medium cultures at the same time points.

d. Culture of RPE in 3 kD Filtrate

While CM low molecular weight components alone do not support cells on Bruch's membrane, the 3 kDa filtrate alone supported attachment and spreading of human fetal RPE on human collagen I, a major component of the inner collagenous layer of Bruch's membrane, as well as on uncoated tissue culture plastic although not to the same degree.

On collagen I, cell spreading was observed initially by day-1 and by day-3 in culture, ≥50% of RPE are spread. Cells reached confluence by 3 days or later, depending on the CM batch. On tissue culture plastic, RPE attachment, spreading, and growth occurred but, depending on CM batch, to a lesser degree than was observed on collagen I, with the onset of spreading later on tissue culture plastic. The 10-50 kDa fraction alone supported only limited attachment and spreading on both tissue culture plastic and collagen I at early times in culture with only a few elongate cells observed at day-3. Addition of the 3 kDa filtrate to this fraction restored the activity to the level observed in <50 kDa filtrate. These studies indicate that the 3 kDa filtrate contains bioactive molecules that are necessary for cell attachment and growth in long-term cell culture.

Example 17

Enhancing Cell Survival on Bruch's Membrane in Eyes Affected by Age and AMD

In this example, assays were carried out to determine whether BCEC-CM can support transplanted cells on aged and AMD Bruch's membrane (BM).

Currently, no proved treatment options exist for patients with geographic atrophy, an advanced form of AMD. For selected patients with extensive drusen or geographic atrophy threatening the fovea, cell transplants might prevent central vision loss through replacement of dysfunctional or dead RPE cells. Anti-vascular endothelial growth factor therapy is currently the best treatment available for AMD-associated CNVs, but randomized studies indicate that only 25-40% of treated patients experience at least moderate visual improvement. Thus, even today, a significant number of patients become blind despite the availability of pathway-based therapy for AMD-associated CNVs. If cell transplants could prevent CNV development or rescue photoreceptors following CNV excision, then these transplants also might have an impact on CNV-related blindness.

A major obstacle to the success of RPE transplants in AMD patients is the failure of transplanted RPE cells to survive and become functional in the diseased AMD eye. RPE transplantation in patients with AMD (atrophic and neovascular) typically has produced limited visual recovery regardless of the type of cell transplanted (e.g., autologous or allogeneic, adult or fetal RPE) or whether the cells are transplanted with or without choroid. In contrast, RPE transplantation in animal models of retinal degeneration has been proved to rescue photoreceptors and preserve visual acuity. Although animal studies validate cell transplantation as a means of achieving photoreceptor rescue, an important distinction between humans with AMD and laboratory animals in which RPE transplantation has been successful is the age- and AMD-related modifications of the surface on which human RPE reside in situ (i.e., Bruch's membrane), which may have a significant effect on RPE graft survival. Evidence from human donor eye organ culture experiments indicates that healthy RPE cannot survive for an extended period of time on aged submacular Bruch's membrane, and the poorest survival is observed on AMD Bruch's membrane. These in vitro studies were performed on human submacular Bruch's membrane with no treatment to improve cell survival. Previous studies to improve cell survival on aged Bruch's membrane included adding ECM ligands singly or in combination to "coat" Bruch's membrane, detergent treatment to eliminate debris accumulated within Bruch's membrane followed by ECM ligand coating, and resurfacing Bruch's membrane with a cell-deposited matrix. The first two methods showed limited improvement in attachment and early survival. Long-term survival was not demonstrated. The last method improved long-term cell survival more than 200%. However, from a therapeutic standpoint, resurfacing submacular Bruch's membrane with the cell-deposited ECM was problematic due to the inability to solubilize ECM components in a manner compatible with clinical application. These studies demonstrate the need for development of a method to improve long-term cell transplant survival in AMD patients.

BCECs secrete an ECM that supports rapid attachment, growth, and differentiation of RPE. During BCEC-ECM formation, in addition to basal secretion, BCECs secrete ECM components into the overlying medium, including collagens, proteoglycans, and entactin/nidogen. Secretion of ECM components into the overlying medium is most abundant in early passage cells and exceeds basal ECM deposition in quantity. Since soluble ECM can affect cell shape and metabolism in addition to stimulating production of ECM molecules, the presence of these proteins suggests that conditioned medium harvested from BCEC cultures could be a source of cell-supporting soluble proteins and, if effective, could lead to development of an adjunct to cell-based therapy for AMD. In this example, assays were performed to characterize the behavior of RPE cells transplanted onto Bruch's membrane of aged and AMD donor eyes cultured in BCEC-CM or CM vehicle utilizing a previously characterized human submacular Bruch's membrane bioassay.

Material and Methods

Conditioned Medium Preparation

Cow eyes (ages 6 months-3 years) were obtained from local slaughterhouses. Each globe was rinsed briefly in 70% ethanol, and the cornea was separated from the rest of the globe by making a circumferential cut anterior to the limbus. The cornea was rinsed quickly in PBS and positioned with the epithelial surface down on a sterile support placed on a Petri dish. The cup formed by the cornea was filled with 0.05% trypsin-0.02% EDTA (Invitrogen-Gibco, Life Technologies, Carlsbad, Calif.) and placed in a 37° C., 10% CO2 incubator for 30-60 minutes. BCECs were scraped off gently using a blunt metal spatula and collected into a 15 ml tube containing Dulbecco's modified Eagle's medium (DMEM, Cellgro, Manassas, Va.) supplemented with 2 mM glutamine, 15% fetal bovine serum (FBS), 2.5 µg/ml amphotericin B, 50 µg/ml gentamicin, and 1 ng/ml bFGF (all from Invitrogen-Gibco) (termed "RPE medium"). Cells were spun down, resuspended in RPE medium, seeded onto 60 mm dishes, and cultured at 37° C. in 10% CO2. Cultures were passaged at confluence. For BCEC-CM harvest, passage-2 or -4 cells were cultured in RPE medium with 10% FBS and 5% donor bovine serum (Invitrogen-Gibco), instead of 15% FBS, until confluent. BCEC-CM was obtained by incubating confluent BCEC cultures for 72 hours in Madin-Darby Bovine Kidney Maintenance Medium (MDBK-MM, Sigma-Aldrich, St. Louis, Mo.) supplemented with 2.5 µg/ml amphotericin B and 50 µg/ml gentamicin. The vehicle, MDBK-MM (hereafter referred to as "CM vehicle"), is a serum- and protein-free, defined medium designed for maintaining high-density cultures of MDBK cells. Following collection, BCEC-CM was centrifuged briefly to remove cellular debris, and the supernatant was stored at −80° C. Twelve batches of BCEC-CM were used in this study.

Cell Culture

RPE were isolated from fetal eyes (Advanced Bioscience Resources, Inc., Alameda, Calif.; gestational age 18-22 weeks) or adult eyes (donor age 58, 71, 78 yrs.) after incubation of RPE/choroid pieces in 0.8 mg/ml (fetal eyes) or 0.4 mg/ml collagenase type IV (Sigma-Aldrich) (adult eyes) as described previously. RPE were cultured in RPE medium on bovine corneal endothelial cell-extracellular matrix (BCEC-ECM)-coated tissue culture dishes prepared in this laboratory according to a previously described protocol. After achieving confluence, primary fetal RPE cultures were passaged at a 1:6 split ratio onto BCEC-ECM-coated dishes using 0.25% trypsin-EDTA to harvest the cells. Subsequent cultures were passaged at a 1:4 split ratio. Adult RPE seeded onto Bruch's membrane were from day-11-15 primary cultures; fetal RPE were harvested from cultures of passage 1-3, 3-7 days in culture after seeding. Human embryonic stem cell-derived RPE (hES-RPE, Advanced Cell Technology, Worcester, Mass.), were established from a stem cell culture designated as MA09. Cells were maintained in MDBK-MM medium (Sigma-Aldrich) until removal from flasks and seeding onto Bruch's membrane explants. Cells of passage-32 as stem cells and passage-2 or -3 as hES-RPE were utilized and were removed from culture dishes using trypsin/EDTA after 50-85 days in culture.

Bruch's Membrane Organ Culture

Adult donor eyes were received from the Lions Eye Institute for Transplant and Research (Tampa, Fla.) and eyebanks placing donor eyes through their website (Ocular Research Biologics System (ORBS), orbsproject.org), Midwest Eyebanks (includes eyebanks in Illinois, Michigan, and New Jersey), the San Diego Eyebank (San Diego, Calif.), and eyebanks placing tissue through the National Disease Research Interchange (NDRI, Philadelphia, Pa.). Acceptance criteria for donor eyes included: 1) death to enucleation time no more than 7 hours; 2) death to receipt time no more than 48 hours; 3) no ventilator support prior to death; 4) no chemotherapy within the last 6 months prior to death; 5) no radiation to the head within the last 6 months prior to death; 6) no recent head trauma; 7) no ocular history affecting the posterior segment except for AMD. These acceptance criteria have been found in previous studies to yield well-preserved explants. Posterior segments were examined through a dissecting microscope for submacular pathology and documented by photography. A previously published method was used to create inner collagenous layer (ICL) surfaces by mechanical debridement. Six-millimeter diameter corneal trephines (Bausch and Lomb, Rochester, N.Y.) were used to create macula-centered, Bruch's membrane explants. Explants were placed in wells of 96-well plates for cell seeding and organ culture. Cells were seeded at a seeding density of 3164 cells/mm$^2$, a seeding density that has been shown to yield a monolayer of cells on a 6 mm diameter Bruch's membrane explant in organ culture one day after seeding. Explants were harvested at day-21, fixed in phosphate-buffered 2% paraformaldehyde and 2.5% glutaraldehyde, bisected, and processed for light or scanning electron microscopy.

Scanning Electron Microscopy (SEM)

Explant halves for SEM were post-fixed in phosphate buffered osmium tetroxide, dehydrated using a graded series of ethanol, critical point dried (Tousimis, Rockville, Md.), and sputter-coated (Denton, Moorestown, N.J.) according to standard SEM protocols. SEM image acquisition (JEOL JSM 6510, Tokyo, Japan) was performed with routine photography at 30×, 50×, 200×, and 1000×. SEM evaluation of Bruch's membrane involved assessment of cell surface morphology and, in areas not resurfaced by cells, the level of Bruch's membrane exposed by debridement.

Light Microscopy (LM)

Bruch's membrane explant halves processed for histology were embedded in LR White (Electron Microscopy Sciences, Hatfield, Pa.); 4-6 sections of 2 μm thickness were mounted on slides, dried overnight, and stained with 0.03% toluidine blue (Electron Microscopy Supply). LM evaluation focused on RPE morphology (cell shape, density, pigmentation, polarization) and evaluation of Bruch's membrane and choroid. Nuclear density counts were performed to assess treatment success quantitatively, comparing paired explants from fellow eyes. Nuclear density counts were performed by counting the number of RPE nuclei in intact cells in contact with Bruch's membrane in the central 3 mm of 4-5 non-consecutive slides (approximately every 5th slide). Linear measurements of Bruch's membrane in the analyzed area were obtained by digital image acquisition and measurement with the freehand line tool using NIH Image J (http://rsb.info.nih.gov/ij/index.html). Nuclear density was expressed as the number of nuclei per mm of Bruch's membrane.

Statistical Analysis

Statistical differences between pairs were determined by Wilcoxon Signed Rank tests. For comparisons between time points and comparison between groups, existence of significant differences was determined by Kruskal-Wallis One Way Analysis of Variance on Ranks. If significance was observed, All Pairwise Multiple Comparison Procedures testing (Dunn's method) determined the significance between pairs of groups. Comparisons between two groups in unpaired studies were by Mann-Whitney Rank Sum tests. Comparisons between ages of two groups were by unpaired t-tests or between multiple groups by One Way ANOVA. Ages are indicated as mean age with standard deviation. A P value <0.05 was considered statistically significant.

Extracellular Matrix Deposition

Fetal RPE (3164 cells/mm$^2$) were seeded onto tissue culture-treated plastic (48-well plates) or Bruch's membrane and cultured in BCEC-CM or RPE medium. ECM on tissue culture plates was analyzed at day-7, -14, and -21 (N=3). ECM on Bruch's membrane (6 donor pairs; three pairs with extensive drusen; 3 pairs normal; mean donor age, 79.2±3.17 yrs.) was analyzed at day-21 only. Primary antibodies were: mouse monoclonal collagen IV (1:500 dilution, Sigma-Aldrich), rabbit polyclonal laminin (1:25 dilution, Sigma-Aldrich), and mouse monoclonal fibronectin (1:50 dilution, Abcam, Cambridge, Mass.). Secondary antibodies were fluorescein (FITC)-conjugated goat anti-mouse IgG (H+L) and rhodamine (TRITC)-conjugated goat anti-rabbit IgG (H+L) applied at 1:50 dilution (both from Jackson ImmunoResearch Laboratories, West Grove, Pa.). All antibodies were diluted in 2% normal goat serum, 0.3% Triton X-100 (both from Sigma-Aldrich) in phosphate buffered saline (PBS).

Cell Culture:

Cells were removed from culture wells by incubating in 0.02M NH4OH for 5 minutes followed by rinsing in PBS. The exposed ECM was fixed for 15 minutes in cold 4% paraformaldehyde followed by 3 PBS washes. Wells were then incubated for 45 minutes at room temperature in blocking solution (2% normal goat serum, 0.5% BSA in PBS). Primary antibodies were applied to culture wells and incubated for 2 hours at room temperature. After washing with PBS plus 0.3% triton, secondary antibodies were applied, and wells were incubated for 1 hour at room temperature. After washing with PBS plus triton, mounting medium (Vectashield, Vector Laboratories, Burlingame, Calif.) was added to the wells. Epifluorescence images for each protein at the same time point were photographed at the same exposure to determine relative differences in the amount of deposited protein using an inverted microscope equipped with the appropriate fluorescein and rhodamine filters (10× neoflaur objectives, Axiovert, Carl Zeiss, Thornwood, N.Y.). Following immunostaining photography, ECM was stained with 0.1% Ponceau S (Sigma-Aldrich) for 10 minutes at room temperature and photographed using a 32× phase objective.

Bruch's Membrane:

At day-21, live RPE were imaged by calcein staining (Live/Dead viability/toxicity assay, Molecular Probes, Eugene, Oreg.) to determine surface coverage by cells. Following a brief rinse in PBS, explants were incubated in 2 µM calcein for 1 hour at room temperature. Explants were rinsed briefly, then photographed at 2.5× magnifications using a fluorescence microscope equipped with a fluorescein filter set (Axiophot, Carl Zeiss). Montages of calcein-imaged explants were created in Photoshop CS4 (Adobe Systems, Mountain View, Calif.). After calcein imaging and RPE removal by 5 minute incubation in 0.02M NH4OH, explants were fixed in 4% paraformaldehyde for 1 hour at 4° C. Following washing in PBS, explants were blocked at room temperature for 45 minutes. The explants were then bisected prior to immunostaining, and the surface of Bruch's membrane was immunostained for laminin and collagen IV (one half) and fibronectin and laminin (other half) or cut into thirds with the third piece used for controls. Primary antibodies were applied to explants, which were then incubated overnight at 4° C. The following day, explants were rinsed with PBS, and secondary antibodies were applied. Explants were incubated for 2 hours at room temperature following by washing with PBS. Explants were stored and examined in mounting medium. Single images or z-stacks were acquired from the surface of Bruch's membrane using a 40× water immersion lens on a confocal microscope (LSM510, Carl Zeiss, Thornwood, N.Y.). Lasers lines and corresponding emission filters were: 488 nm excitation, 505-530 nm band pass filter for FITC; 543 nm excitation, 560-615 nm band pass filter for rhodamine. Following confocal microscopy evaluation, explants were processed for SEM.

Results

Effect of BCEC-CM on Long-Term Cell Survival on Aged and AMD Bruch's Membrane

Figure 24:
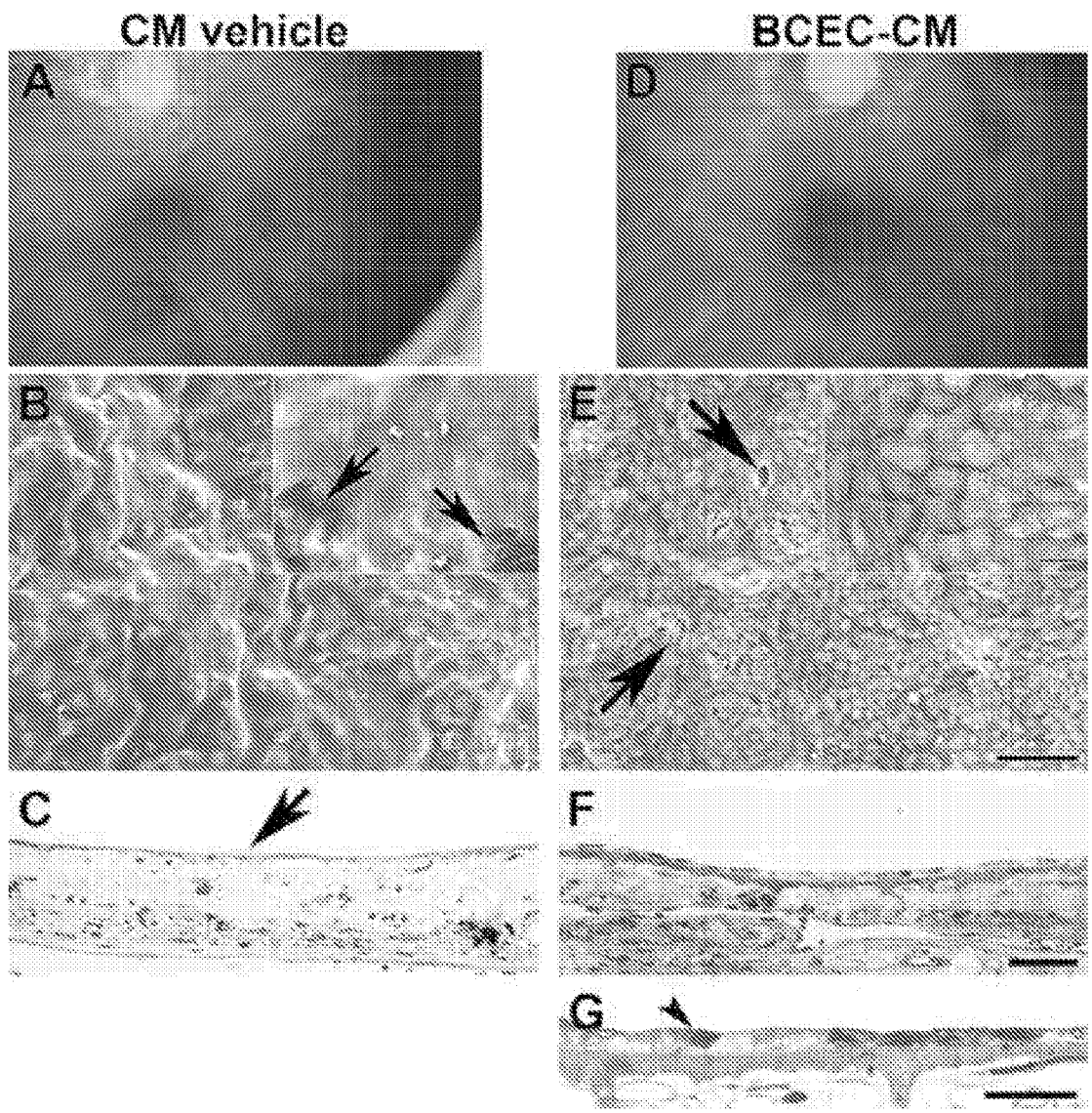
FIGS. 24A-G show paired explants from an 81-year-old male with no submacular pathology, seeded with fetal RPE. (A, D) No submacular pathology is seen in the post mortem clinical photographs. CM vehicle: (B) Cellular debris but no intact cells are seen on the surface of Bruch's membrane. Few remaining patches of RPE basement membrane (arrows, insert) are present. (C) Rare single cells are seen on the explant surface. Arrow points to a single, very flat cell. BCEC-CM: (E) The explant is almost fully resurfaced with small defects in cell coverage (arrows). Patches of small, rounded cells are interspersed with localized areas where cells are more variable in size and shape. Cells express abundant short apical surface processes on their surfaces (inset). (F, G) The explant is resurfaced by a mono- and bilayer of cells. Arrowhead (G) points to a cell overlying a cell on Bruch's membrane. CM vehicle ND, 0.51±0.16; BCEC-CM ND, 26.8±0.41. Scale bar: (E) 100 µm; (E, inset) 20 µm; (F) 50 µm; (G) 20 µm. Toluidine blue staining.
Figure 25:
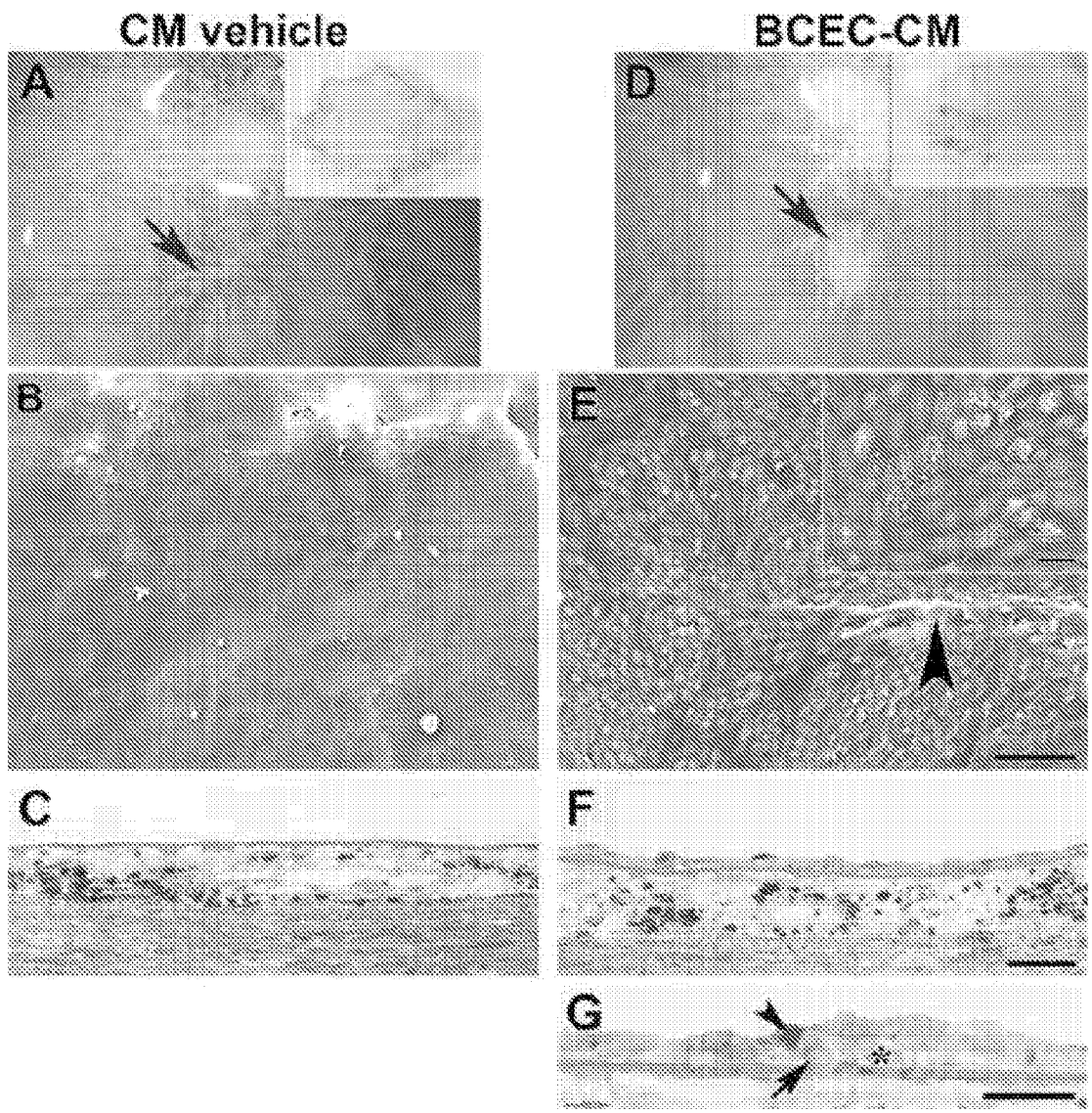
FIGS. 25A-G show paired explants from a 75-year-old female with large bilateral subfoveal choroidal new vessels (CNVs), seeded with fetal RPE after mechanical CNV removal. (A, D) Arrows point to CNVs in postmortem clinical photographs; insets show CNVs after surgical dissection from Bruch's membrane. CM vehicle: (A) The CNV was approximately 4.8×3 mm. (B, C) No intact cells are seen on the explant surface. BCEC-CM: (D) The CNV was approximately 4×3.5 mm. (E) Fetal RPE fully resurface the explant with some areas of thick multilayers (arrowhead). The cell surfaces are covered with apical processes (inset). (F) Cells resurfacing the explant are predominantly monolayered with localized areas where thin or spindle-shaped cells overlay cells on Bruch's membrane. The cells resurfacing the explant are more variable in size and shape than those observed on explants from donors with geographic atrophy. (G) Fetal RPE are able to resurface small drusen (arrow points to druse on Bruch's membrane) and basal laminar deposits (asterisk). Arrowhead points to a cell with a darkly staining irregular-shaped nucleus. CM vehicle ND, 0; BCEC-CM ND, 25.10±0.30. Scale bar: (E) 100 µm; (E, inset) 20 µm; (F) 50 µm; (G) 20 µm. Toluidine blue staining.
Figure 26:
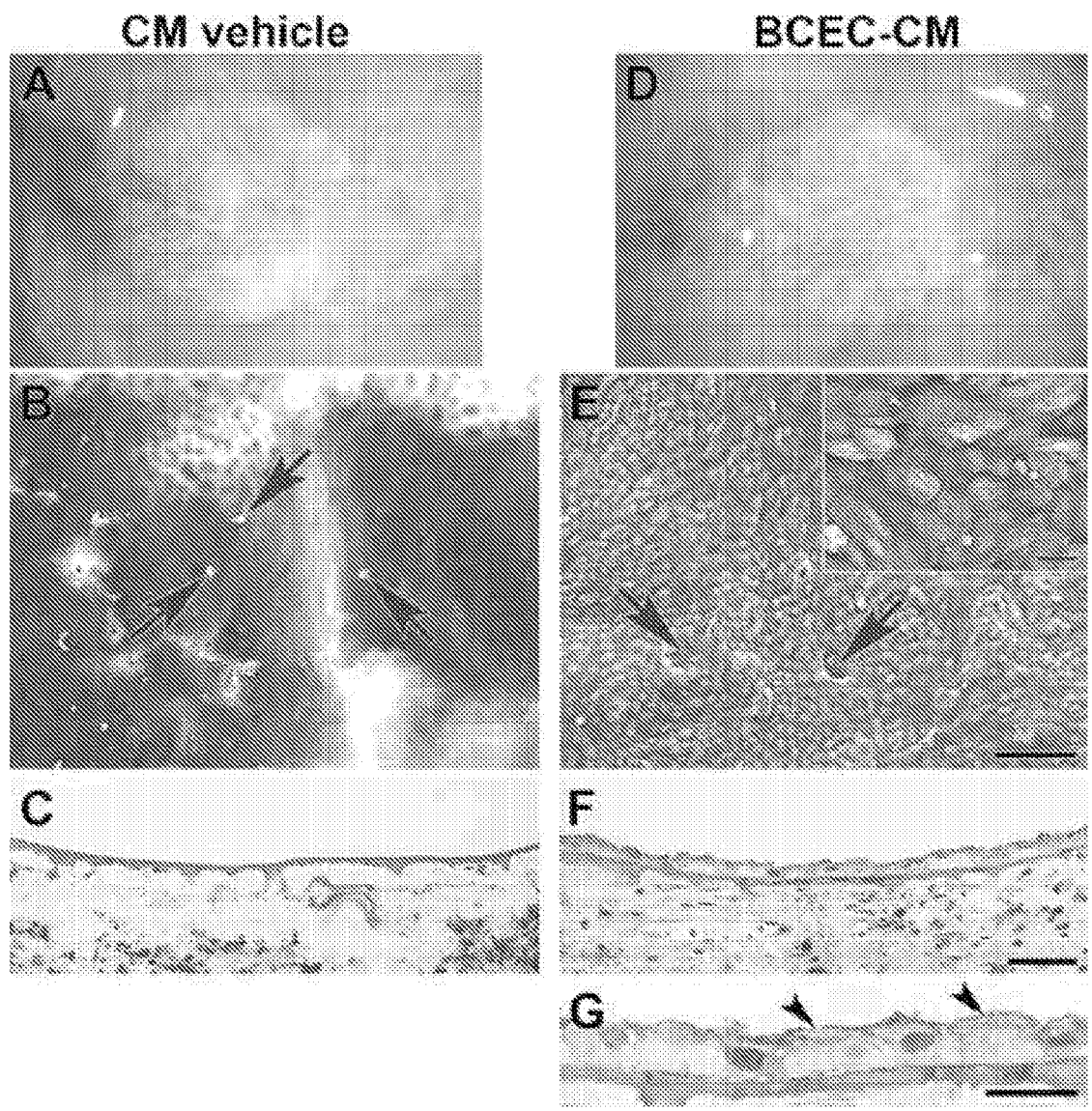
FIGS. 26A-G show paired explants from an 82-year-old female with geographic atrophy, seeded with fetal RPE. The patient's clinical history noted AMD for 20 years. (A, D)
Figure 27:
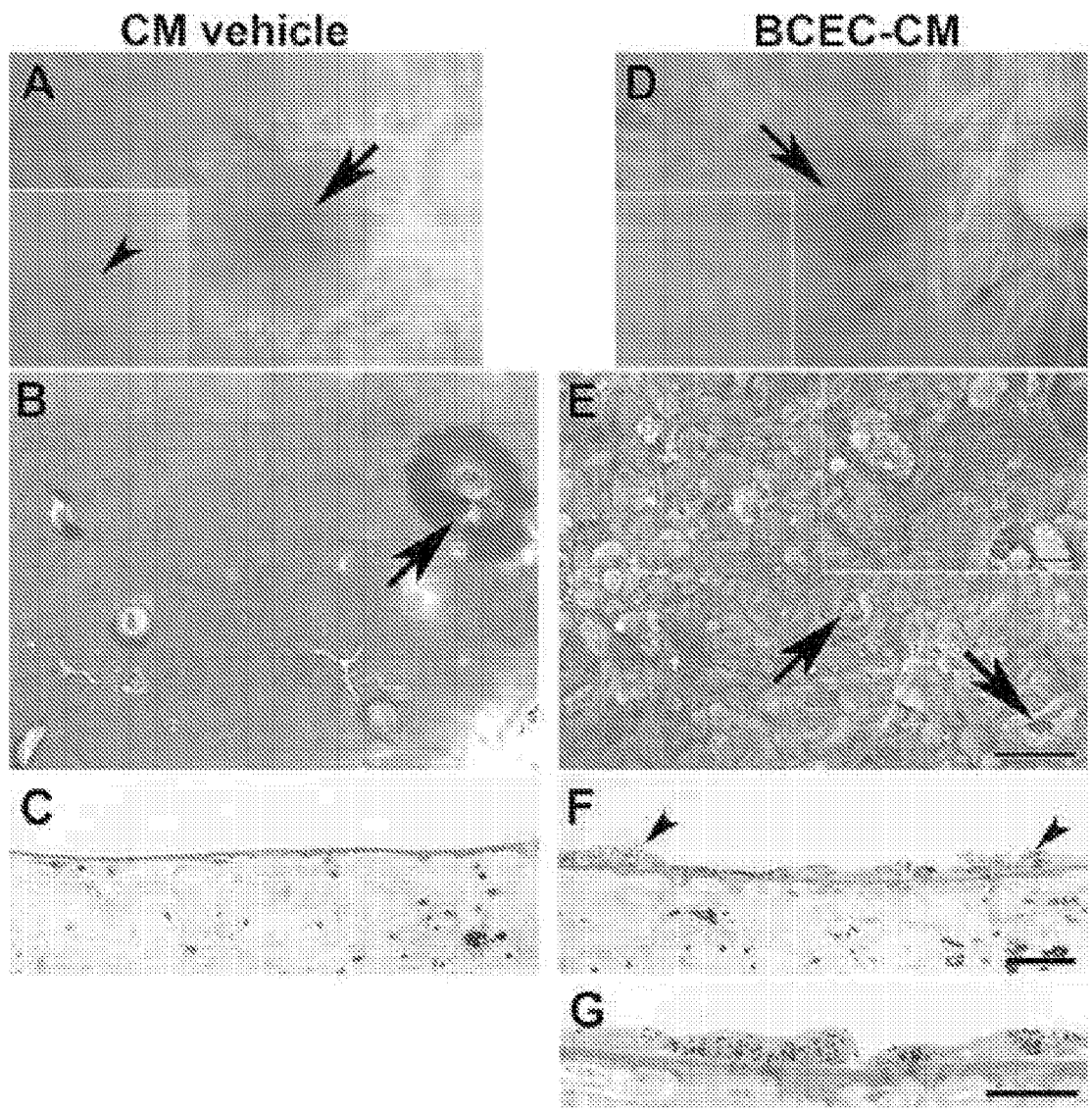

RPE derived from human embryonic stem cells (hES-RPE), fetal RPE, and aged adult RPE were seeded onto the inner collagenous layer of submacular Bruch's membrane of donor eyes age 62 and older (see Table 9 below for donor information) and cultured in BCEC-CM or CM vehicle (representative images, FIGS. 23-27). On explants cultured in CM vehicle, limited resurfacing was seen at day-21 with no or few surviving cells on the majority of explants (hES-RPE, 3 of 6 total explants resurfaced with few cells, and no cells on the remaining 3 explants; fetal RPE, 20 explants with no or few cells of 22 total explants; adult RPE, 5 explants with no or few single cells of 7 total explants) (FIGS. 23-27, A-C). When present, intact cells were large and flat, regardless of cell type (FIGS. 24C, 27B). Cytoplasmic vacuoles were common. All explants cultured in BCEC-CM showed cells remaining at day-21 with many explants almost fully (i.e., more than 75% of the surface covered by cells) or fully resurfaced (hES-RPE, 3 explants completely or almost fully resurfaced of 6 total explants; fetal RPE, 16 explants completely or almost fully resurfaced of 22 total explants; adult RPE, 6 explants almost fully resurfaced of 7 total explants). hES-RPE (FIGS. 23 E-G) cells were predominantly monolayered with highly variable morphology and were larger and flatter than fetal RPE (FIGS. 24-26, E-G). Fetal RPE showed focal areas of bi- and multilayers with the most extensive multilayering found in explants that underwent CNV removal prior to cell seeding (FIG. 25E). Resurfacing was extensive and many cells were compact with abundant expression of well-developed surface apical processes regardless of submacular pathology (FIGS. 22-26E, insets). Adult RPE, generally larger than fetal RPE, were predominantly monolayered with localized multilayered clumps of cells (FIGS. 27E-G). Adult RPE exhibited abundant short apical processes (FIG. 27E). Since adult RPE were from primary cultures, the cells were generally more pigmented than hES-RPE or fetal RPE (FIG. 27G).

The nuclear density of hES-RPE cells grown in BCEC-CM (mean, 20.1 nuclei per mm Bruch's membrane) was significantly higher than that of cells grown in CM vehicle (mean, 5.1 nuclei per mm Bruch's membrane) (P=0.031). Fetal RPE nuclear density after culture in BCEC-CM (mean, 20.6 nuclei per mm Bruch's membrane) was significantly higher than cells cultured in CM vehicle (mean, 2.2 nuclei per mm Bruch's membrane) (P<0.001). Adult RPE cultured in BCEC-CM nuclear density (mean, 10.0 nuclei per mm Bruch's membrane) was also significantly higher than the nuclear density of cells cultured in CM vehicle (mean, 1.2 nuclei per mm Bruch's membrane) (P=0.016). (See FIG. 28A.) ANOVA on ranks showed significant differences in the median values among the cell types cultured in BCEC-CM (P=0.004). Nuclear densities of fetal RPE and hES-RPE cultured in BCEC-CM were significantly higher than the nuclear density of adult RPE cultured in BCEC-CM (P<0.05). Fetal RPE and hES-RPE nuclear densities were not significantly different when cultured in BCEC-CM (P>0.05). Nuclear densities of hES-RPE, fetal RPE, and cultured adult RPE were not significantly different when cultured in CM vehicle only (P=0.060). There were no statistically significant differences in ages of donor eye explants between groups (P=0.345: hES-RPE mean donor age, 80.2±8.4 yrs.; fetal RPE mean donor age, 80.2±7.8 yrs.; aged adult RPE mean donor age, 75.7±3.64 yrs.). It was assessed whether RPE survival on age-matched AMD vs. non-AMD Bruch's membrane was similar in the presence of BCEC-CM (FIG. 28B). Explants seeded with fetal RPE on aged Bruch's membrane from eyes without significant AMD changes (including donor eyes with submacular focal RPE hyperplasia and few small (<100 µm) drusen were compared to explants seeded on AMD Bruch's membrane. AMD donors included donor eyes with CNVs (removed prior to cell seeding with no subsequent debridement), geographic atrophy, and/or extensive large (>125 µm) drusen. After culture in BCEC-CM, non-AMD donor eye mean nuclear density was 19.6 nuclei/mm Bruch's membrane, and AMD donor eye mean nuclear density was 21.3. After culture in CM vehicle, non-AMD donor eye mean nuclear density was 2.4 nuclei/mm Bruch's membrane, and AMD donor eye mean nuclear density was 2.0. The differences in fetal RPE nuclear density on Bruch's membrane in the presence of BCEC-CM vs. CM vehicle were statistically significant for both non-AMD and AMD donors (non-AMD, P=0.004; AMD, P<0.001). For a given culture medium, the nuclear densities of fetal RPE on non-AMD vs. AMD explants were not significantly different (culture in BCEC-CM, P=0.548; culture in CM vehicle, P=0.231). Ages of the two groups were not statistically different (P=0.226: aged, non-AMD mean donor age, 77.8±5.0 yrs.; AMD mean donor age, 82.2±9.3 yrs.).

RPE Cell Survival Following Different BCEC-CM Culture Times

To determine whether RPE behavior on submacular Bruch's membrane explants depends on the time of exposure to BCEC-CM, explants seeded with fetal RPE and cultured for differing periods of time in BCEC-CM were compared to fellow eye explants cultured for the entire incubation period (21 days) in BCEC-CM. One explant of the pair was cultured in BCEC-CM for 3-, 7-, or 14-days followed by culturing in CM vehicle to bring the total number of days in culture to 21 (FIG. 29). Fellow eye explants were cultured in BCEC-CM for the entire 21-day period. Fetal RPE nuclear densities on explants cultured for 3 days in BCEC-CM (mean nuclear density, 3.5 nuclei/mm Bruch's membrane) vs. 21 days in BCEC-CM (mean nuclear density, 21.8) were significantly different (P=0.016). Nuclear densities on explants after 7-day BCEC-CM culture (mean nuclear density, 10.9 nuclei/mm Bruch's membrane) vs. 21 days (mean nuclear density, 28.0) were significantly different (P=0.008). Nuclear densities after 14-day BCEC-CM culture (mean nuclear density, 17.0 nuclei/mm Bruch's membrane) vs. 21-day BCEC-CM culture (mean nuclear density, 27.9) were significantly different (P=0.031). Nuclear densities of explants cultured for 14 days in BCEC-CM were significantly higher than those of explants cultured for 3 days in BCEC-CM (P<0.05) while 3- vs. 7-day and 7- vs. 14-day nuclear densities were not significantly different (P>0.05). There were no statistically significant differences between the control groups cultured for the entire 21-day period in BCEC-CM (P=0.074). Ages between groups were not significantly different (P=0.881: 3-day cohort, mean donor age, 78.3±7.6 yrs.; 7-day cohort, mean donor age, 76.5±6.0 yrs.; 14-day cohort, mean donor age, 77.2±7.1 yrs.)

Comparison of RPE Nuclear Density after 21-Day Culture in Different Media and on Different Surfaces Nuclear densities of fetal RPE after 21-day culture in BCEC-CM or CM vehicle on AMD (including late AMD) and aged, non-AMD explants (current study: CM vehicle, mean donor age, 80.2±7.8 yrs. (data represented in FIG. 28A); BCEC-CM mean donor age, 78.8±7.3 yrs. (combined data represented in FIG. 28A and 21-day controls of FIG. 29)), were compared with: 1) 21-day fetal RPE nuclear densities on young explants (mean donor age, 44.8±2.3 yrs.) cultured in RPE medium, 2) aged and early AMD Bruch's membrane explants (mean donor age, 73.6±6.4 yrs.) cultured in RPE medium, and 3) BCEC-ECM-resurfaced aged Bruch's membrane (mean donor age, 73.9±7.4 yrs.) cultured in RPE medium (FIG. 30). Of the aged explants studied, mean donor age of explants cultured in BCEC-CM and CM vehicle (includes eyes with early as well as late AMD) were significantly higher than the mean donor age of aged, including early AMD, explants cultured in RPE media (P<0.05) but not significantly different from the mean donor age of explants that were resurfaced with BCEC-ECM (aged, non-AMD) (P>0.05). The nuclear densities of fetal RPE on BCEC-ECM-resurfaced aged Bruch's membrane (mean nuclear density, 23.2 nuclei/mm Bruch's membrane) and unresurfaced young Bruch's membrane (mean nuclear density, 27.2) were significantly higher than the nuclear density on aged, untreated Bruch's membrane after culture in RPE medium (mean nuclear density, 11.221) (P<0.05) and were not significantly different from the nuclear density on explants cultured in BCEC-CM (mean nuclear density, 23.2) (P>0.05). Nuclear densities of fetal RPE cells in these three conditions (i.e., BCEC-CM-cultured, BCEC-ECM-resurfaced, and young Bruch's membrane) were significantly higher than the nuclear density on aged and early AMD Bruch's membrane cultured in RPE medium (mean nuclear density, 2.2) (P<0.05). Nuclear densities of cells cultured in RPE medium on aged and early AMD Bruch's membrane were significantly higher than nuclear densities of cells cultured in CM vehicle on aged and AMD Bruch's membrane (P<0.05).

ECM Deposition Following Culture in BCEC-CM

Providing a newly-deposited ECM on the surface of Bruch's membrane can significantly improve cell survival in long-term organ culture, and the resulting nuclear densities are similar to those observed after culture in BCEC-CM (FIG. 30). To determine whether incubation in BCEC-CM stimulates ECM deposition, which might account for the cell-preserving effect of BCEC-CM, it was investigated whether RPE ECM deposition on Bruch's membrane was increased after culture in BCEC-CM. Since little RPE cell survival on Bruch's membrane was seen in CM vehicle, assays were performed to compare ECM deposition after culture in BCEC-CM with ECM deposition after culture in standard RPE culture medium where some degree of RPE resurfacing was more likely (see FIG. 30). To assess ECM deposition on a non-toxic substrate, ECM deposition onto tissue culture dishes was examined at days-7, -14, and -21 (N=3).

Figure 31:
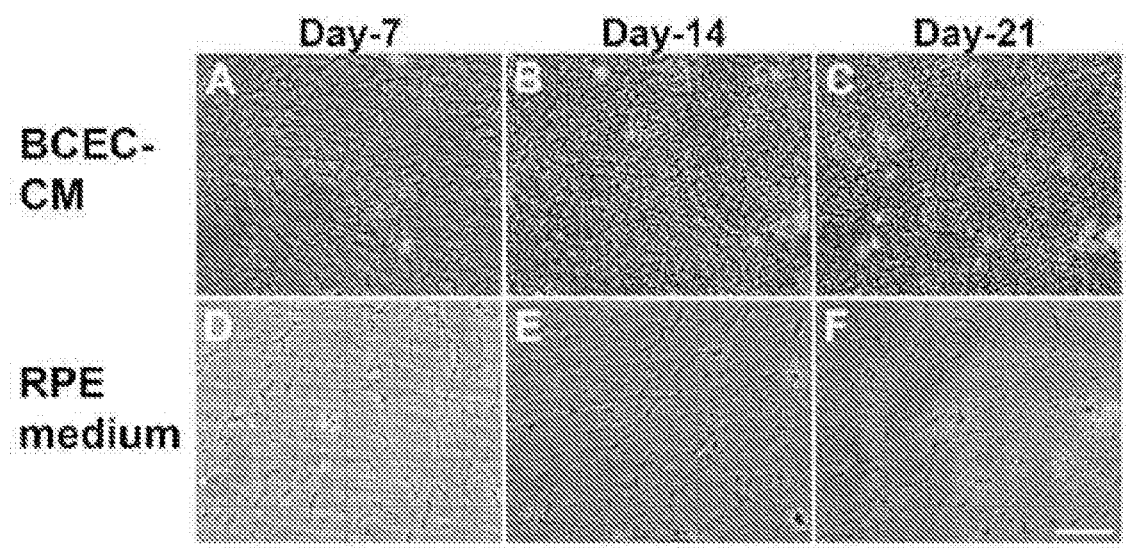

Stained fibers were present on the surface of culture dishes in both media at all three time points. As the time in culture increased, the amount of ECM deposition increased. ECM visualized by Ponceau S staining showed deposition after BCEC-CM culture to be more extensive than deposition after RPE medium culture at all time points (FIG. 31). In BCEC-CM cultures, collagen IV and laminin were present as a thick coating with defects that became smaller with time in culture (FIGS. 32-34). Collagen IV deposition appeared to be more extensive than laminin and fibronectin deposition at day-7. At day-14 and -21, collagen IV and laminin showed more uniform coating of the culture dish surface compared to day-7. Collagen IV and laminin appeared to be extensively co-localized at all three time points (FIGS. 32-34, C). Fibronectin labeling was on a network of thin fibers at week-1 with diffuse labeling of the culture dish between fibers seen at day-14 and -21. Some colocalization of fibronectin with laminin was seen (FIGS. 32-34, F), but it was not as extensively co-localized as laminin was with collagen IV. In RPE medium cultures (FIGS. 32-34, G-L), collagen IV and laminin labeling at day-7 was not as extensive as that seen in BCEC-CM cultures with labeling seen as an open mesh with localized areas coating the culture dish between the fibers of the mesh. Localized areas of surfaces coated with collagen IV and laminin were more extensive at day-14 and -21 compared to day-7, but there was little, if any, increase in labeling between day-14 and -21. Faint fibronectin labeling was detected in RPE medium cultures at all time points with sparse to moderate labeling seen at day-21. Similar to that observed in BCECCM cultures, collagen IV and laminin showed extensive co-localization. Fibronectin co-localization was difficult to determine due to sparse labeling in some cultures, but it did seem to partially co-localize with laminin (see FIG. 32L). Controls showed diffuse, faint fluorescence with rhodamine filters with secondary antibody only in the 3-week RPE medium cultures. No detectable fluorescence was found with FITC or rhodamine filters in preparations at other time points or in CM vehicle cultures at all time points (not shown). Controls in which the antibody was omitted showed no fluorescence with either filter set (not shown). Calcein imaging confirmed the presence of RPE on Bruch's membrane explants cultured in both media for 21 days with more extensive resurfacing and smaller, more compact cells on explants cultured in BCEC-CM (FIGS. 35A and L). On explants cultured in BCEC-CM, SEM and confocal evaluation showed extensive ECM on the surface of the inner collagenous layer for all three markers (N=6; mean donor age, 79.2±3.17 yrs) (FIGS. 35A-F and H-J). The extent and complexity of the ECM varied within and between BCEC-CM-treated explants, ranging from a complex mesh of thick and thin fibers to a fairly continuous ECM sheet with a rough surface (FIGS. 35A-F and H-J). Collagen IV and laminin labeling were found as thick and thin fibers with some localized thickening giving the labeling a punctate appearance. Both collagen IV and laminin formed a continuous sheet in localized areas, visualized between fibers. Collagen IV labeling was more variable than that of fibronectin and laminin, sometimes not as extensive. There was some co-localization of collagen IV with laminin. Fibronectin was found mainly in fibers and did not appear to co-localize with laminin. On explants cultured in RPE medium, no or sparse localized labeling was observed despite RPE presence on Bruch's membrane as visualized by Calcein imaging (FIGS. 35 L and M). When present, laminin labeling could be seen on short strands. If present, fibronectin was present in short (thin) strands; sometimes labeling was punctate. Collagen IV labeling generally was sparse or not present. ECM tended to be more prevalent outside the submacular area on the periphery of the explant. SEM evaluation of the explants showed predominantly bare ICL or a few strands on the surface of the bare ICL in explants cultured in RPE medium (FIG. 35M). Control explant pieces (omission of primary antibody or both primary and secondary antibodies) showed slight autofluorescence of the tissue (FIGS. 35G and K) at the microscope settings used to obtain immunolabeling images.

In previous studies examining fetal RPE attachment to aged and AMD submacular Bruch's membrane, it was showed that RPE can attach to a high degree to the RPE basement membrane and to the inner collagenous layer, indicating that attachment to these layers may not be the limiting factor in cell transplant success. Immunochemistry studies showed that at days-3 and -7 after seeding, fetal RPE are present on Bruch's membrane and appear to be fairly healthy based on the appearance of stained nuclei. Between days-7 and -14, a high degree of cell death has occurred, and additional cell death was observed at days-14 and -21. At these later time points, abundant condensed and fragmented nuclei are present. These studies provide evidence that a method to ensure cell survival (vs. attachment alone) must be developed for RPE cell replacement therapy to be successful in AMD patients.

Previously, it was demonstrated that cell survival on aged submacular Bruch's membrane can be enhanced greatly by resurfacing Bruch's membrane with a cell-deposited ECM. This resurfacing strategy was chosen because ECM deposited by BCECs supports rapid fetal RPE attachment and growth in cell culture. It was showed that resurfacing aged Bruch's membrane with BCEC-ECM improved long-term cell survival significantly (>200%). A limitation to the feasibility of utilizing this ECM in clinical applications was the insolubility of the ECM and the resulting low yield of proteins with ECM harvest, both for transfer to Bruch's membrane and for quantitative analysis. In the present study, BCEC-CM was harvested from BCECs cultured under conditions similar to those that yield BCEC-ECM-coated culture dishes and BCEC-ECM deposition on Bruch's membrane. The rationale for this choice was based on the reported abundance of potentially cell-supporting proteins secreted into the medium, such as ECM and ECM-associated molecules. In the present study, it was demonstrated that cell survival is greatly enhanced when RPE cells are exposed to this BCEC-CM in long-term culture and, importantly, that cell survival is enhanced on submacular Bruch's membrane of AMD eyes. It was showed previously that RPE survival on AMD submacular Bruch's membrane explants was severely impaired after culture in RPE medium. However, the nuclear density of fetal RPE on submacular human Bruch's membrane cultured in RPE medium is significantly higher compared to the nuclear density of fetal RPE cultured in CM vehicle (FIG. 30). This difference could be related to the significantly lower mean donor age of the explants cultured in RPE media and, therefore, possibly fewer aged and AMD changes to Bruch's membrane. However, culture on non-AMD and AMD explants was similarly poor in CM vehicle. It seems likely that the serum in the RPE medium aided in supporting cell survival to a slight degree but not to the degree seen in BCEC-CM.

BCEC-CM may supply soluble matrix proteins for ECM deposition, stimulate ECM deposition, and/or stimulate the RPE in some other fashion, thus allowing better survival that could lead to increased ECM deposition on aged and AMD submacular Bruch's membrane. The presence of increased ECM deposition under the cells cultured in BCEC-CM compared to cells cultured in RPE medium may reveal a mechanism by which cell survival is enhanced, perhaps in the same manner that BCEC-ECM resurfaced explants support long-term cell survival on submacular human Bruch's membrane. It is not known if the ECM deposition per se enabled cell survival in the same way as resurfacing Bruch's membrane with BCEC-ECM or if the ECM deposition was a reflection of long-term survival of the cells by another mechanism. When RPE cell survival is observed on explants cultured in RPE medium, the cells are not as differentiated as those cultured in BCECCM and have not deposited ECM to any degree. The degree of ECM deposition by RPE on culture dishes in RPE medium or in BCEC-CM is much greater than that observed on Bruch's membrane explants. This difference may arise because RPE appear to mature more slowly on Bruch's membrane, and a certain degree of maturity must be obtained before ECM deposition can occur. Differences in the amount and composition of ECM deposition may also be related to differences in cellular response to the underlying substrate. Since the antibodies used in this study were not human-specific, it was not known if deposited proteins originated from the BCEC-CM (bovine proteins) or from protein synthesis by the RPE or both. As mentioned previously, when cultured in standard RPE medium, fetal RPE can survive to a high degree up to 7 days in organ culture on submacular human Bruch's membrane. After day-7, survival is impaired with decreasing presence of cells as time in culture increases further. The necessity of long-term presence of BCEC-CM to assure cell survival is consistent with the notion that sustained cell stimulation is a factor in assuring cell survival. The RPE survival after culture in BCEC-CM as measured by nuclear density was statistically similar to that of cells cultured on BCEC-ECM and also similar to that observed on young Bruch's membrane, the latter both cultured in RPE medium (FIG. 30). The nuclear densities observed in these studies are much lower than the nuclear densities of submacular in situ RPE even when comparing age matched nuclear densities and also much lower than the nuclear densities of fetal RPE in culture. The lower nuclear density on submacular Bruch's membrane after culture in BCEC-CM is partly due to the existence of defects in surface coverage on some explants. Many explants are almost fully resurfaced or are fully resurfaced after culture in BCEC-CM, and many cells appear to show some morphological features of differentiation (e.g., apical processes, tight junctions). However, there is variability in cell size with some cells fairly large, especially compared to the size of cultured fetal RPE. One source of the variability in cell behavior between explants might be biological variability in the composition of BCEC-CM between batches, as some batches appeared to be less effective than others, showing more and larger defects in surface coverage and larger and flatter cells. Another source of variability in cell behavior arises from differences in cell survival on localized areas of Bruch's membrane within explants, as some explants showing excellent overall resurfacing also exhibited small localized defects in RPE coverage (e.g., FIGS. 24 and 26). Lastly, particularly in reference to the AMD cohort, variability in cell behavior on explants with CNVs is likely related, at least in part, to the differences in the Bruch's membrane surface following CNV removal since no additional debridement was performed. The degree of damage to Bruch's membrane or preservation/removal of deposits on Bruch's membrane following CNV removal were highly variable within and between donor eyes. In a previous study, hES-RPE were shown to have the potential to survive on equatorial and submacular Bruch's membrane to a similar degree as fetal RPE after day-21 culture in RPE medium. On submacular Bruch's membrane, the survival was poor for both cell types with hES-RPE survival impaired at earlier times in culture than fetal RPE. In these previous studies, hES-RPE was from frozen stock, which is a possible cause for the difference in initial cell survival since the fetal RPE were from fresh cultures. However, in the current study, hES-RPE were from fresh stock, and although the nuclear densities of hES-RPE cultured in BCEC-CM were similar to those of fetal RPE, hES-RPE in general were very flat and not differentiated to the same degree as fetal RPE on submacular Bruch's membrane. These results imply that hES-RPE may take longer to acquire mature RPE features on Bruch's membrane compared to fetal RPE, consistent with behavior observed in cell culture. Whether fetal RPE or hES-RPE can achieve size and differentiation features found in cell culture or in situ and whether the cells can perform RPE functions are future studies that must be considered.

Cultured aged adult RPE were generally larger than hES-RPE and fetal RPE in cell culture and on Bruch's membrane. On Bruch's membrane, most adult RPE showed well developed apical processes even in very large flat cells, but their survival in general was not as good as that of fetal RPE or hES-RPE. The nuclear density of cultured adult RPE after BCEC-CM culture ($10.0 \pm 0.95$) was not significantly different ($P=0.887$) from the nuclear density of fetal RPE after RPE medium culture ($11.2 \pm 1.7$, FIG. 30). These results indicate that while culture in BCEC-CM significantly enhances RPE cell survival on aged Bruch's membrane, aged adult RPE may not be the best choice for cell transplantation especially when compared to the resurfacing achieved by fetal RPE and hES-RPE.

There is no other technique known that promotes such robust RPE survival on submacular AMD Bruch's membrane (including eyes with geographic atrophy and CNVs). 19, 20 Identification of the critical components of this BCEC-CM and RPE function testing are the next steps in the development of a surgically usable adjunct to improve RPE survival and differentiation on submacular human AMD Bruch's membrane.

TABLE 9

Donor information
SI Table 1. Donor information

| | | | Submacular Pathology | |
|---|---|---|---|---|
| Donor Age | Ethnicity/sex | CM cultured | | CM Vehicle cultured |
| A. hES-RPE on AMD and non-AMD Bruch's membrane (mean age 80.17 ± 3.41 yrs.) | | | | |
| 68 | CF | Few mixed size drusen | | Normal |
| 74 | CF | Confluent soft drusen | | Soft drusen |
| 80 | CM | Normal | | Normal |
| 83 | CM | RPE hyperpigmentation, mixed size drusen | | RPE hyperpigmentation, mixed size drusen |
| 84 | CF | Normal | | Normal |
| 92 | CF | Confluent soft drusen | | Confluent soft drusen |
| B. Fetal RPE on non-AMD Bruch's membrane (mean age 77.8 ± 1.69 yrs.) | | | | |
| 67 | CM | Few mixed size drusen | | Few Hard drusen |
| 75 | CM | Focal RPE hyperpigmentation | | Normal |
| 76 | CM | Normal | | Normal |
| 77 | CM | Normal | | Normal |
| 78 | CM | Normal | | Normal |
| 79 | CM | Few hard drusen | | Few hard drusen |
| 81 | CM | Few hard drusen | | Normal |
| 83 | CM | Few hard drusen | | Few hard drusen |
| 84 | CF | Few mixed size drusen | | Few mixed size drusen |
| C. Fetal RPE on AMD Bruch's membrane (mean age 81.9 ± 2.49 yrs) | | | | |
| 62 | CM | Soft drusen | | Soft drusen |
| 75 | CF | Large CNV | | Large CNV |
| 76 | CF | Confluent soft drusen | | Confluent soft drusen |
| 79 | CF | CNV, focal RPE hyperpigmentation, soft drusen | | focal RPE hyperpigmentation |

TABLE 9-continued

Donor information
SI Table 1. Donor information

| | | Submacular Pathology | |
|---|---|---|---|
| Donor Age | Ethnicity/sex | CM cultured | CM Vehicle cultured |
| 79 | CF | CNV | Few hard drusen, focal RPE hyperpigmentation |
| 79 | CF | Large CNV | CNV |
| 81 | CF | CNV, (Fuch's dystrophy donor) | Mixed size drusen |
| 82 | CF | Extrafoveal GA, soft drusen | Extrafoveal GA, soft drusen |
| 86 | CM | Extensive soft drusen, small CNV | Extensive soft drusen, small CNV |
| 86 | CF | CNV | CNV |
| 90 | CM | Large CNV | Large CNV |
| 92 | CF | GA with central RPE preservation | GA with large, calcified drusen |
| 98 | CM | Confluent soft drusen | Confluent soft drusen |
| D. Adult RPE on AMD and non-AMD Bruch's membrane (mean age 75.7 ± 1.38 yrs.) | | | |
| 71 | CF | Extrafoveal GA, soft drusen | Unknown |
| 73 | CF | Unknown (poor RPE preservation) | Unknown |
| 73 | CM | Normal | Normal |
| 75 | CF | Normal | Few hard drusen |
| 78 | CF | Normal | Normal |
| 80 | CM | Cluster of soft drusen | Few intermediate size drusen |
| 80 | CM | Extrafoveal drusen including calcified drusen, macula normal | Few hard drusen |

There was no statistically significant difference in ages of Bruch's membrane between groups (hES-RPE vs. combined AMD and non-AMD fRPE vs. adult RPE, One Way ANOVA P = 0.354). For AMD vs non-AMD, normal, there was no significant difference in the ages of the two groups (unpaired t-test, P = 0.226).

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A kit comprising a first active fraction of conditioned media and a second active fraction of conditioned media, wherein the first active fraction and the second active fraction are prepared by a method comprising the steps of:
   (a) culturing cells capable of generating extracellular matrix on a base matrix in a media for culturing said cells;
   (b) harvesting an unfractionated conditioned media from said cells, wherein the source of said cells is selected from the group consisting of corneal endothelial cells and retinal pigment epithelial (RPE) cells;
   (c) separating said first active fraction and said second active fraction from said unfractionated conditioned media by a first centrifugal filtration and a second centrifugal filtration, wherein said first centrifugal filtration uses a 50 kDa molecular weight cutoff filter for said first active fraction and said second centrifugal filtration uses a <3 kDa molecular weight cutoff filter for said second active fraction, and wherein said first centrifugal filtration is applied directly to said unfractionated conditioned media and said second centrifugal filtration is applied to either one of (i) directly to said unfractionated conditioned media or (ii) to said first active fraction; and
   (d) collecting said first active fraction and said second active fraction,
   wherein the kit does not comprise unfractionated conditioned media.

2. The kit of claim 1, wherein the first active fraction comprises Gas6.

3. The kit of claim 1, wherein the first active fraction further comprises a pharmaceutically acceptable carrier and wherein the second active fraction further comprises a pharmaceutically acceptable carrier.

4. The kit of claim 1, wherein said kit further comprises instructions for growing said source of cells on said base matrix.

5. The kit of claim 1, wherein the source of said cells is corneal endothelial cells.

6. The kit of claim 5, wherein the corneal endothelial cells are bovine corneal endothelial cells (BCE).

7. The kit of claim 1, wherein said first active fraction undergoes an additional centrifugal filtration, wherein said additional centrifugal filtration uses a 10 kDa molecular weight cutoff filter.

8. The kit of claim 1, further comprising (e) combining said first active fraction is combined with said second active fraction.

9. The kit of claim 7, further comprising (e) combining said first active fraction is combined with said second active fraction.

* * * * *